US009492074B1

(12) United States Patent
Lee et al.

(10) Patent No.: US 9,492,074 B1
(45) Date of Patent: Nov. 15, 2016

(54) COMPUTERIZED REFRACTION AND ASTIGMATISM DETERMINATION

(71) Applicants: Steven P. Lee, Chicago, IL (US); Aaron Dallek, Chicago, IL (US)

(72) Inventors: Steven P. Lee, Chicago, IL (US); Aaron Dallek, Chicago, IL (US)

(73) Assignee: Opternative, Inc., Chicago, IL (US)

( * ) Notice: Subject to any disclaimer, the term of this patent is extended or adjusted under 35 U.S.C. 154(b) by 0 days.

(21) Appl. No.: 14/856,849

(22) Filed: Sep. 17, 2015

Related U.S. Application Data

(60) Provisional application No. 62/155,080, filed on Apr. 30, 2015.

(51) Int. Cl.
| | |
|---|---|
| *A61B 3/02* | (2006.01) |
| *A61B 3/032* | (2006.01) |
| *A61B 3/00* | (2006.01) |
| *A61B 5/00* | (2006.01) |
| *A61B 3/11* | (2006.01) |
| *A61B 3/036* | (2006.01) |

(52) U.S. Cl.
CPC ............. *A61B 3/032* (2013.01); *A61B 3/0025* (2013.01); *A61B 3/036* (2013.01); *A61B 3/111* (2013.01); *A61B 5/0022* (2013.01); *A61B 2560/0223* (2013.01)

(58) Field of Classification Search
CPC  A61B 3/0033; A61B 3/0058; A61B 3/0083; A61B 3/028; A61B 3/032; A61B 3/036

USPC ................ 351/222, 223, 237, 239, 246, 241
See application file for complete search history.

(56) References Cited

U.S. PATENT DOCUMENTS

| | | | | |
|---|---|---|---|---|
| 9,177,355 B1 * | 11/2015 | Buchheit | .................. | G09G 5/00 |
| 9,237,842 B2 * | 1/2016 | Lee | ...................... | A61B 3/0041 |

\* cited by examiner

*Primary Examiner* — Huy K Mai
(74) *Attorney, Agent, or Firm* — K&L Gates LLP

(57) ABSTRACT

The present disclosure relates generally to a system and method for determining the refractive error of a patient, more particularly determining the patient's refractive error by using a computerized screen, and providing the patient with a prescription for the patient's preferred type of corrective lenses. The system and method do not require the trip or expense of a doctor visit, and are optimized for convenience and cost effectiveness. In a general embodiment, the present disclosure provides a method for determining a corrective lenses prescription of a patient. The method includes, separately, for each eye of the patient, determining an astigmatism prescription for the patient via a computerized screen and without the use of a refractor lens assembly, including testing for a cylinder component and an axis component at the same time by presenting at least one diagram to the patient via the computerized screen and enabling the patient to select at least one input per diagram corresponding to a cylinder measurement and an axis measurement for the corrective lenses prescription for the patient.

20 Claims, 23 Drawing Sheets

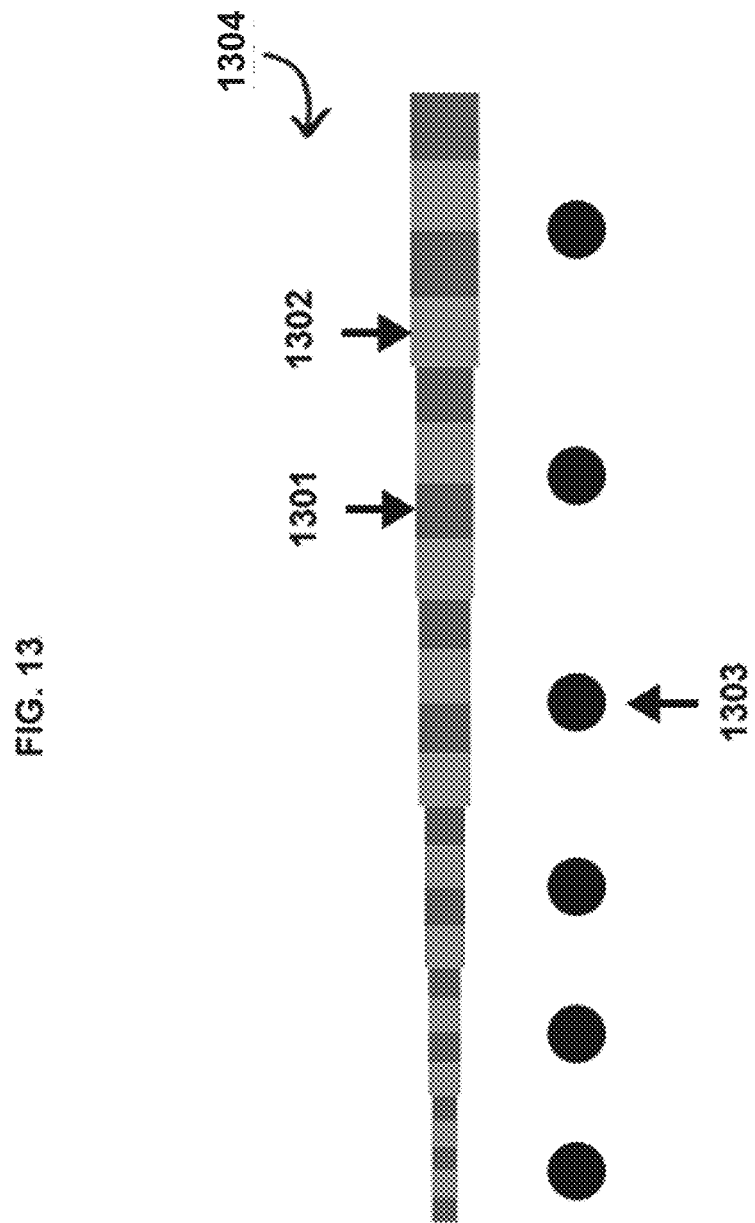

COMPUTERIZED REFRACTION AND ASTIGMATISM DETERMINATION

PRIORITY CLAIM

This non-provisional patent application claims priority to and the benefit of U.S. Provisional Patent Application Ser. No. 62/185,080, titled "COMPUTERIZED REFRACTION AND ASTIGMATISM DETERMINATION," filed on Apr. 30, 2015; the entire contents of which is expressly incorporated herein by reference.

BACKGROUND

The present disclosure is generally related to determining a glasses and/or a contacts prescription for a patient with a refractive error in need of correction. Many people have refractive errors of the eye which cause them to be either myopic (commonly known as nearsightedness) or hypermetropic (commonly known as farsightedness). One of ordinary skill in the art will understand that myopia refers to a refractive defect of the optical properties of an eye that causes images to focus forward of the retina (i.e. a refractive error). Those optical defects are typically caused by, among other things, defects of the cornea, elongation of the eye structure, other conditions, or a combination of those conditions. Hyperopia, on the other hand, refers a refractive error of the optical properties of an eye that causes images to focus behind the retina. Those optical defects are the result when the optics of the eye are not strong enough for the front to back length of the eye. Myopia and hyperopia have one component, a sphere measurement, which indicates the strength or power necessary to correct for the optical defects.

Astigmatism refers to a refractive error that causes light entering the eye to focus on two points rather than one. It is caused by an uneven power of the cornea. An astigmatism has two components, an axis measurement, which indicates the angle along which any image viewed by the patient is distorted, and a cylinder measurement, which indicates the strength or power of the distortion. Myopia, hyperopia, and astigmatism are the principle refractive errors that cause patients to seek treatment to correct their vision problems.

A manifest refraction analysis is a diagnostic tool used by ophthalmologists and optometrists whereby a patient's refractive error is tested to indicate whether the patient would benefit from correction with glasses or contact lenses. As part of that technique, a patient looks through a phoropter while the ophthalmologist or optometrist evaluates each of the patient's eyes. A retinal reflex diagnosis technique is often used to assess the magnitude of the refractive error present in the patient's eyes. Subjective feedback from the patient is used to refine the manifest refraction, which involves the patient making choices between image quality as different lenses having different powers are slid into place in the phoropter. These refractive errors can be corrected with lenses, typically spectacle lenses, known as glasses, or contact lenses, which are applied directly to the eye. They can also be corrected with various types of surgery. At the end of the manifest refraction analysis, the ophthalmologist or optometrist may produce a prescription for glasses, contact lenses, and/or refractive surgery.

Other methods for determining the refractive error of a patient include known diagnostic devices such wavefront sensors, refractometers, and others that are well known in the art. Some of these diagnostic devices use computers to assist in determining the refractive error of the patient. For example, one implementation of a wavefront-type refractor that is well known in the art uses a "Hartmann-Shack" sensor to measure the wavefront of a light beam generated from an illumination spot projected on the retina and passed through the eye's optics. In such a wavefront type refractor, a probe beam from a laser or a super-luminescent diode is projected onto the retina through the eye's optics. Light scattered by the retina passes through the eye's optics, and emerges through the eye's pupil. The wavefront of the emerging beam carries refractive information relating to the eye's optics. For example, if the eye is emmetropic (i.e., the eye's optics are without refractive error), the wavefront of the emerging beam should be flat. Relay optics relay the wavefront emerging from eye's pupil onto the Hartmann-Shack sensor. The Hartmann-Shack sensor measures the distortion of the wavefront and provides that information to a computer to compute the refractive errors of the eye due to aberrations of the eye's optics.

Each of the above-described techniques for determining a patient's refractive error requires the patient to travel to a place where such machines or doctors are present and available to perform the determination. And, having traveled to a doctor's office, a patient then has to pay for the time and services of the doctor, which may or may not be covered by their health insurance. This can be both expensive and inconvenient for a patient.

For a patient who desires contacts, a second charge generally applies for a "fitting." This charge is frequently unnecessary because most contacts manufacturers only offer one or a few base curve and diameter combinations, meaning there is only one or a few possible "fits" for that contact. When a patient has worn contacts before and is comfortable in their previous brand, there is no need to perform a "fitting." Despite this, it is commonly required by doctor's offices that a "fitting" be performed, and the accompanying fee charged. Health insurance seldom covers this fee. In some cases, the doctor may require that the patient make another, separate office visit to have their "fitting." Therefore, determining a contacts prescription can be even more expensive and inconvenient for a patient.

In addition, the cost of the above described machinery (phoropter, wavefront refractor, etc.) is prohibitive to ownership by an individual not engaged in a medical practice, so patients do not have the option of determining their own glasses or contacts prescription outside of a medical practice setting.

Furthermore, in-office subjective astigmatism tests generally only determine a patient's axis prescription within 10° of accuracy.

Thus, there exists a need for a more convenient, less costly, more accurate way for patients to determine and receive glasses and contacts prescriptions.

SUMMARY

The present disclosure relates generally to a system and method for determining the refractive error of a patient, more particularly determining the patient's refractive error by using a computerized screen or other suitable visual tool, and without the use of a refractor lens assembly, and providing the patient with a corrective lenses prescription for the patient's preferred type of corrective lenses. The system and method do not require the trip or expense of a doctor visit, and are optimized for convenience and cost effectiveness.

In a general embodiment, the present disclosure provides a method for determining a corrective lenses prescription of a patient. The method includes, separately, for each eye of the patient, determining the astigmatism prescription of the patient via a computerized screen without the use of a refractor lens assembly.

In an embodiment, determining the astigmatism prescription of the patient via the computerized screen and without the use of a refractor lens assembly includes testing for a cylinder component and an axis component at the same time by presenting at least one diagram to the patient via the computerized screen and enabling the patient to select at least one input per diagram. The at least one input per diagram corresponds to a cylinder measurement and an axis measurement used to determine the cylinder component and the axis component of the corrective lenses prescription for the patient.

In a further embodiment, the cylinder component is based, at least in part, on the cylinder measurements from the at least one input per diagram. In another further embodiment, the axis component is based, at least in part, on the axis measurements from the at least one input per diagram.

In a further embodiment, presenting the at least one diagram includes sequentially presenting at least two diagrams having at least two portions. In another further embodiment, the at least two diagrams differ from each other by at least the spacing between the at least two portions. In a still further embodiment, the at least two diagrams are the same diagram.

In a further embodiment, the method includes determining a pupillary distance measurement for the patient based on a known canthal distance (based on an age and a gender of the patient) and at least one calibration data point.

In an embodiment, the method is provided via an internet.

In an embodiment, the method includes sending the determined cylinder component and the determined axis component of the corrective lenses prescription for the patient to at least one doctor for review and approval.

In another further embodiment, the method includes determining a sphere component of the corrective lenses prescription for the patient via the computerized screen. The method includes (i) presenting a first figure to a patient via the computerized screen. The first figure is too small to be clearly seen by the patient. The method further includes (ii) enabling the patient to make at least one input to increase the size of the first figure until it can just barely be made out by the patient. The at least one input corresponds to a first sphere measurement.

In a still further embodiment, the method includes (iii) presenting a second figure to a patient via the computerized screen. The second figure is large enough to be clearly seen by the patient. The method (iv) enables the patient to make at least one input to decrease the size of the second figure just until it can no longer be made out by the patient. The at least one input corresponds to a second sphere measurement.

In another further embodiment, the method includes determining a final sphere measurement based, at least in part, on the first sphere measurement and the second sphere measurement. In yet another further embodiment, the method includes repeating at least one of steps (i) and (ii), or steps (iii) and (iv) at least once.

In a further embodiment, the method includes that the computerized screen is located a distance from the patient, in a kiosk. In another further embodiment, the method includes instructing the patient to take a determined number of heel-to-toe steps from the computerized screen to reach the distance. In a still further embodiment, the determination of the number of heel-to-toe steps is based on at least a shoe size of the patient.

In another further embodiment, determining the corrective lenses prescription for the patient is based, in part, on a previous corrective lenses prescription for the patient.

In another embodiment, the present disclosure provides a non-transitory computer readable medium. The non-transitory computer readable medium includes a plurality of instructions, which when executed by at least one processor, cause the at least one processor to operate with at least one display device, at least one memory device, and at least one input device to determine a corrective lenses prescription of the patient without the use of a refractor lens assembly. The corrective lenses prescription comprises an astigmatism prescription and a power. The non-transitory computer readable medium determines the corrective lenses prescription of the patient by, for each eye of the patient, determining the astigmatism prescription of the patient. The non-transitory computer readable medium determines the astigmatism prescription of the patient by presenting at least one diagram to the patient via a computerized screen (without the use of a refractor lens assembly) and enabling the patient to select at least one input per diagram. The patient-selected input corresponds to a cylinder measurement and an axis measurement used to determine the corrective lenses prescription for the patient. The non-transitory computer readable medium further determines the corrective lenses prescription of the patient by, for each eye of the patient, determining the power of the corrective lenses prescription of the patient. The non-transitory computer readable medium determines the power of the prescription by presenting a first figure to a patient via the computerized screen. The first figure is too small to be clearly seen by the patient. The non-transitory computer readable medium further determines the power of the prescription by enabling the patient to make at least one input to increase the size of the first figure until it can just barely be made out by the patient. The at least one input corresponds to a first sphere measurement. The non-transitory computer readable medium further determines the power of the prescription by presenting a second figure to a patient via the computerized screen. The second figure is large enough to be clearly seen by the patient. The non-transitory computer readable medium further determines the power of the prescription by enabling the patient to make at least one input to decrease the size of the second figure just until it can no longer be made out by the patient. The at least one input corresponds to a second sphere measurement. The non-transitory computer readable medium determines a final sphere measurement based, at least in part, on the first sphere measurement and the second sphere measurement.

In a further embodiment, the non-transitory computer readable medium presenting at least one diagram to the patient further includes presenting at least two diagrams. The at least two diagrams each include at least two portions. The at least two diagrams differ from each other by at least the spacing between the at least two portions.

In another further embodiment, the non-transitory computer readable medium further determines a pupillary distance measurement for the patient based on a known canthal distance based on an age and a gender of the patient and at least one calibration data point.

In a further embodiment, the non-transitory computer readable medium further includes sending the determined corrective lenses prescription to at least one doctor for review and approval.

An advantage of the present disclosure is to provide a patient more convenience in determining and receiving a glasses and/or contacts prescription.

An advantage of the present disclosure is to reduce the cost and expense to the patient of determining and receiving a glasses and/or contacts prescription.

Another advantage of the present disclosure is to determine a glasses and/or contacts prescription without the need for expensive equipment only feasible for use in a doctor office.

Another advantage of the present disclosure is to determine a glasses and/or contacts prescription without placing lenses or a lens assembly before the eyes of the patient.

Still another advantage of the present disclosure is to more quickly determine a glasses and/or contacts prescription.

A further advantage of the present disclosure is to more accurately determine the axis and cylinder astigmatism prescriptions of a patient.

Additional features and advantages are described herein, and will be apparent from the following Detailed Description and the figures.

BRIEF DESCRIPTION OF THE FIGURES

FIG. 13 illustrates a screen shot of an example of an embodiment of the system of the present disclosure, wherein the system displays line diagram 1304, and enables a patient to make at least one input, wherein the at least one input corresponds to a cylinder measurement.

DETAILED DESCRIPTION

Figure 1A:
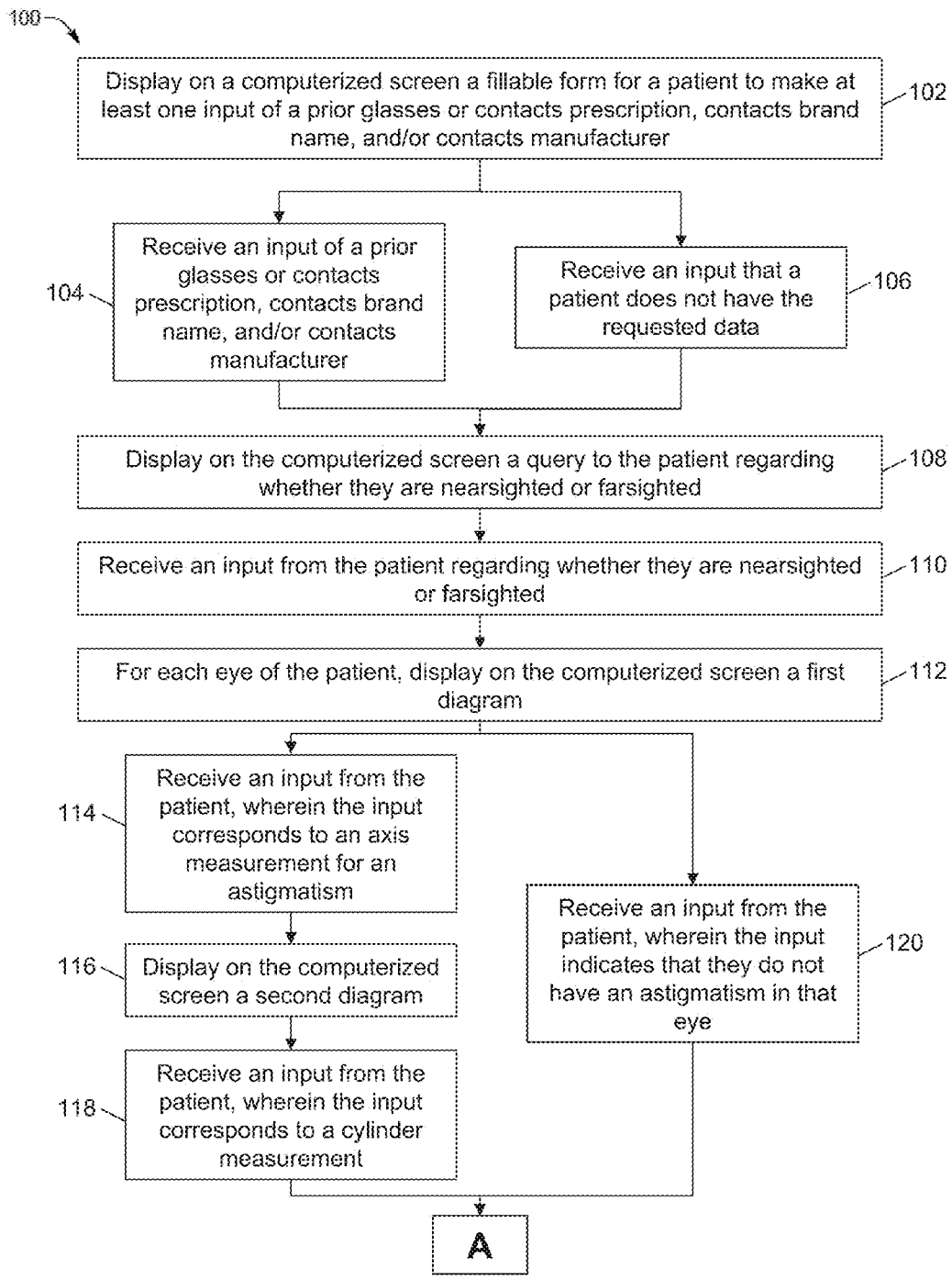
FIGS. 1A and 1B are a flowchart illustrating an example method of operating an embodiment of the system of the present disclosure.
Figure 1B:
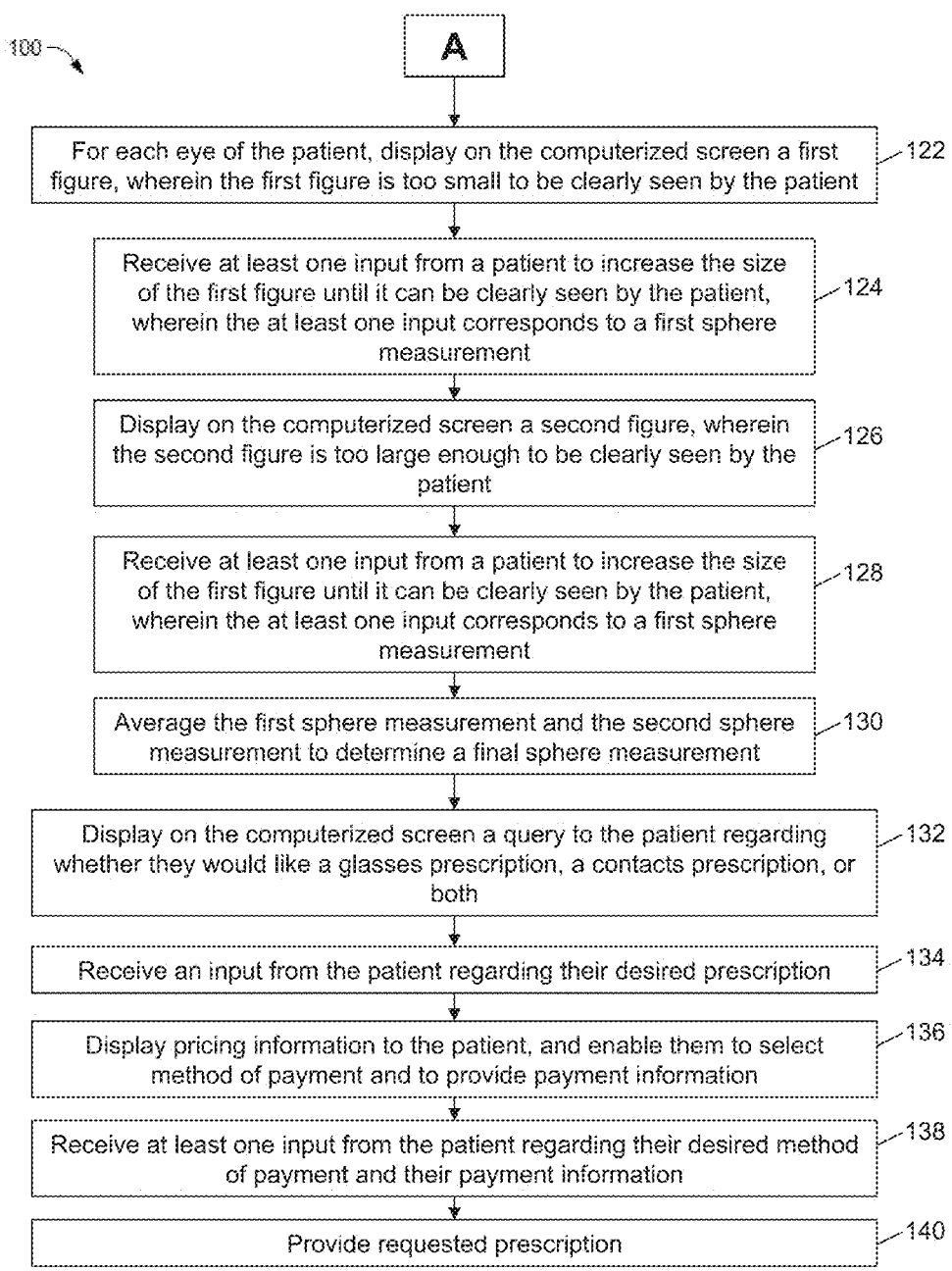

FIGS. 1A and 1B illustrate a flowchart of an example of a process or method 100 pursuant to an embodiment of the system of the present disclosure. In various embodiments, one or more processors execute a set of instructions to implement the process 100. Although process 100 is described with reference to the flowchart shown in FIGS. 1A and 1B, the system may employ many other processes of performing the acts associated with this illustrated process. For example, the system may change the order of certain of the illustrated blocks. The system can also make certain of the illustrated blocks optional, the system may repeat certain of the illustrated blocks, and/or the system may not employ certain of the illustrated blocks.

As indicated by block 102, the system displays on a computerized screen a fillable form for a patient to make at least one input of a prior glasses or contacts prescription, contacts brand name, and/or contacts manufacturer.

A computerized screen in accordance with an embodiment of the present disclosure includes, without limitation: a monitor, a television display, a plasma display, a liquid crystal display (LCD), a display based on light emitting diodes (LEDs), a display based on a plurality of organic light-emitting diodes (OLEDs), a display based on polymer light-emitting diodes (PLEDs), a display based on a plurality of surface-conduction electron-emitters (SEDs), or any other suitable electronic device or display mechanism. In certain embodiments, as described above, the computerized screen includes a touch-screen. It should be appreciated that the computerized screen may be of any suitable size, shape, and configuration.

The computerized screen displays a fillable form, fillable fields, or other vehicle for the patient to input data, if the patient has such data, including a prior glasses prescription, a prior contacts prescription, a prior contacts brand name, and/or a prior contacts manufacturer. The data related to the prior contacts prescription can be information from a box of the patient's contacts, which they may still have in their possession. In one embodiment, the computerized screen is part of a patient terminal, which the patient may use to access the system and process.

In another example embodiment, the fillable form may query the patient regarding their satisfaction with their current glasses or contact lenses, as well as how often they wear the glasses or contact lenses.

As indicated by block 104, the system receives at least one input of a prior glasses prescription, a prior contacts prescription, a prior contacts brand name, and/or a prior contacts manufacturer. It should be appreciated that the system may automatically fill in or populate the form, fields, or other vehicle based on other data input by the patient. As one non-limiting example, the patient may input a prior contacts brand name. The system may then use a look-up table or other method to retrieve from memory the corresponding base curve and/or diameter aspects of the prior prescription. This is especially possible with respect to contacts brand names or manufacturers who provide only one or a few possible base curve and/or diameter sizes.

In one possible alternative to block 104, the system may receive an input that the patient either does not have or does not wish to enter the requested prior prescription information, as indicated by block 106. In one possible embodiment, block 106 is not a part of the process 100, and the patient must enter prior prescription information before continuing to the next block. In another possible embodiment, block 106 is part of process 100 and the patient is not required to enter any prior prescription information before continuing to the next block.

The system displays on the computerized screen a query to the patient regarding whether they are nearsighted or farsighted, as indicated by block 108, and receives at least one input from the patient in response to the query regarding whether they are nearsighted or farsighted, as indicated by block 110.

At block 112, the system displays a first diagram to the patient on the computerized screen intended for a first eye (either right or left) of the patient. It should be appreciated that the patient should view the first diagram with their uncorrected first eye, i.e. if they wear glass or contacts, they should remove them and view the diagram without the correction of their glasses or contacts.

The system receives an input from the patient regarding how they view the first diagram with their first eye, wherein the input from the patient corresponds to an axis measurement for an astigmatism, as indicated by block 114. It should be appreciated that the axis measurement can be used as at least one part of a skew function which the system may apply to other diagrams and figures displayed for the first eye. In one embodiment, the system receives an input from a patient, wherein the input indicates that they do not have an astigmatism in the eye being tested, as indicated by block 120. In this embodiment, the patient may either move on to blocks 122 through 130 with their first eye, or they may repeat block 112 with their second eye.

If the patient makes an input which indicates an axis measurement in accordance with block 114, the system displays a second diagram on the computerized screen, as indicated by block 116. In one embodiment, the first diagram and second diagram are the same diagram. In another embodiment, the first diagram and the second diagram are different diagrams. In one embodiment, the second diagram is distorted based on the partial skew from the axis measurement determined from the patient's input at block 114. For example, the second diagram may be stretched or elongated by some unit along the patient-identified axis. In another embodiment, the second diagram is not initially distorted.

The system receives at least one input from the patient, wherein the at least one input corresponds to a cylinder measurement of the first eye, as indicated by block 118. It should be appreciated that the cylinder measurement can be used as at least one part of a skew function which the system may apply to other diagrams and figures displayed for the first eye. The skew function is intended to correct for any astigmatism that the patient may have in the eye being tested. As such, the skew function will make any diagram or figure it is applied appear distorted to a corrected eye, while appearing clear to a corrected eye.

It should be appreciated that blocks 112 through 120 should be repeated, separately, for the second eye of the patient. After repeating blocks 112 through 120 for the second eye, it should be appreciated that the axis measurement and cylinder measurement for the second eye can be used as parts of a skew function which the system may apply to other diagrams and figures displayed for the second eye in the same way those measurements were described as being used for the first eye. It should further be appreciated that, in one embodiment, immediately after completing blocks 112 through 120 for a first eye, the patient may switch to their second eye and again work through blocks 112 through 120. In an alternative embodiment, the patient may go on to other blocks, for example, blocks 122 through 130, with their first eye, before returning to blocks 112 through 120 for their second eye.

At block 122, the system displays a first figure to the patient on the computerized screen intended for a first eye (either right or left) of the patient. The first figure is displayed such that it is too small to be clearly seen by the patient. It should be appreciated that the patient should view the first figure with their uncorrected first eye, i.e. if they wear glass or contacts, they should remove them and view the figure without the correction of their glasses or contacts. In one example embodiment, the first figure is distorted by the skew function determined with the patient inputs of blocks 114 and 118 for the patient's first eye. In another example embodiment, the first figure is not distorted by the skew function.

The system receives an input from the patient regarding how they view the first figure with their first eye, wherein the input from the patient corresponds to a first sphere measurement, as indicated by block 124.

As indicated by block 126, the system displays a second figure on the computerized screen, wherein the second figure is displayed such that it is large enough to be clearly seen by the patient. In one embodiment, the first figure and second figure are the same figure. In another embodiment, the first figure and the second figure are different figures. In one embodiment, the second figure is distorted It should be appreciated that the patient should view the second figure with their uncorrected first eye, i.e. if they wear glass or contacts, they should remove them and view the figure without the correction of their glasses or contacts. In one example embodiment, the second figure is distorted by the skew function determined with the patient inputs of blocks 114 and 118 for the patient's first eye. In another example embodiment, the second figure is not distorted by the skew function.

The system receives an input from the patient regarding how they view the second figure with their first eye, wherein the input from the patient corresponds to a second sphere measurement, as indicated by block 126. The system averages the first and second sphere measurements to determine a final sphere measurement, as indicated by block 130. It should be appreciated by one of skill in the art that the system can determine a final measurement in any suitable manner, and it final measurement need not be the product of an straight average. For example, the system may use only the last-input result, only the first-input result, some weighted average based on statistical variance from other inputs, or the system may completely ignore inputs it considers to be of such a great statistical variance from other inputs that it is likely to be in error.

It should be appreciated that blocks 122 through 130 should be repeated, separately, for the second eye of the patient. It should further be appreciated that, in one embodiment, immediately after completing blocks 122 through 130 for their first eye, the patient may switch to their second eye and again work through blocks 112 through 130 for their second eye. In an alternative embodiment, the patient may have already completed blocks 112 through 120 with their second eye.

It should further be appreciated that the system may repeat sets of blocks 122 and 124 any number of times, in any order, and may alternate sets of blocks 122 and 124 with sets of blocks 126 and 128 any number of times. In one example embodiment, the system works through blocks 122 through 128 for an eye of the patient, then repeats blocks 122 and 124 again for the same eye before moving on to block 130. In this example embodiment, the three resultant sphere measurements are averaged to determine the final sphere measurement at block 130. In another example embodiment, the system works through blocks 122 and 124, then repeats blocks 122 and 124, then also works through blocks 126 and 128 two times. In this example embodiment, the four resultant sphere measurements are averaged to determine the final sphere measurement at block 130.

As indicated by block 132, the system displays on the computerized screen a query to the patient regarding whether they would like a glasses prescription, a contacts prescription, or both. At block 134, the system receives an input from the patient regarding their desired prescription or prescriptions.

The system displays pricing information to the patient, and conventionally enables the patient to select a method of payment and to provide payment information, as indicated by block 136. Enabling the patient to select their method of payment and to provide payment information may be accomplished via a fillable form, fillable fields, or some other way, as is well-known in the art. The system receives at least one input from the patient regarding their desired method of payment and their payment information, as indicated by block 138, and provides the patient their requested and paid-for prescription or prescriptions, as indicated by block 140.

In one embodiment, before the patient receives their prescription, it is sent to one or more doctors to sign off on the various determined refractive error measurements. For example, the system may send the axis measurement to be signed off upon by one doctor, the cylinder measurement to be signed off upon by another doctor, and the sphere measurement to be signed off upon by a third doctor. In an alternative example, the system may send all three measurements to the same doctor for sign off. It should be appreciated that any combination of doctors signing off on any part of the prescription may be employed for any combination of cost and time effectiveness considerations.

It should be appreciated that the system may enable the patient to make an input regarding how or where to send their selected prescription after they have received it. In one embodiment, the system may send the prescription data to an optometrist's or opthalmologist's offices, a central glasses and/or contacts fulfillment company, a glasses and/or contacts retail location (physical or virtual), or the like. In a further embodiment, the patient may select where to send the prescription by choosing from a list, a map, entering a name, or some other method.

In another embodiment, the system may enable a patient to browse eyeglass frames. In such an embodiment, the system may display an image of the patient with mock eyeglass frames displayed over the top of the patient's face, and may enable the patient to modify the appearance of the frames, for example, by changing the size, shape, color, material, texture, etc. of the mock frames. In another further embodiment, the system may determine a location for the mock lenses on the face of the patient in any suitable manner, such as via known facial or pupil recognition systems, or via a system-recognizable physical frame provided to and worn by a user. In another further embodiment, the system may display instructions for a patient to purchase their desired frames online, at a physical storefront location, or to have them shipped to a desired location.

It should be appreciated by one of skill in the art that the applicant has surprisingly discovered, and disclosed herein, a novel inversion of the conventional method of determining the refractive error for a patient. In the conventional technique, the patient is located far from a figure or diagram, and lenses of various strengths and configurations are placed before the patient's eyes. The patient provides subjective feedback on which of the lenses provides better vision quality. The doctor or technician refines the prescription by changing the lenses placed in front of the patient's eyes, until the subjective feedback from the patient indicates that the best vision quality has been accomplished by one of the provided lenses. In contrast, the embodiments of the present disclosure do not require any lenses or any lens assembly. It should be appreciated that the diagrams and figures themselves are adjusted by the inputs of the patient, and thus the necessary prescription may be determined, in whole or in part, from factors such as: the distance between the patient and the computerized screen, the original size of the diagram or figure on the computerized screen, the patient-adjusted size of the diagram or figure on the computerized screen, the number of inputs received from the patient, the amount of incremental effect of each input, and other relevant factors.

It should further be appreciated that, in some embodiments of the present disclosure, the patient may indicate to a second person which input should be made. In those embodiments, the second person would perform the input to the computerized screen, based on the instructions of the patient. The second person may be any suitable person, including a friend of the patient, family member of the patient, doctor, office assistant, office technician, or any other person.

It also be appreciated that the present disclosure is not limited to a single computerized screen. In some embodiments, the patient may use more than one computerized screen, on one or more patient terminals, to interact with the system. In another embodiment, the patient and the second person may interact with the system on the same patient terminal and/or computerized screen. In still another embodiment, the patient and the second person may interact with the system on different patient terminals and/or computerized screens.

In another embodiment the system may allow a patient to begin the process and method in one location, such as a brick and mortar location, and continue or complete the process and method in at least one other location, such as in their home. It should be appreciated that in such an embodiment some kind of unique patient identification would be used to authenticate that the same patient is interacting with the system in the first location and the additional location(s). Such authentication systems are known in the art and described below.

In another embodiment, a patient may use one computerized screen to control another computerized screen. For example, the system may enable a patient with a smartphone to use the smartphone as a remote to control another patient terminal with a computerized screen, such as a kiosk, personal computer, or tablet computer in order to interact with the system. In one example of such an embodiment, the system would send a patient a link to their remote device, such as via email or SMS text message. The patient is enabled to access the link to launch an interface, such as via a browser, which can then be used to interact with the system in a unique hand held manner. In another example embodiment, the remote device interacts with the system through an application stored on the remote device, commonly known as an "app." The remote device may be any suitable device, such as a cell phone, smart phone, tablet, notebook, or other remote device, that is capable of interacting nearly-instantaneously with the system to receive instructions and enable the patient to make at least one input to the system over at least one communication interface, such as the internet, text messaging, email, voice, or data, to control the computerized screen from a distance. It should be appreciated by one of skill in the art that such a system is unique in that it allows a patient to take a medical examination with their own smartphone or other remote device, and fully be able to control the examination.

In another embodiment, the system utilizes a handheld patient terminal with a digital screen remote from a second patient terminal with a digital screen as a remote control for testing done via the internet by effectively turning the handheld patient terminal into a remote control via a any suitable client or server application (such as a web browser). For example, the handheld patient terminal may be any suitable device, such as a cell phone, smart phone, tablet, notebook, or other remote device, that is capable of interacting nearly-instantaneously with the system to receive instructions and enable the patient to make at least one input to the system over at least one communication interface, such as the internet, text messaging, email, voice, or data, to control the computerized screen from a distance. The remote patient terminal may similarly be any suitable device with a computerized screen large enough to be viewed from a distance, such as a kiosk, personal computer, or tablet computer in order to interact with the system.

In one example embodiment of such a system, the patient is enabled to log into an online portal on either terminal, and make at least one input to request a message be sent to the handheld terminal. The message may be any suitable message, such as a text message, an email message, or a voice message. For example, the system may send the patient a text message to their smart phone after the patient requests the message by entering their cell phone number. The patient is enabled to click on or enter a link within the message, which will cause the system to open a web browsing session on the handheld terminal, transforming the handheld terminal into a remote control for the remote terminal, which is also logged into a browsing session. The system may connect the handheld terminal and the remote terminal sessions via any suitable protocol. In a further embodiment, the system connects the handheld terminal and the remote terminal sessions via a WebSocket protocol. A WebSocket protocal provides full-duplex communications channels over a single TCP connection, and allows the server to send content to a browser without being queried by the client, and maintains the same connection while messages are sent back and forth. Such a direct line of duplex communication increases the real-time speed of a remote control, making the remote more convenient for a patient, and providing a better user experience. Applicants have surprisingly found that the use of a remote control and, more specifically, the use of a WebSocket-based remote control of a smartphone, tablet, or other portable handheld device to control a web accessible computer based system, such a PC, MAC, or any tablet with a digital screen in unique and advantageous in the telemedicine space. The use of such a device, results in the ability to have real time transmission, and real time feedback to a patient when running a telemedicine based solution, which is more convenient for the patient.

In another embodiment, the system uses a voice recognition system to enable a patient to make at least one input. In a further embodiment, the system includes a voice recognition system for conducting an eye examination, or a sub-examination of an eye examination. In a such an embodiment, the system would enable a user to make an input by speaking to the system, equipped with a microphone and conventional voice recognition software. As is known in the art, microphones and voice recognition software are readily commercially available and use standard voice recognition formulas which embed a conventional automatic learning system, so that the system would be able to adapt to more difficult languages over time. The system would receive voice inputs from the patient to record and analyze them using the conventional voice recognition software. It should be appreciated by one of skill in the art that enabling a patient to provide inputs via their voice would provide several benefits. First, the patient that is taking constituent tests of an examination, such as an eye examination, would not need to see the details of the screen perfectly clearly, and could utilize their hearing (communicated through spoken instructions) and speaking (to provide inputs back to the system) instead, which is more user-friendly since it is easier to use and provides additional options for inputting responses. This is especially relevant for portions of the system in which the patient is using an uncorrected eye, is somewhat distant from the computerized screen, or both. Another benefit of such a system is that it enables a patient to use their hands for purposes other than providing inputs to the system. For example, the patient may then be free to hold up test object, or to cover their eyes. Further, the use of a system which speaks to the patient and allows the patient to respond by speaking back simulates a more typical doctor's office-based subjective eye examination, and may help patient's assimilate to the system of the present disclosure.

Figure 2A:
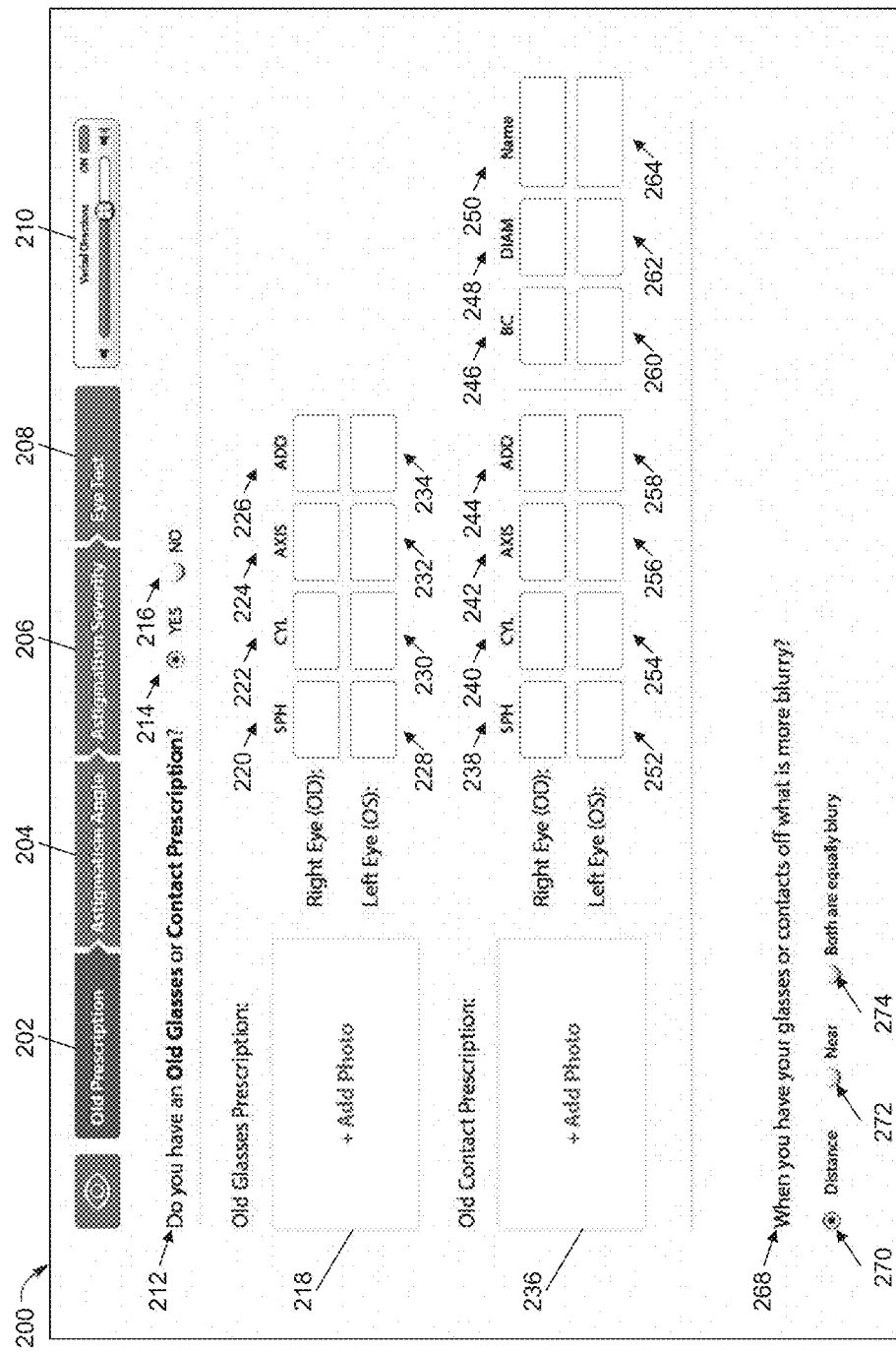
FIG. 2A illustrates a screen shot of an example of an embodiment of the system of the present disclosure, wherein the system displays requests for information regarding a prior prescription of the patient, a fillable form for the patient to enter data regarding their prior prescription, and requests for information regarding what refractive errors the patient may have.
Figure 2B:
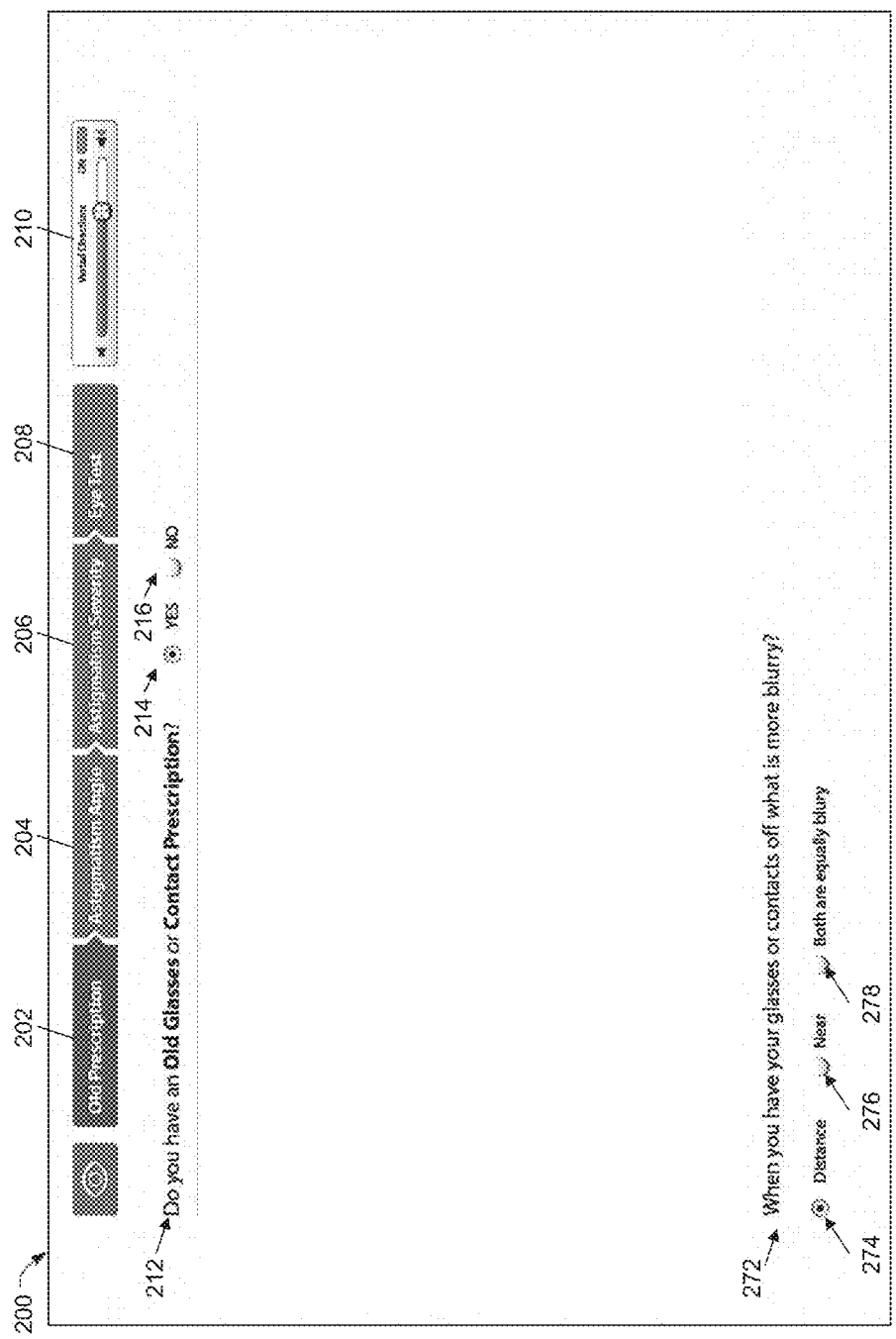
FIG. 2B illustrates a screen shot of an example of an embodiment of the system of the present disclosure, wherein the system displays a request for information regarding a prior prescription of the patient and a request for information regarding what refractive errors the patient may have.

Referring now to FIGS. 2A and 2B, an embodiment of the present disclosure is illustrated. The example system of FIG. 2A includes a display 200 which the system shows on the above-described computerized screen. The display 200 includes progress bar 202, 204, 206, and 208. It should be appreciated that the progress bar may be any suitable progress meter. In the embodiment of FIG. 2A, the progress bar 202, 204, 206 and 208 is a sectioned progress bar where the section currently being worked on 202 is indicated by being a darker color than the other sections. It should be appreciated that for a sectioned-type progress bar, or other types of progress meters, the indication of the section being worked on can be any variation in color, size, font, text, or otherwise. In another embodiment, the sections of the progress bar are selectable by the patient, such that the patient can move through the process 100 by selecting the section of the process to which they wish to go. In a different embodiment, the sections are not selectable by the patient to move the patient through the various sections.

In the embodiment illustrated by FIGS. 2A and 2B, the system provides instructions for the patient regarding how to work through the section 202, and further provides verbal instructions which the patient can control, turn off, turn on, and/or adjust by articulating the verbal direction control elements 210.

As illustrated by the embodiment shown in FIGS. 2A and 2B, the system queries the patient regarding whether they have their prior glasses or contacts prescription 212. The patient is enabled to respond to the query by selecting one of the radio buttons 214 or 216. It should be appreciated that any other method for accepting a response to a query from the patient may be employed by the system, such as a drop down list, a fillable field, and/or a check box.

In the embodiment of FIG. 2A, when the patient selects the radio button corresponding to "YES" 214, the system provides the fillable form 218 through 264. The system enables the patient to upload a picture of a prior glasses prescription 218 and/or a prior contacts prescription 236. The system also enables the patient to enter their prior prescription data into the conventional fillable fields 220 through 234 and 238 through 264. Specifically, the fillable form has fields for the glasses prescription of the patient's right eye, or "OD" 220, 222, 224, and 226. "OD" is the common acronym for the latin "oculus dextrus," which means "right eye." The fillable form also has fields for the glasses prescription of the patient's left eye, or "OS" 228, 230, 232, and 234. "OS" is the common acronym for the latin "oculus sinister," which means "left eye." More specifically, fillable fields 220 and 228 are for the sphere, or "SPH," or power measurement of the patient's right and left eyes, respectively. The sphere measurement represents the degree of nearsightedness or farsightedness of the patient. The unit of the sphere measurement is the diopter. A plus sign "+" in front of the sphere measurement indicates the amount of farsighedness of the patient, while a negative sign "−" in front of the sphere measurement indicates the amount of nearsightedness of the patient. The more positive (for farsighted people) or negative (for nearsighted people) the sphere measurement is, the more severe the refractive error, and thus, the more powerful the corrective lenses must be to correct for the error.

The cylinder, or "CYL" fields 222 and 230 for the right and left eye, respectively, and the axis fields 224 and 232, for their right and left eye, respectively, indicate that the patient has an astigmatism in the corresponding eye. If no astigmatism is present, the cylinder and axis fields are conventionally left blank. The cylinder measurement indicates the severity, in diopters, of the astigmatism in the patient's eye. The bigger the cylinder measurement, the more severe the astigmatism of the patient. The axis measurement is a number between 0° and 180°. The unit of the axis measurement is degrees. The axis measurement indicates the axis along which the patient's vision is distorted due to the imperfections in the curvature of the cornea.

The combination of sphere, cylinder and axis measurements make up the distance vision portion of the conventional eyeglasses or contacts prescription. The remainder of the glasses prescription is directed to the near vision portion of the prescription, and is generally for reading glasses or the reading portion of bifocal corrective lenses. The ADD fields 226 and 234, respectively for the right and left eyes of the patient, represent the additional refractive power, in diopters, to be added to the spherical power in order to allow the patient to read up-close if they are presbyopic. If the patient needs no correction for distance vision, the ADD power alone would be the patient's prescription for conventional reading glasses, available at most drugstores and/or convenience stores.

In an example embodiment, the system enables a patient to determine the ADD power for those patients who require it. Those patients are referred to as presbyopic emmetropes (those that do not require spectacle correction for distance), and their presbyopia is generally a result of aging, typically occurring around approximately 40 years old. This is the age period when a patient generally begins to need reading glasses. However, in the past, in order to determine a correct reading glasses ADD number, or to create a proper no-lined progressive bifocal spectacle or contact lens, patients needed to go to an eye doctor's office to obtain the proper measurement. Applicants have surprisingly found, however, a system for determining the power for both top and bottom portions of bifocal lenses which avoids the need to visit a doctor's office or endure a full and lengthy examination at the office. The system queries the patient regarding their age, the size of figures they are able to see with their uncorrected eyes (via any of the methods or processes disclosed herein), and the distance they desired to be corrected for (i.e. a patient may desire a single pair of glasses to see both books at 16 inches and to see other objects at 21 inches (or any other combination of top segment and bottom segment)). It should be appreciated that the desired distances can be determined by any suitable method, such as via a computerized screen as disclosed herein (such as a smartphone), a simple printable paper measurement aid, via estimation with a length of paper. The system may also enable a patient to estimate the distance range they most desire to be corrected for, such as the distance range they use most often, in easily estimable terms, such as arms length, further than arms length, or closer than arms length. The system utilizes such inputs from the patient to determine a custom prescription for no-line bifocals or single reading glasses without guessing or requiring a trip to a doctor's office and its associated expenses.

As shown in FIG. 2A, the contacts prescription includes many of the same measurement fields as the glasses prescription. Specifically, the sphere measurement fields, 238 and 252; the cylinder measurement fields, 240 and 254; the axis measurement fields, 242 and 256; and the add measurement fields, 244 and 258, for the right and left eyes, respectively, are also present in the contacts prescription. Although the fields have the same names and abbreviations, contacts prescriptions and glasses prescriptions can be different, partly because the lenses of glasses are further from the surface of the eye than contacts.

In addition, the system provides the additional measurement fields for the base curve, or "BC," 246 and 260, the diameter, or "DIAM," 248 and 262, and the name of the contacts brand and/or manufacturer, 250 and 264. During the time when only hard, gas permeable contact lenses were available, the base curve and diameter measurements were necessary to ensure the comfort of the rigid lenses. With the rise of soft, flexible contact lenses, many contact lens manufacturers only provide one, two, or a few different base curve or diameter options for their lenses. If the base curve and diameter measurements are known from a prior prescription, and the patient was comfortable in those lenses, then other lenses with those same measurements are highly likely to also be comfortable for the patient, even if the manufacturer is different. If the manufacturer is the same, it is even more likely that the patient will be comfortable in lenses with the same measurement. In this way, it should be appreciated that a contacts "fitting" is generally unnecessary for those who have previously worn contacts, so long as the patient was comfortable in their prior lenses. In one embodiment, for patient-identified prior contacts manufacturers or brand names, the base curve and diameter measurements can be looked up by the system in a lookup table or other memory database. In another embodiment, the system can automatically fill in, or populate, any possible fields 246, 248, 260, and/or 262 with the looked-up base curve and diameter measurements.

In an embodiment, the system can use the prior prescription information as a check on the determined current prescription. In a further embodiment, the system can require more tests from a patient to confirm the current prescription if there is a statistically significant difference between a value of the prior prescription and the corresponding value of the determined prescription.

In one embodiment, the system is capable of reading the uploaded picture or scan of the prior glasses prescription 218 and/or the prior contacts prescription 236. In a further embodiment, the system may automatically fill in, or populate, any possible fillable fields with information read from the uploaded prior glasses prescription 218 and/or the prior contacts prescription 236. In another embodiment, the patient may upload a photograph or scan of a prior contacts box or container and the system may automatically fill in, or populate, any possible fillable fields with information read from the uploaded photograph or scan of the prior contacts box or container. In another embodiment, the system is capable of recognizing conventionally encoded information, such as information from a barcode, QR code, matrix code, Aztec code, or other known types of encoded information. In a further embodiment, the system is capable of scanning the encoded information from a prior glasses or contacts prescription, and/or a prior glasses or contacts box or container. In a still further embodiment, the system may automatically fill in, or populate, any possible fillable fields with information read from the scanned prior glasses or contacts prescription, and/or a prior glasses or contacts box or container.

After the patient fills in whatever data the patient has available from prior prescriptions, the system queries the patient regarding what appears more blurry or out of focus for them when they are not using corrective lenses 268. Again, in the example embodiment of FIG. 2A, the system provides radio buttons 270, 272, and 274 for the patient to select an answer, but any suitable method for enabling an input to the query would be acceptable. If the patient selects distance 270 as being more blurry, this may suggest that they are nearsighted, and they may have some astigmatism. If the patient selects near 272 as being more blurry, this may suggest that they are farsighted, and they may have some astigmatism. If the patient selects both as being equally blurry 274, they may be nearsighted or farsighted, and they likely have an astigmatism.

As illustrated in the embodiment of FIG. 2B, when the patient responds to the query regarding whether they have a prior prescription with "NO," the system does not display the fillable form and fields 218 through 264, as in FIG. 2A. Instead, in the embodiment of FIG. 2B, the system moves directly to a presentation of query 268 and enables the patient to respond via radio buttons 270, 272 and 274, just as in FIG. 2A.

Figure 3:
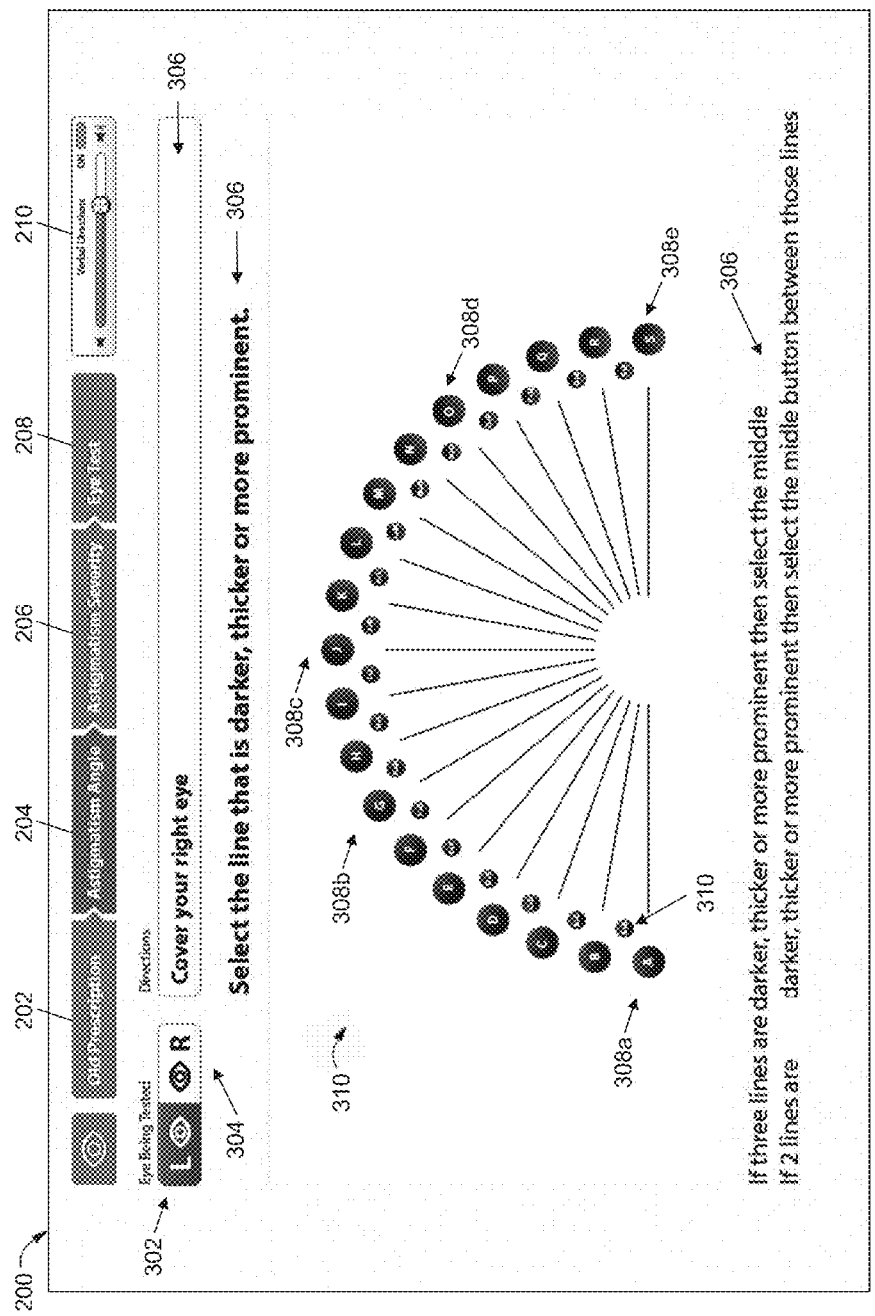
FIG. 3 illustrates a screen shot of an example of an embodiment of the system of the present disclosure, wherein the system displays a diagram and enables a patient to make an input, wherein the input corresponds to an axis measurement of the patient.

Referring now to FIG. 3, another embodiment of the present disclosure is illustrated. At this stage of the process, the system presents display 200, and the progress bar indicates that the patient is currently in the Astigmatism Angle section 204. The eye tracker 302, 304 indicates which eye is being tested. It should be appreciated that the eye tracker may be any suitable progress meter. In the embodiment of FIG. 3, the eye tracker 302, 304 is a sectioned eye tracker where the section corresponding to the eye being tested 302 is indicated by being a darker color than the other section corresponding to the other eye. It should be appreciated that for a sectioned-type eye tracker, or other types of progress meters, the indication of the eye being tested can be any variation in color, size, font, text, or otherwise. In another example embodiment, the sections of the eye tracker 302, 304 are selectable by the patient, such that the patient can change the eye being tested by selecting the section corresponding to the other eye. In a different embodiment, the sections are not selectable by the patient to change the eye being tested.

As can be seen by reference to FIG. 3, the eye tracker 302, 304 indicates that the eye being tested is the left eye, indicated by the darker shading of the left eye section 302. Written instructions 306 are provided to the patient, along with verbal instructions, which the patient can control with verbal direction control elements 210. In the example embodiment shown in FIG. 3, the written directions read "Cover your right eye. Select the line that is darker, thicker or more prominent. If three lines are darker, thicker or more prominent then select the middle. If two lines are darker, thicker or more prominent then select the middle button between those lines." The directions 306 refer the patient to the diagram 310. Diagram 310 is a known diagram for diagnosing the axis of an astigmatism. Patients with an astigmatism will see the lines around the axis of their astigmatism as more bold, or in better focus, then the other lines of the diagram. The lines correspond to angle measurements. In this example embodiment, the lines are evenly spaced at intervals of 15°. It should be appreciated that any suitable angular interval may be employed by the diagram 310. The system enables the patient to make an input of a line, or the centermost part of a group of lines, which are more prominent when the patient views the diagram. It should be appreciated that the patient is viewing the diagram with their uncorrected eye.

In the embodiment shown in FIG. 3, the letters A through S 308, as well as the smaller letter combination buttons 310 are selectable to indicate the axis angle of the patient. It should be appreciated that the axis line selectable icons 308, 310 need not be letters, but could be numbers, the angle measurement, pictures, symbols, or any other suitable icon. As shown in FIG. 3, the letter "A" 308a corresponds to an axis of 0°, the letter "G" 308b corresponds to an axis of 75°, the letter "J" 308c corresponds to an axis of 90°, the letter "O" 308d corresponds to an axis of 165°, and the letter S 308e corresponds to an axis of 180°. In another example embodiment, the system provides a button for the patient to indicate that none of the lines in the diagram appears as darker, thicker or more prominent, indicating that the patient does not have an astigmatism in that eye. In a further example embodiment, when the patient makes at least one input which indicates that they do not have an astigmatism in the eye being tested, the system moves on to test the other eye for an astigmatism. In another embodiment, when the patient makes at least one input which indicates that they do not have an astigmatism in the eye being tested, the system moves on to the eye test for that same eye, skipping the section testing the astigmatism severity for that eye. In an alternative embodiment, when the patient makes at least one input which indicates that they do not have an astigmatism in the eye being tested, the system still tests the severity of any astigmatism in that eye as a double-check that the patient does not have an astigmatism in that eye.

It should be appreciated that, after selecting the line or lines of the patient's axis measurement for the patient's left eye, as shown in FIG. 3, the system may repeat the same test with diagram 310 for the right eye by moving the eye tracker 302, 304 to indicate that the right eye 304 is being tested, and by adjusting the written instructions 306 to reflect that the right eye is now being tested. In another embodiment, the patient continues to work through the sections of the progress bar with the left eye, and, after completing the astigmatism severity test 206 for the left eye, will repeat the two astigmatism sections 204 and 206 for the right eye before moving on to the eye test 208 for either eye. In another embodiment, the patient works through all sections 204, 206, and 208 with one eye, the left eye, for example, before going back to work through each section 204, 206, and 208 with the other eye, in this example, the right eye. It should further be appreciated that any order of testing, with any order of eyes being tested is suitable. It should further be appreciated that by providing patient-selectable progress bar sections 204, 206 and 208, and eye tracker sections 302 and 304, the patient may select whichever order they prefer.

Figure 4A:
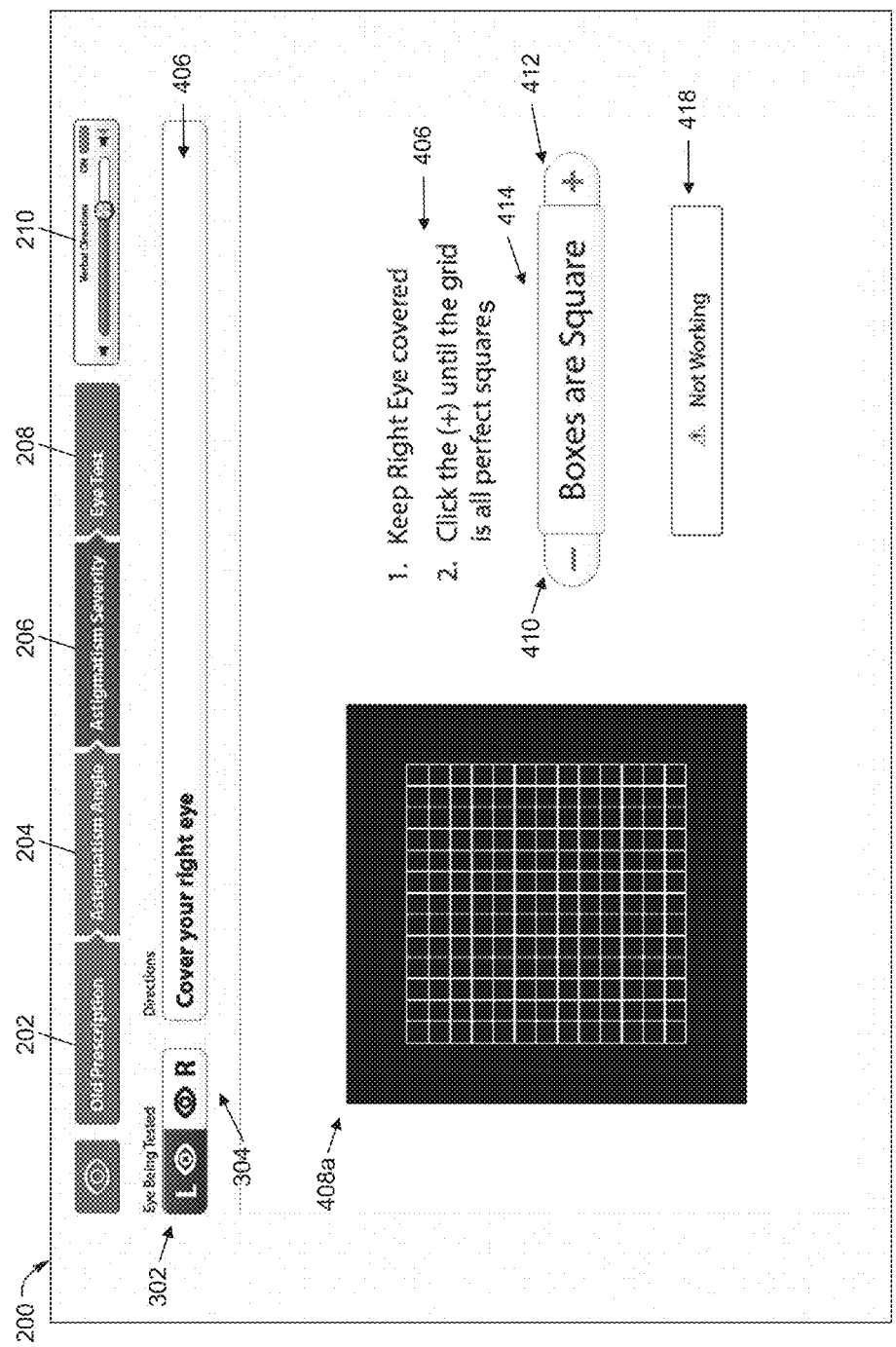
FIG. 4A illustrates a screen shot of an example of an embodiment of the system of the present disclosure, wherein a diagram is shown as it would look to a corrected eye with astigmatism, or to an eye without astigmatism.

Referring now to the embodiment illustrated in FIG. 4A, another example embodiment of the present disclosure is illustrated. At this stage of the process, the system presents display 200, and the progress bar indicates that the patient is currently in the Astigmatism Severity section 206. The eye tracker 302, 304 indicates that the left eye 302 is being tested. The written directions 406 read: "Cover your right eye. 1. Keep Right Eye covered. 2. Click the (+) until the grid is all perfect squares." The written instructions refer to diagram 408a, which shows a large square divided into several smaller squares. The system provides patient-selectable icons 410 and 412 to adjust the diagram until the patient views all of the grid of diagram 408a as perfectly square. When the patient views all of the grid of diagram 408a as perfectly square, the patient selects the patient-selectable icon 414. If the system is malfunctioning in some way, the system provides a button 418 to request assistance with the malfunction. It should be appreciated that button 418 is optional, but useful in the case that the animation of the diagram changing is not visible to the patient. It should further be appreciated that diagram 408a in FIG. 4A is illustrated as it would appear to a patient without an astigmatism, or to a patient with an astigmatism who is wearing their corrective lens on the eye being tested. In other words, the boxes of diagram 408a are square in FIG. 4A, but would appear distorted to an uncorrected eye with an astigmatism.

The applicant has surprisingly found that use of the grid shown as diagram 408a can be used to determine the cylinder prescription of a patient by measuring the amount of distortion is necessary, along the patient's axis of astigmatism, in order for the patient to view the figure as square to their uncorrected eye.

Figure 4B:
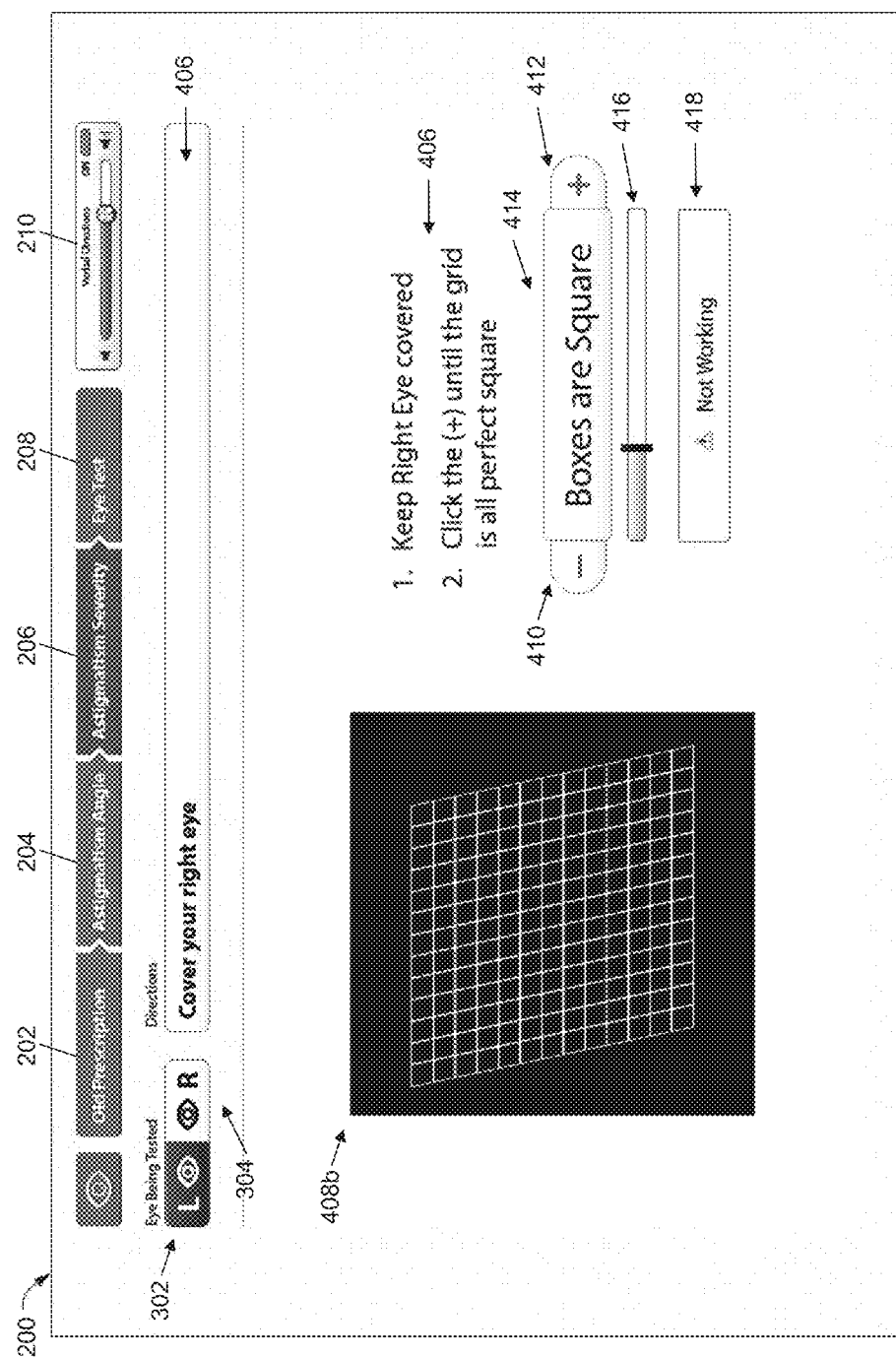
FIGS. 4B, 4C, 4D, and 4E illustrate screen shots of examples of embodiments of the system of the present disclosure, wherein each diagram is shown as it would look to an uncorrected eye with astigmatism along a given axis.
Figure 4C:
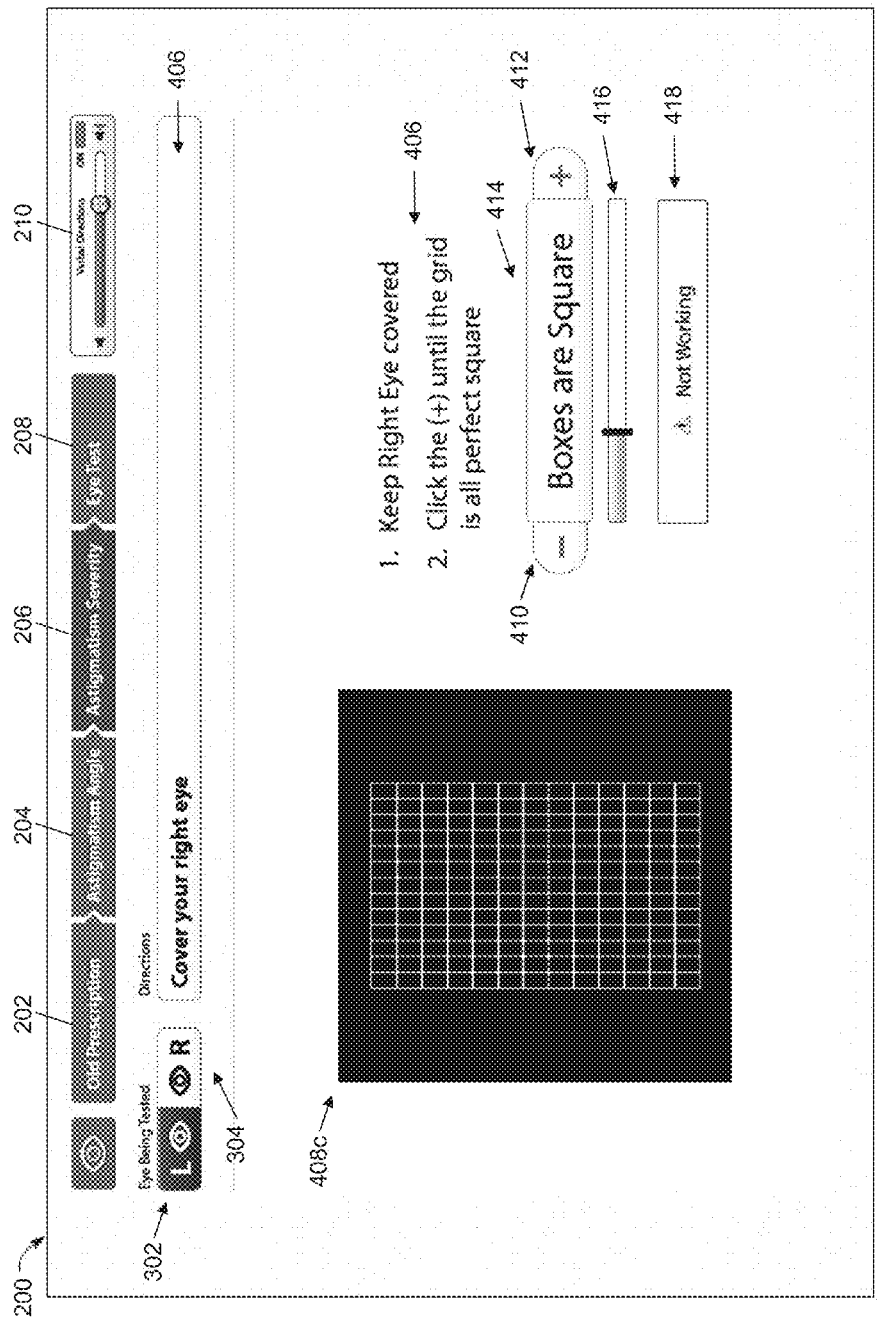
Figure 4D:
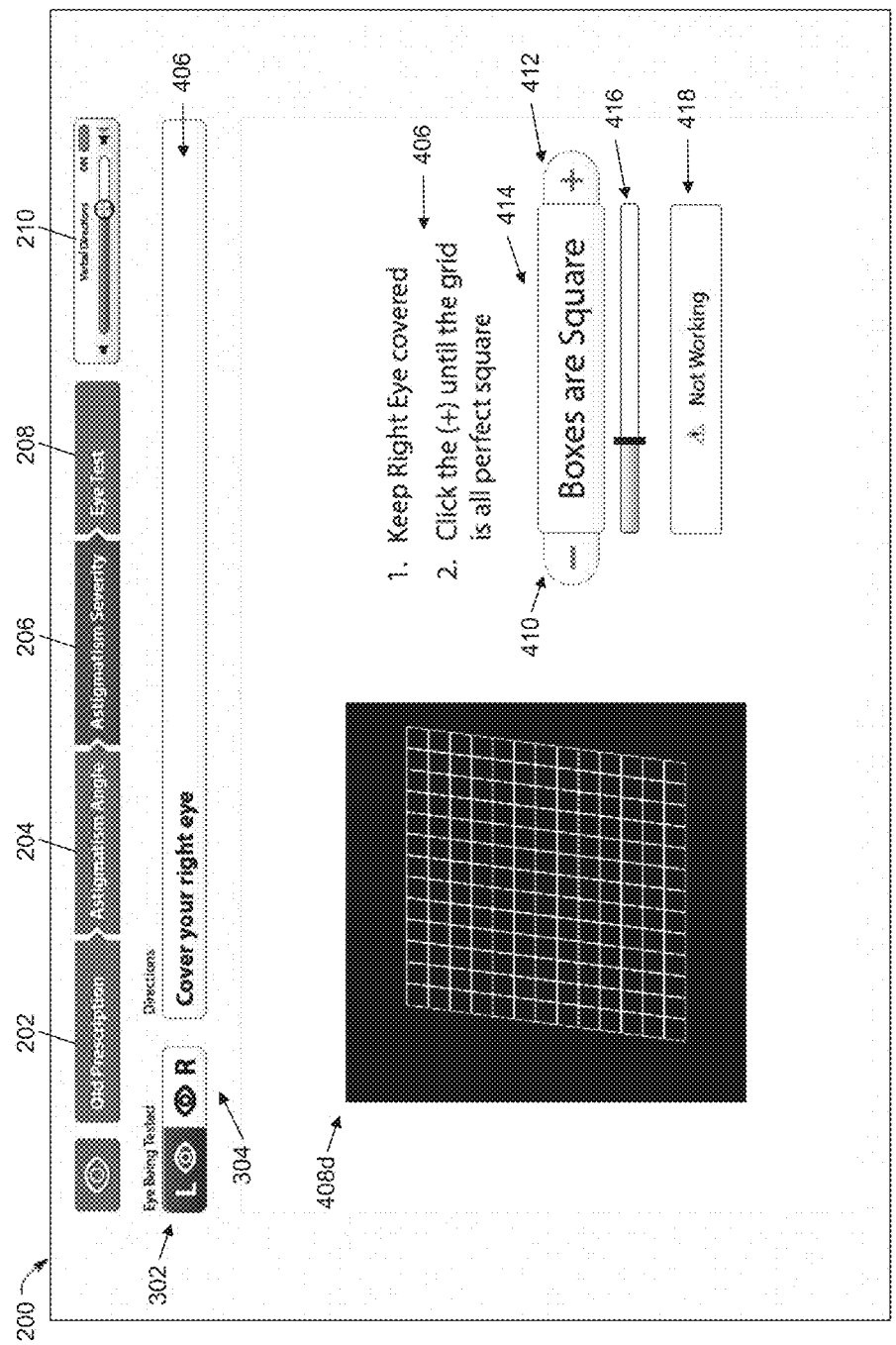
Figure 4E:
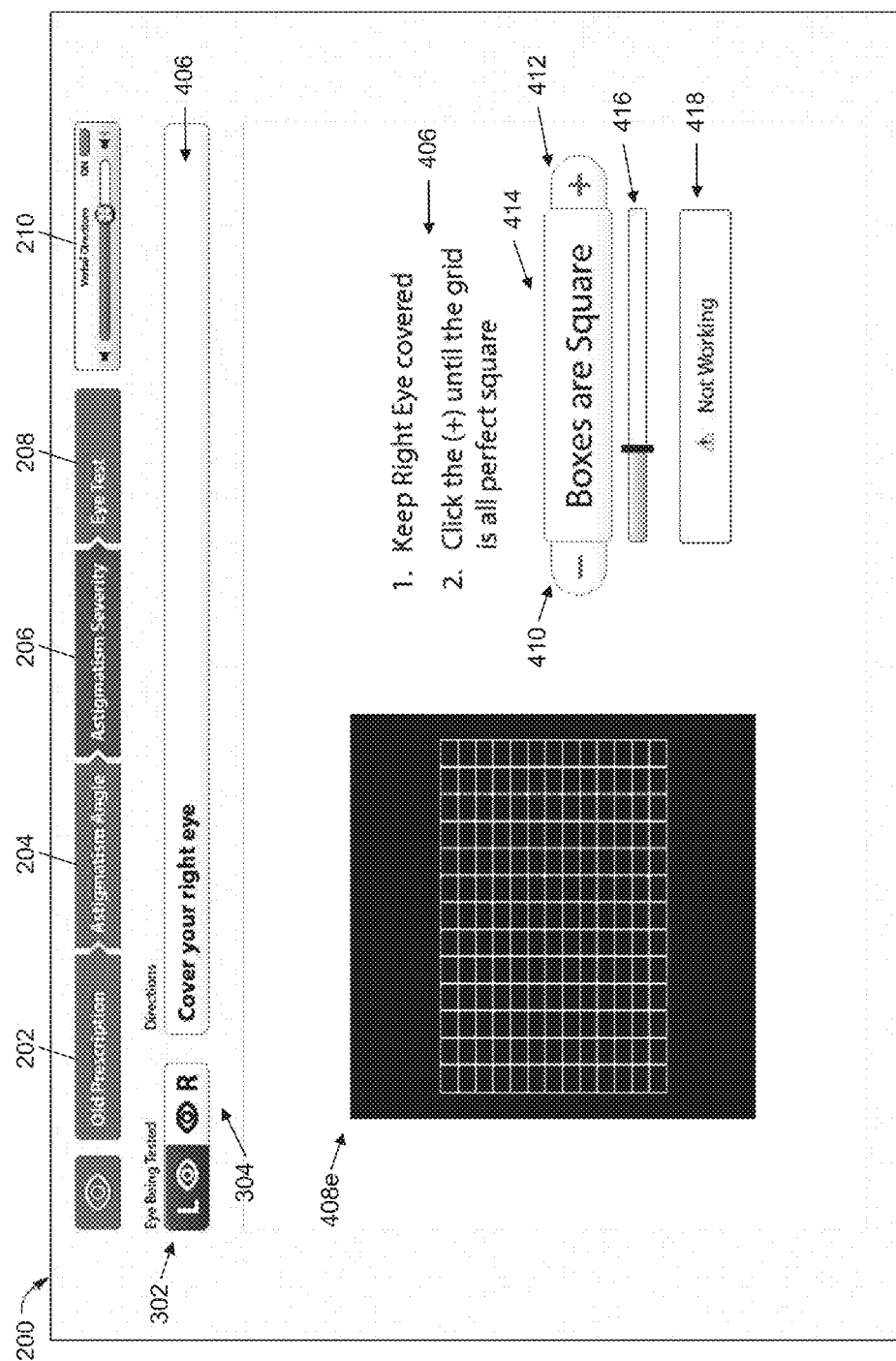

Referring now to the embodiments illustrated in FIGS. 4B, 4C, 4D and 4E, other embodiments of the present disclosure are illustrated. In the embodiments of these figures, the patient has selected icons 308a, 308b, 308c, 308d, and 308e of FIG. 3, respectively. Thus, the corresponding diagrams of those FIGS. 408b, 408c, 408d, and 408e, respectively, are illustrated as being stretched along the patient-selected axis for that figure. Specifically, FIG. 4B shows the diagram 408b distorted along the 75° axis, FIG. 4C shows the diagram 408c distorted along the 90° axis, FIG. 4D shows the diagram 408d distorted along the 165° axis, and FIG. 4E shows diagram 408e distorted along the 180° axis. If the patient selects the "+" 412, the diagram elongates along the axis. If the patient selects the "−" 410, the diagram contracts along the axis. In this way, the patient can manipulate the diagram until the boxes appear square to their uncorrected eye. As the patient manipulates the diagram, scale 416 provides a visual representation to the patient of how much they have changed the diagram 408b, 408c, 408d, or 408e.

It should be appreciated that the system may distort the diagram in any suitable way, at any suitable speed, and at any suitable increment. In one embodiment, the system automatically distorts the diagram prior to enabling the patient to make an input. In another embodiment, the system automatically begins distorting the diagram, and continues to distort the diagram until the patient makes an input to stop the distortion. In a further embodiment, the patient may further adjust the distortion of the diagram by making at least one input. In another further embodiment, the patient may not further adjust the distortion of the diagram by making any inputs. In another embodiment, the system does not distort the diagram prior to receiving at least one input from the patient.

Figure 5:
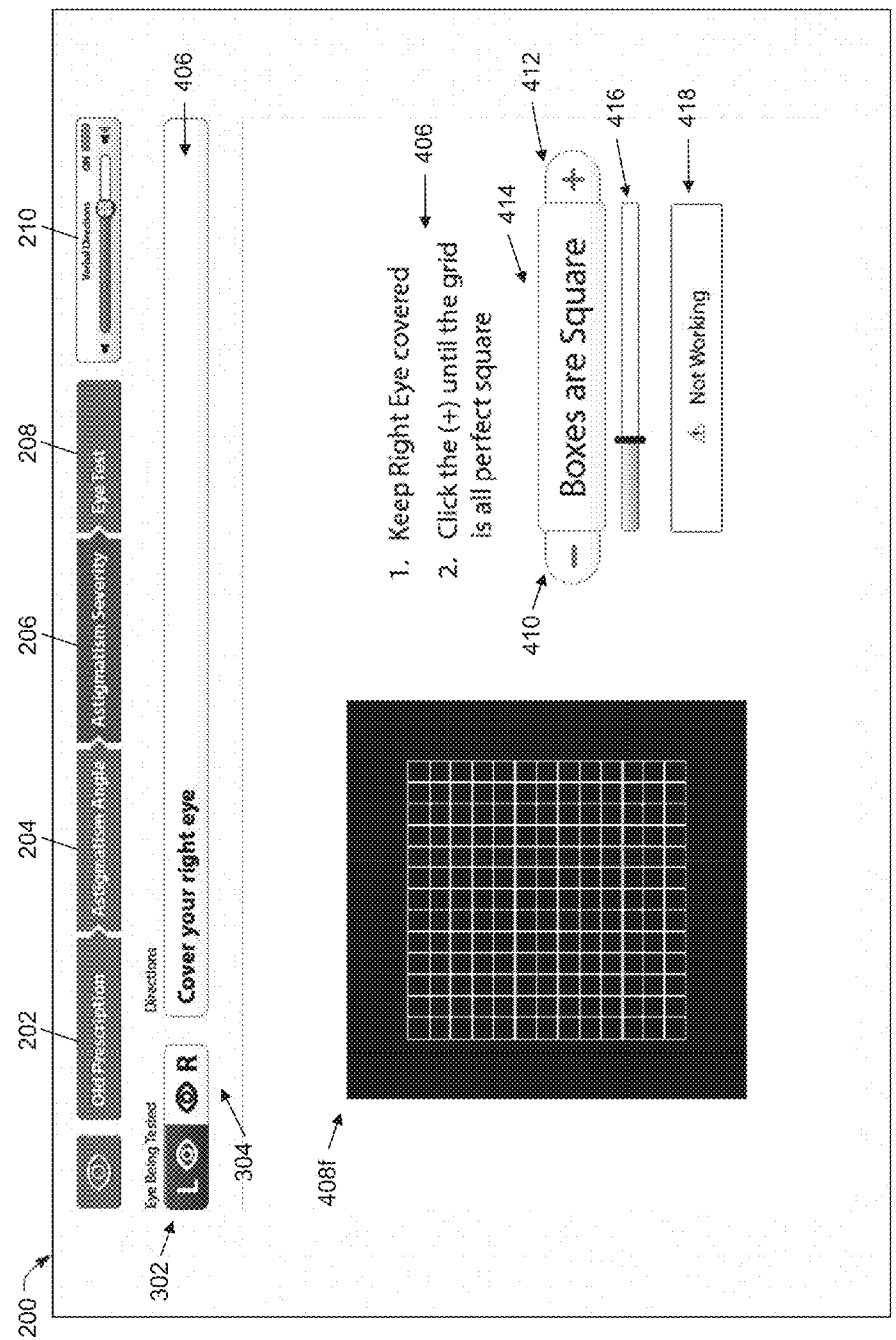
FIG. 5 illustrates a screen shot of an example of an embodiment of the system of the present disclosure, wherein the diagram is shown as it would look to a corrected eye with astigmatism after the patient has made at least one input, wherein the input corresponds to a cylinder measurement of the patient.

Referring now to the embodiment illustrated in FIG. 5, another embodiment of the present disclosure is illustrated. As shown in FIG. 5, the patient has manipulated diagram 408f such that, to the patient's uncorrected eye, the boxes appear square. Scale 416 demonstrates that the diagram 408f has been manipulated. At this point, the patient can press the icon 414 indicating that they view the boxes of the diagram 408f as square. The system determines, from the amount of manipulation of diagram 408f, a cylinder measurement for that eye of the patient.

It should be appreciated that the combination of the axis measurement and the cylinder measurement for a given eye of the patient can be used by the system to determine a skew function to apply to further diagrams and figures intended for the given eye. In this way, the astigmatism will not affect the results of the eye test, for example, because the figures used in the eye test will have been modified to counter the effect of the astigmatism.

Figure 6:
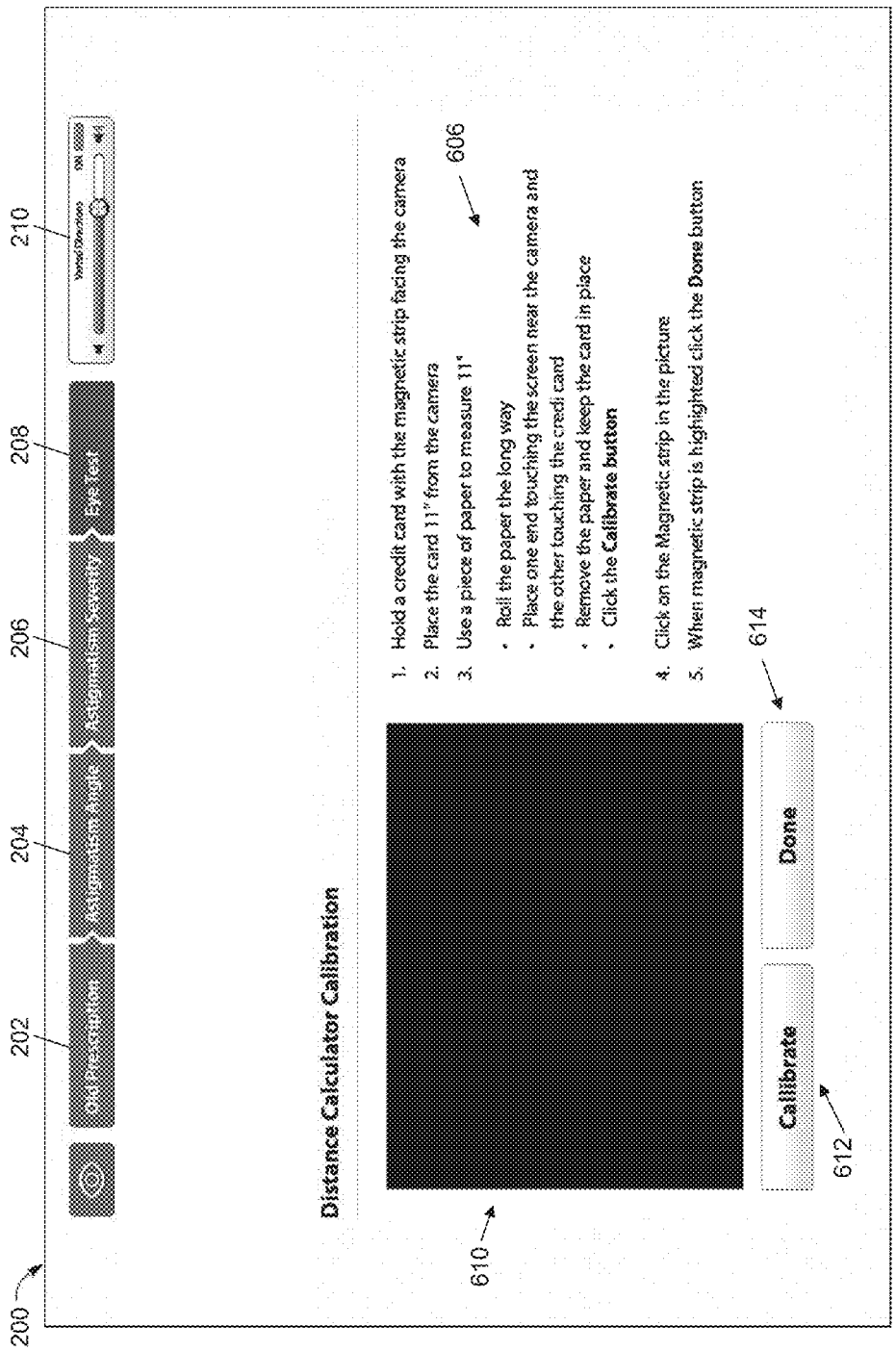
FIG. 6 illustrates a screen shot of an example of an embodiment of the system of the present disclosure, wherein the system calibrates the amount of distance between a camera mounted to the computerized screen and the patient.

Referring now to the embodiment illustrated in FIG. 6, another example embodiment of the present disclosure is illustrated. At this stage of the process, the system presents display 200, and the progress bar indicates that the patient is currently in the Eye Test section 206. Specifically, the display 200 in FIG. 6 is directed to calibrating a camera which may be attached to the computerized screen to determine the distance of the patient from the computerized screen. The system must know the distance of the patient in order to accurately calculate the sphere measurements from the eye tests. If the patient's computerized screen does not have a camera, the system will provide the patient a specified distance to remain away from the screen. This distance may be the same or different for each instance of the "small-to-large" eye test (described at blocks 122 and 124 of FIG. 1A) and/or each instance of the "large-to-small" eye test (described at blocks 126 and 128 of FIG. 1A).

The written instructions 606 of the example embodiment illustrated by FIG. 6 read: "1. Hold a credit card with the magnetic strip facing the camera. 2. Place the card 11" from the camera. 3. Use a piece of paper to measure 11". Roll the paper the long way. Place one end touching the screen near the camera and the other touching the credit card. Remove the paper and keep the card in place. Click the Calibrate button. 4. Click on the magnetic strip in the picture. 5. When magnetic strip is highlighted click the Done button." Camera viewer 610 shows the patient what the camera is viewing. The patient can follow the instructions to click the Calibrate button 612 and the Done button 614 in accordance with the written instructions. It should be appreciated that any other suitable or conventional method of calibrating the distance between the patient and the computerized screen may be employed.

It should be appreciated that any suitable distance between the patient and the screen may be used. In one embodiment, the distance between the patient and the screen is determined based on whether the patient is nearsighted or farsighted. In a further embodiment, the system determines that the distance between the patient and the screen is the same for a nearsighted patient and a farsighted patient. In another embodiment, the system determines that the distances between the patient and the screen are different for a nearsighted patient and a farsighted patient. In one embodiment, the system may determine the distance between the patient and the screen depending on the kind, type, dimensions, or other characteristics of the screen. In another embodiment, the patient may be enabled to make an input regarding whether the determined input is difficult for the patient to use. In a further embodiment, the system may determine a new distance between the patient and the screen after the patient makes an input regarding whether the determined input is difficult for the patient to use.

In another example embodiment, they system or patient terminal may utilize mirrors to simulate the a greater or lesser distance between the patient and the computerized screen, such as is conventional in projection technology, or in, for example, a optometrist's office. In a further example embodiment, the mirrors are adjustable based on the location of the patient, such that the patient may move and the mirrors may adjust to account for the movement to maintain the same simulated distance.

In another example embodiment, the system determines a focal distance for patient, which may then be used for various tests, such as astigmatism cylinder determination tests. As discussed in the Background section, astigmatism is a refractive error of the eye that causes light entering the eye to focus on two points in or around the retina of a patient, rather than one. Patients with astigmatism may have any of the following combinations of focal points for one or both eyes: in front of the retina and behind the retina; in front of the retina and on the retina; on the retina and behind the retina; two points in front of the retina separated by a finite distance; or two points behind the retina separated by a finite distance. These focal points in and around the patient's retina correlate to distances in real space. Therefore, a patient with astigmatism can relocate themselves nearer to or further from an object until their view of that object is approximately in focus, despite the astigmatism. That location (where the viewed object is approximately in focus) is the real space location corresponding to one of the patient's two focal distances.

Applicants have surprisingly found that, when patients that view digital screens containing images oriented at the patient's axis of astigmatism where the patient is located remote from the digital screen at one of their focal distances, this enables the system to isolate the refractive errors related to astigmatism from the refractive errors related to sphere, providing a more accurate cylinder determination than when at a known, but non-focal distance, location from the digital screen.

In one such example embodiment, the system instructs the patient to move away from the digital screen until they cannot see the details of the object, image, or figure displayed on the digital screen. The displayed object, image, or figure may be displayed at any suitable orientation, such as at the patient's astigmatism axis as was previously determined by the system or as was gleaned from a previous prescription of a patient. The system enables the patient to make an input indicating that they cannot see the displayed object, image, or figure, then instructs the patient to move towards the screen in small increments until they can just make out the details of the displayed object, image, or figure. By way of example only, if the displayed image is a capital letter "E," the system may instruct the patient to move towards the screen in small increments until they can make out the direction in which the tines of the "E" are pointing (left, right, up, down, etc.). The system enables a user to make at least one input indicating that they can just make out the details of the displayed object, image, or figure. The distance of the patient from the screen when they can just make out the details of the object, image, or figure is one of the patient's focal distances. In this example embodiment, the system conducts the remainder of the cylinder determination with the patient at this determined focal distance locations.

In another embodiment, the system instructs the patient to move a known, fixed distance from the digital screen displaying the testing images for the duration of certain of the tests described herein, such as the astigmatism cylinder tests, the astigmatism axis tests, or any other suitable test. The known, fixed distance may be any suitable distance, so long as the distance is known, input by the patient, or calculable at some time before, during, or after the patient undergoes the cylinder determination tests. In one example embodiment, the known, fixed distance is 10 feet. In another example embodiment, the known, fixed distance is 6 feet. In an example embodiment wherein the patient is located a known, fixed distance from the digital screen displaying testing images, the specific testing being conducted would proceed under the direction of the system as described in detail elsewhere in this disclosure.

In an additional example embodiment, the system may query the patient for their shoe size and gender and, using that information, have the patient estimate their distance from the computerized screen via heel-to-toe measurement and enter that distance into the system. In an alternative example embodiment, the system may instruct the patient to take a determined number of heel-to-toe steps from the computerized screen, placing the patient at a fairly accurate distance from the computerized screen.

In another example embodiment, the system utilizes an input from an external source that can triangulate and measure the distance of an individual in real time from that of a monitor, as is known in the art. Example systems include X-Box Kinect®, which has a distance monitoring function utilizing a depth sensor combining an infrared laser projector and a monochrome CMOS sensor, which captures video data in 3D under any ambient light conditions. This external source input is then utilized, either in whole or in part, to measure the distance between the patient and the computerized screen, to perform a validation check of the distance a patient believes he or she is at (input by the patient or based on system instructions to the patient to move to a certain distance), or to verify measurements in kiosk-based structures or systems (as described further herein).

Figure 7A:
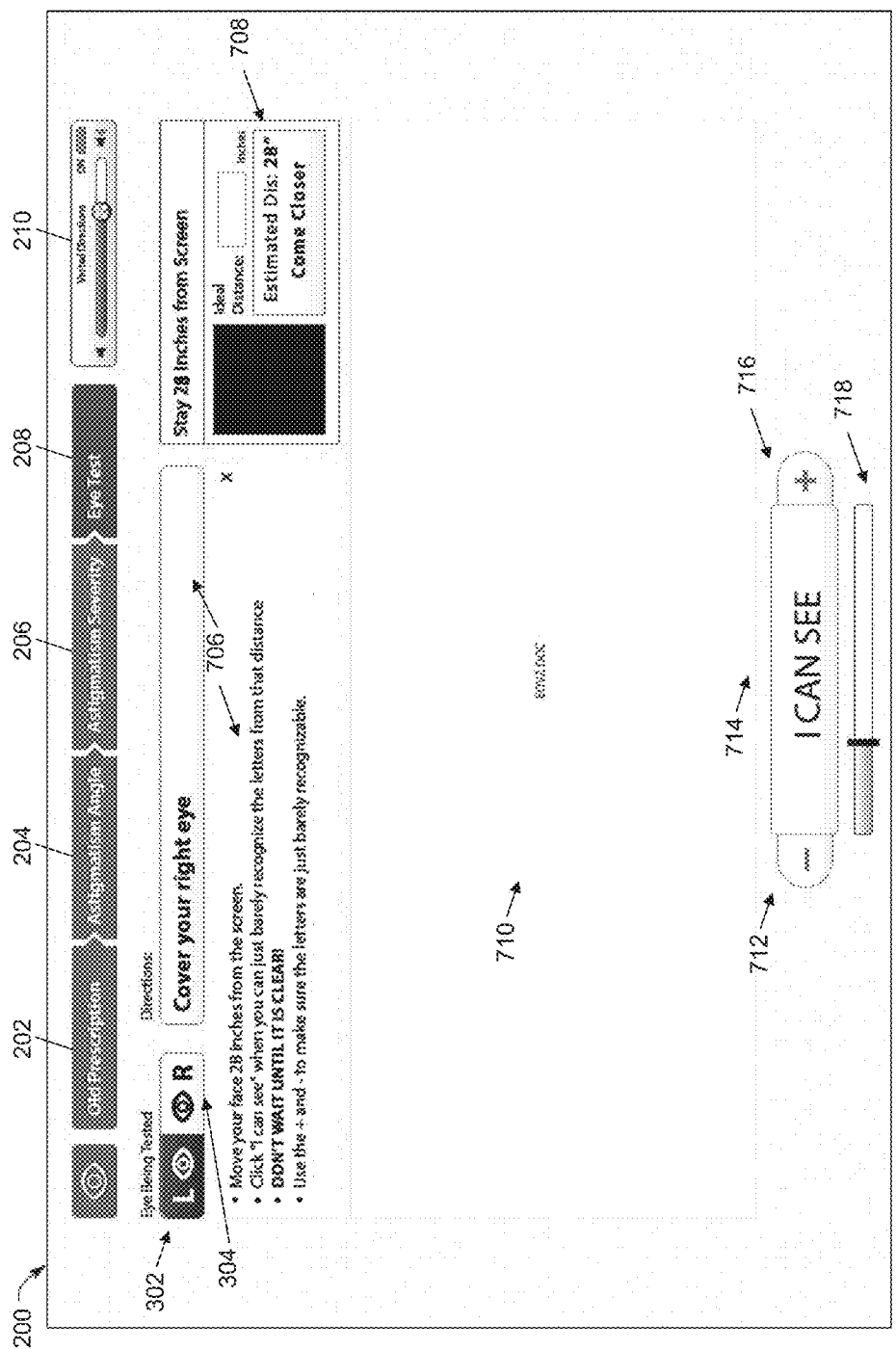
FIGS. 7A and 7B illustrate screen shots of examples of an embodiment of the system of the present disclosure, wherein the system displays a figure and enables a patient to make at least one input to change the size of the figure, wherein the at least on input corresponds to a sphere measurement of the patient.

Referring now to the embodiment illustrated in FIG. 7A, another embodiment of the present disclosure is illustrated. At this stage of the process, the system presents display 200, and the progress bar indicates that the patient is currently in the Eye Test section 206. The eye tracker 302, 304 indicates that the left eye 302 is being tested. For systems with cameras, the system provides a calibration box 708 with an estimate of the distance of the patient from the camera/computerized screen. In one embodiment, the system uses the camera-measured distance of the patient from the screen to determine a font size or an icon size to display to the patient as part of FIG. 710.

Figure 7B:
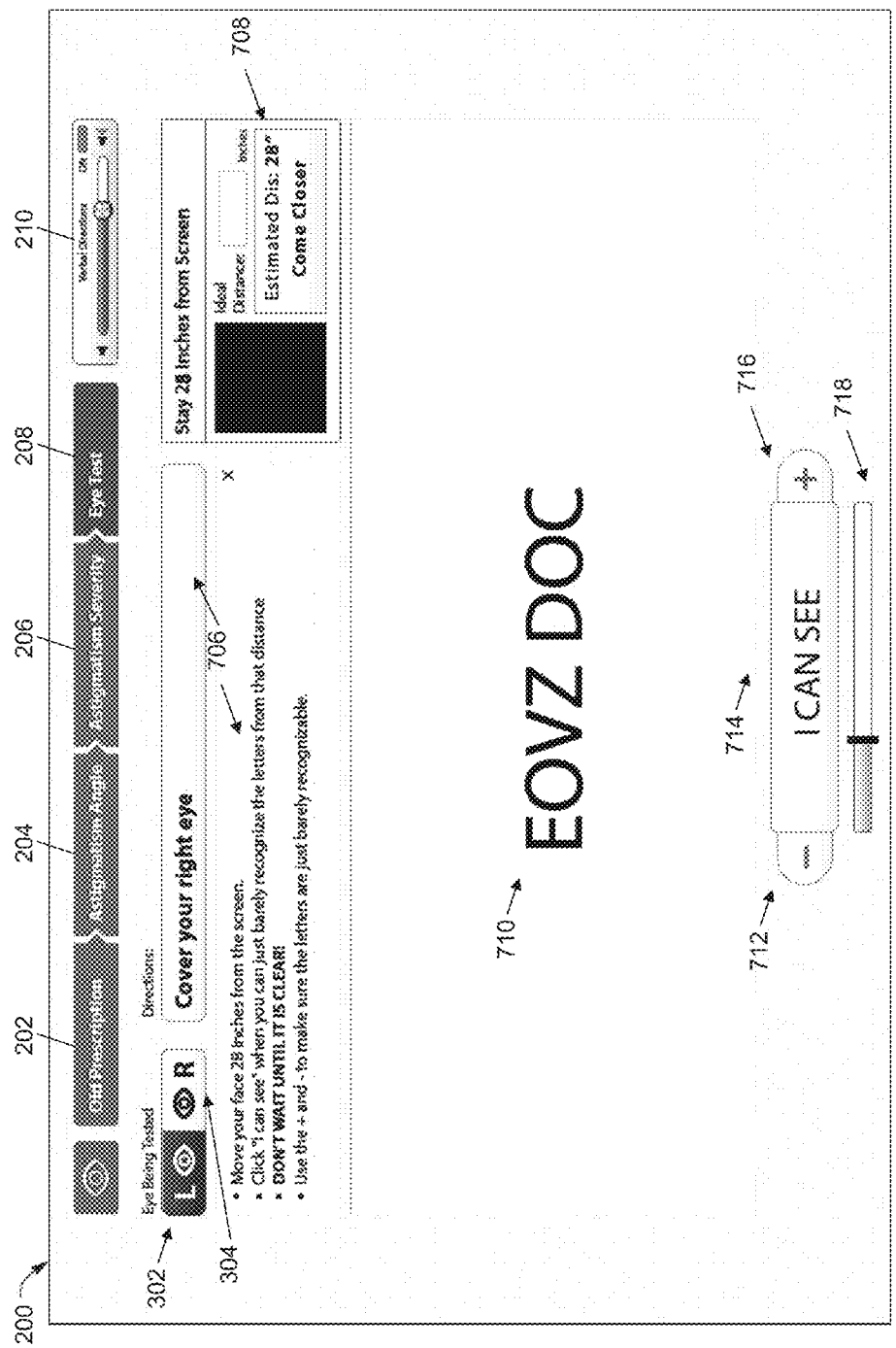
Figure 8A:
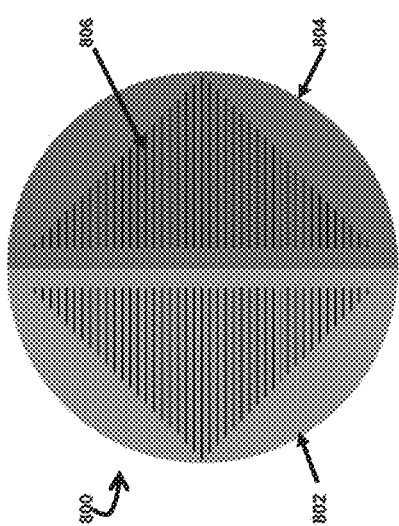
FIGS. 8A, 8B, 8C, and 8D illustrate screen shots of examples of an embodiment of the system of the present disclosure, wherein the system displays a colorblocked diagram and enables a patient to make at least one input to select a more defined-appearing part of the diagram, wherein the input corresponds to a determination that the patient is near or far sighted (if not wearing corrective lenses), over or under corrected (if wearing corrective lenses), or otherwise.
Figure 8B:
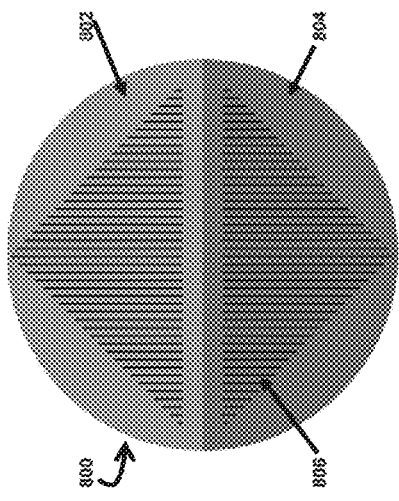
Figure 8C:
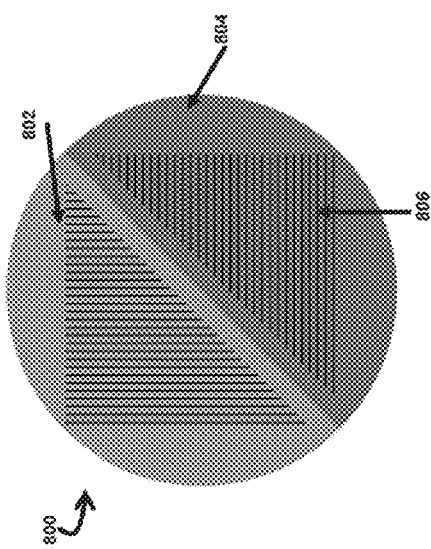
Figure 8D:
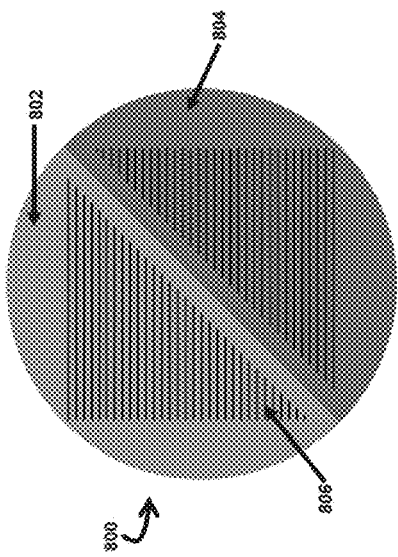

The written instructions 706 read: "Cover your right eye. Move your face 28 inches from the screen. Click "I can see" when you can just barely recognize the letters from that distance. DON'T WAIT UNTIL IT IS CLEAR! Use the + and − to make sure the letters are just barely recognizable." The written instructions refer to FIG. 710, which in this embodiment is a series of letters. It should be appreciated that any suitable kind or number of visual cues, symbols, shapes, or icons can make up the FIG. 710, such as letters, numbers, pictures, or the like. As shown in FIG. 7A, the system provides patient-selectable icons 712 and 716 to adjust the figure until the patient views the figure as just barely being able to make out the letters of the figure. When the patient views the figure and can just barely make out the letters, the patient selects the patient-selectable icon 414. In one embodiment, the FIG. 710 starts small enough that the figures cannot be clearly seen by the patient, and the patient must make at least one input to increase the size of the figure until it can just barely be made out. In another embodiment, shown in FIG. 7B, the figure starts large enough to be clearly seen by the patient, and the patient must make at least one input to decrease the size of the figure just until the figure can no longer be made out.

The system determines a sphere measurement from at least one input from a "small-to-large" eye test. The system determines another sphere measurement from at least one input of a "large-to-small" eye test. As discussed previously, the "small-to-large" eye test and the "large-to-small" eye test may be performed any number of times, in any order, for each eye, with each eye test resulting in a sphere measurement determined from the at least one input of the patient. In one embodiment, the system may perform only the "small-to large" eye test, and not the "large-to small" eye test. In another embodiment, the system may perform only the "large-to small" eye test, and not the "small-to large" eye test. Either or both eye tests may be performed one or more times per eye of the patient. When the system has provided all instances of the eye test to both eyes, the system averages the sphere measurements from the eye test instances to determine a final sphere measurement. It should be appreciated that the system may determine not to use a given sphere measurement in the final sphere measurement if it is a statistically significant unit of measurement away from the average of the remaining resultant sphere measurements. In one embodiment, the system takes the mean of the resultant sphere measurements as the final sphere measurement.

It should be appreciated that the system may adjust the size of the figure in any suitable way, at any suitable speed, and at any suitable increment. In one embodiment, the system automatically increases (for the "small-to-large" test) or decreases (for the "large-to-small" test) the figure prior to enabling the patient to make an input. In another embodiment, the system automatically begins increasing or decreasing the figure, and continues to increase or decrease the figure until the patient makes an input to stop the increasing or decreasing. In a further embodiment, the patient may further adjust the size of the figure by making at least one input. In another further embodiment, the patient may not further adjust the size of the figure by making any inputs. In another embodiment, the system does not increase or decrease the figure prior to receiving at least one input from the patient.

It should be appreciated that the above-described embodiments of the present disclosure may be implemented in accordance with or in conjunction with one or more of a variety of different types of systems, such as, but not limited to, those described below.

Referring now to FIGS. 8A, 8B, 8C and 8D, another embodiment of the present disclosure is illustrated, wherein the system displays at least one colorblocked diagram 800 and enables a patient to make at least one input to select a more defined-appearing part of the diagram, wherein the input corresponds to a determination that the patient is near or far sighted (if not wearing corrective lenses), over or under corrected (if wearing corrective lenses), or otherwise. The colorblocked diagram 800 may be presented once, twice, or more in a series, for each eye. The colorblocked diagram 800 may be the same or slightly different for each presentation to the patient. In the examples shown in FIGS. 8A, 8B, 8C, and 8D, the colorblocked diagrams 800 are slightly different.

The colorblocked diagram 800 has at least two parts, shown as part 802 and part 804. In the embodiment shown in FIGS. 8A-D, parts 802 and 804 are semicircles having a background color. In the examples shown in FIGS. 8A-D, part 802 has a brighter background color, while part 804 has a duller background color. It should be appreciated by one of skill in the art that any suitable brighter and duller colors, may be used as the background color of parts 802 and 804, respectively. In one embodiment, part 802 has a background from the green family of colors (including the various colors of green from dark to light, bright to dark, and mixed with other colors, i.e. yellow-green or blue-green), while part 804 has a background from the red family of colors (including the various colors of red from dark to light, bright to dark, and mixed with other colors, i.e. purple-red or red-orange). In another embodiment, part 802 has a background from the yellow family, while part 804 has a background from the purple family.

Parts 802 and 804 further include a plurality of lines of various lengths 806 that, when placed closed together and viewed from a short distance, appear as an arrowhead shape. In each of FIGS. 8A-D, the arrow directions face away from each other, and are comprised of horizontal or vertical lines 806. It should be appreciated by one of skill in the art that any suitable number of lines (straight or curved, in any suitable density), arranged into any suitable direction, making up any suitable aggregate shape may be used. In another further embodiment, the lengths 806 may be replaced by solid or semi-solid shapes, such as circles, squares, triangles, letters, numbers etc. It should further be appreciated that parts 802 and 804 may be shapes other than semicircles, such as half squares, half triangles, etc.

As discussed above, the colorblocked diagram 800, in one or more of its configurations, may be used to determine whether a patient is near or far sighted if not wearing corrective lenses. The system may instruct the patient to remove any corrective lenses, such as glasses or contacts, before using the system. The system presents a colorblocked diagram to one eye of the patient, and enables the patient to make an input regarding which of the arrow parts appears more distinct to their uncorrected eye. In one embodiment, the patient may select that part 802 with the brighter background looks more distinct (i.e. sharper or more defined), that part 804 with the duller background looks more distinct, or that the arrows on parts 802 and 804 are about equally distinct. In general, a selection that part 802 with the brighter background is more distinct than part 804 with the duller background suggests that the patient is farsighted. In general, a selection that part 804 with the duller background is more distinct than part 802 with the brighter background suggests that the patient is nearsighted. It should be appreciated by one of skill in the art that performing two or more tests per eye with colorblocked diagrams having arrows pointing in different directions will assist in mitigating any subjective error from the patient. In an embodiment, the patient is presented with FIGS. 8A to 8D in any order, for their first eye, than 8A to 8D, in any order, for their second eye. The system uses the results of the one, two, three, four, or more colorblocked diagram tests to determine the near or far sightedness of the patient.

It should be appreciated that the tests shown by example in FIGS. 8A to 8D may also be used to determine if a patient is over or under corrected if performed while wearing corrective lenses. In one example embodiment, the patient performs the same steps described immediately above, individually for each eye, while using their corrective lenses. In this example embodiment, a selection that part 802 with the brighter background is more distinct than part 804 with the duller background suggests that the patient is overcorrected with their present corrective lenses, while a selection that part 804 with the duller background is more distinct than part 802 with the brighter background suggests that the patient is under corrected by their present corrective lenses.

Figure 9A:
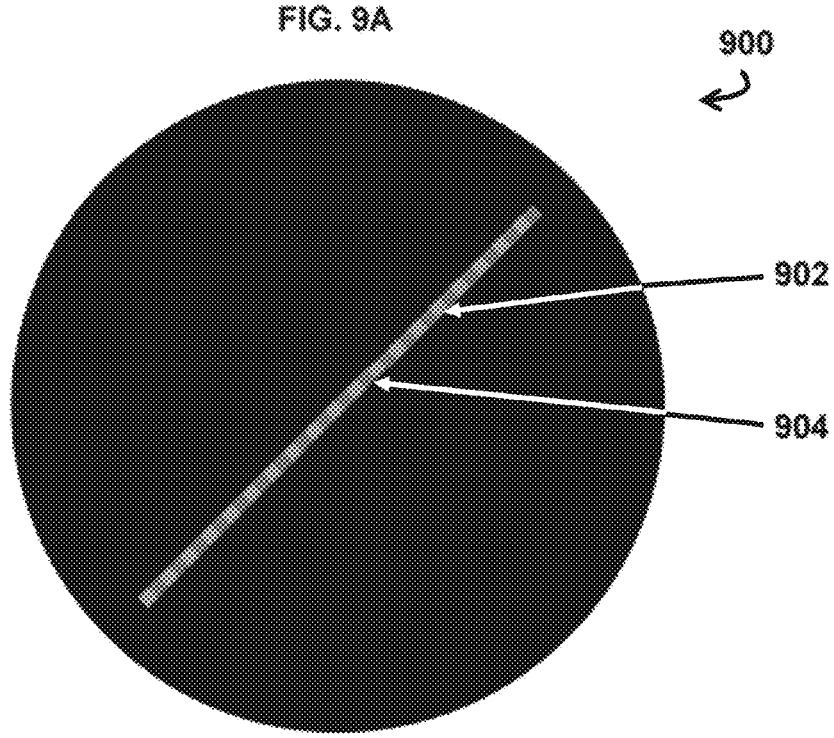
FIG. 9A illustrates a screen shot of an example of an embodiment of the system of the present disclosure, wherein the system displays a figure and enables a patient to make at least one input to affect the rotation of the figure, wherein the at least one input corresponds to an axis measurement.

Referring now to FIG. 9A, another embodiment of the present disclosure is illustrated. FIG. 9A is a screen shot of an example of an embodiment of the system of the present disclosure, wherein the system displays a line diagram 900 and enables a patient to make at least one input to affect the rotation of the line diagram, wherein the at least one input corresponds to an axis measurement. In the example embodiment shown in FIG. 9A, the line diagram 900 is a line, or a long thin rectangle on a solid background. The rectangle/line is made up of alternating parts 902 and 904. Alternating parts 902 and 904 are different colors. In the embodiment of FIG. 9A, part 902 has a brighter background color, while part 904 has a duller background color. It should be appreciated by one of skill in the art that any suitable brighter and duller colors, may be used as the background color of parts 902 and 904, respectively. In one embodiment, part 902 has a background from the green family of colors (including the various colors of green from dark to light, bright to dark, and mixed with other colors, i.e. yellow-green or blue-green), while part 904 has a background from the red family of colors (including the various colors of red from dark to light, bright to dark, and mixed with other colors, i.e. purple-red or red-orange). In another embodiment, part 902 has a background from the yellow family, while part 904 has a background from the purple family.

The alternating parts 902 and 904 may be any suitable shape or size. For example, in FIG. 9A, the alternating parts 902 and 904 are squares which make up the rectangle/line of line diagram 900, without any space between the parts. It should be appreciated by one of skill in the art that two or more alternating parts may be used.

The system presents the line diagram 900 to the patient. In one embodiment, the system begins rotating the diagram 900 about its center. In another embodiment, the patient makes an input to begin rotation of the diagram 900 about its center. The rotation is slow enough that the patient can identify changes. In one embodiment, the patient may make an input to speed up or slow down the rotation of the diagram 900. In another embodiment, the diagram 900 does not rotate automatically, and the patient must make an input corresponding to each rotation of the diagram 900.

The applicant has surprisingly found that use of a line diagram, such as line diagram 900, can be used to determine the axis prescription of a patient to within 1° of accuracy. Because the effect of an astigmatism is to distort, or stretch, a patient's vision along an axis, when the line diagram 900 is near or at the patient's axis of astigmatism, the alternating parts 902 and 904 will blur together and appear as a different color than either of the parts individually. In one example embodiment where part 902 is green and part 904 is red, the line appears yellow at or near the axis of the patient's astigmatism. It should be appreciated by one of skill in the art that if the patient does not have an astigmatism, the line will not appear to change color.

The rotational axis of the line diagram 900 is composed of angles ranging from 0 degrees to 360 degrees. However, in an optical prescription, angles are written in 0 degrees to 180 degrees. Thus, one of skill in the art will appreciated that angles 0° and 180° are the same, 170° and 350° are the same, 100° and 280° are the same and so on and so forth. The axis line extends below the 180° point, and that is why angles above 180° also have a corresponding equivalence below 180°.

In an embodiment of they system of the present disclosure, the system presents the patient with the line diagram 900, which may rotate by system or patient direction, as described above. The patient viewing the diagram with one corrected eye at a time, is enabled to make an input corresponding to when they see the line appear to change color. In one embodiment, the patient is prevented from making an input that the line did not change color until at least one or more full rotations of the line have been completed. In another embodiment, once a patient makes an input indicating that the line appeared to change color, the patient is enabled to make further fine-tuning inputs causing small rotations to the line until the patient makes another input corresponding to the angle at which the changed color appears most distinctly (i.e. strongest, darkest, or most clear). In one embodiment, the fine-tuning inputs cause a rotation of 1°. It should be appreciated by one of skill in the art that other fine-tuning increments can be used, such as 2°, 5°, or 10°. Since conventional subjective axis determination techniques use increments of 10°, and since an astigmatism can be along any axis (at any degree), any increment less than 10° should yield a more accurate determination than the phoropter system used by eye care professionals in-office. The angle selected by the input corresponding to the angle at which the changed color appears most distinctly is the axis prescription of the patient. The system then repeats the process for the other uncorrected eye of the patient.

In an embodiment, the system enables the patient to make an input reflecting that the line did not appear to change color. It should be appreciated by one of skill in the art that such an input would suggest that the patient does not have an astigmatism in that eye. In a further embodiment, the system gives the patient an additional axis test for that eye, such as that described in FIG. 3. In a different further embodiment, the system permits the patient to skip the cylinder test, and go right to an axis test for the other eye, or another kind of test, such as the power test.

Figure 9B:
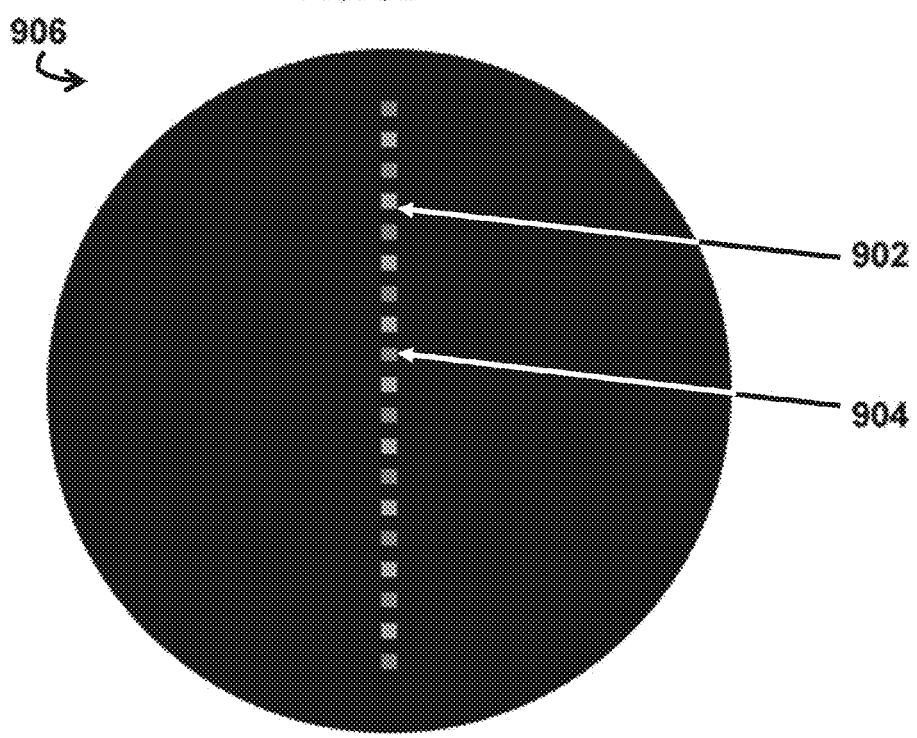
FIG. 9B illustrates a screen shot of an example of an embodiment of the system of the present disclosure, wherein the system displays a figure and enables a patient to make at least one input to affect the spacing or size of various parts of the figure, wherein the at least one input corresponds to an cylinder measurement.

Referring now to FIG. 9B, another embodiment of the present disclosure is illustrated. FIG. 9B is a screen shot of an example of an embodiment of the system of the present disclosure, wherein the system displays a line diagram 906 and enables a patient to make at least one input to affect the spacing or size of various parts of the line diagram 906, wherein the at least one input corresponds to an cylinder measurement.

The applicant has surprisingly found that use of a line diagram, such as line diagram 906, can be used to accurately determine the cylinder prescription of a patient. Because the effect of an astigmatism is to distort, or stretch, a patient's vision along an axis, when the alternating parts are stretched to correspond to the severity of the patient's astigmatism, the patient's eye will once again be able to resolve the alternating parts in their actual colors. It should be appreciated by one of skill in the art that if the patient does not have an astigmatism, the line will only appear with the alternating parts in their actual colors.

The line diagram 906 shown in the example embodiment of FIG. 9B is different from FIG. 9A in that it is used to determine the severity of astigmatism for a patient. If it was previously determined that the patient has an axis of astigmatism, this is the next test to determine how much astigmatism that individual has. Line diagram 906 is first shown in the angle of astigmatism that was determined in the axis determination test described with reference to FIG. 9A, and has alternating parts 902 and 904, similar to those described above with reference to FIG. 9A. As confirmed previously during the test described with reference to FIG. 9A, the line diagram 906 should appear as a different color than the alternating parts 902 and 904. In the example where alternating parts 902 and 904 are green and red, respectively, the line diagram 906 at the axis of astigmatism for the patient being tested should appear yellow to the patient.

The system presents the line diagram 906 to one uncorrected eye of a patient at a time. In one embodiment, the system automatically increases the size (i.e. length and/or width) of the alternating parts 902 and 904 until the patient makes an input indicating that they can see the colors of the alternating parts again. The patient is enabled to make fine-tuning inputs to change the size of the alternating parts until the size where they can first see the alternating colors. In an embodiment where line diagram 906 first appears yellow to a patient even though parts 902 and 904 are green and red, respectively, the patient would make an input when they begin to see the green and red parts 902 and 904 again. In another embodiment, the system does not automatically change the size of the alternating parts, and enables the patient to make inputs corresponding to all size changes.

In another embodiment, the system begins by inserting space between the alternating parts 902 and 904 until the patient makes an input indicating that they can see the colors of the alternating parts again. The patient is enabled to make fine-tuning inputs to change the spacing of the alternating parts until the size where they can first see the alternating colors. In another embodiment, the system does not automatically change the spacing of the alternating parts, and enables the patient to make inputs corresponding to all spacing changes.

It should be appreciated by one of skill in the art that the size and spacing changes can be made in the same test, at the same time, or sequentially in any order. In one example embodiment, the size of the alternating parts 902 and 904 changes until the patient make an input, at which point the system enables the patient to make fine-tuning inputs affecting the size, spacing, or both of the alternating parts. In another example embodiment, the spacing of the alternating parts 902 and 904 changes until the patient make an input, at which point the system enables the patient to make fine-tuning inputs affecting the spacing, size, or both of the alternating parts. The system determines the astigmatism severity, or cylinder prescription of the patient from the final size and/or spacing of the alternating parts. The system then repeats the process for the other uncorrected eye of the patient.

Figure 10A:
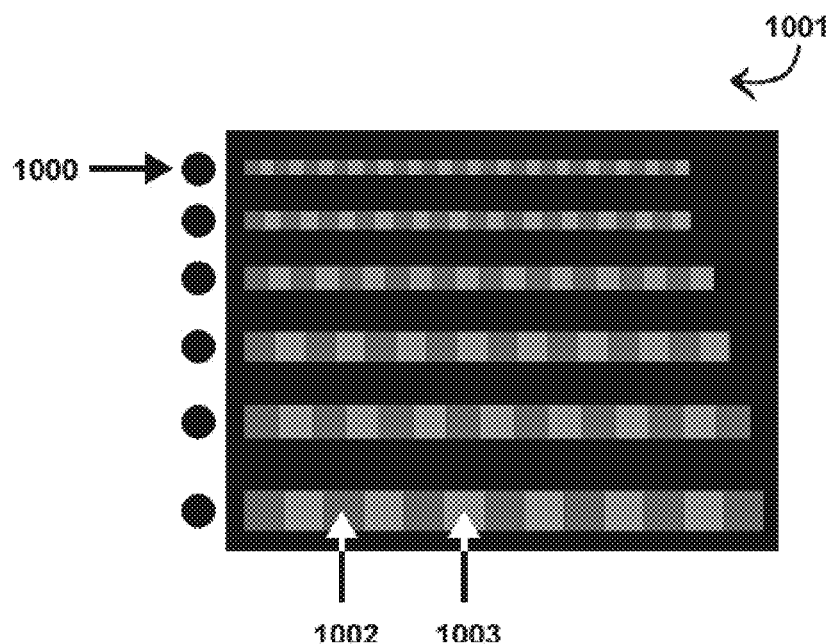
FIG. 10A illustrates a screen shot of an example of an embodiment of the system of the present disclosure, wherein the system displays wherein the system displays a line diagram and enables a patient to make at least one input, wherein the at least one input corresponds to a cylinder measurement.
Figure 10B:
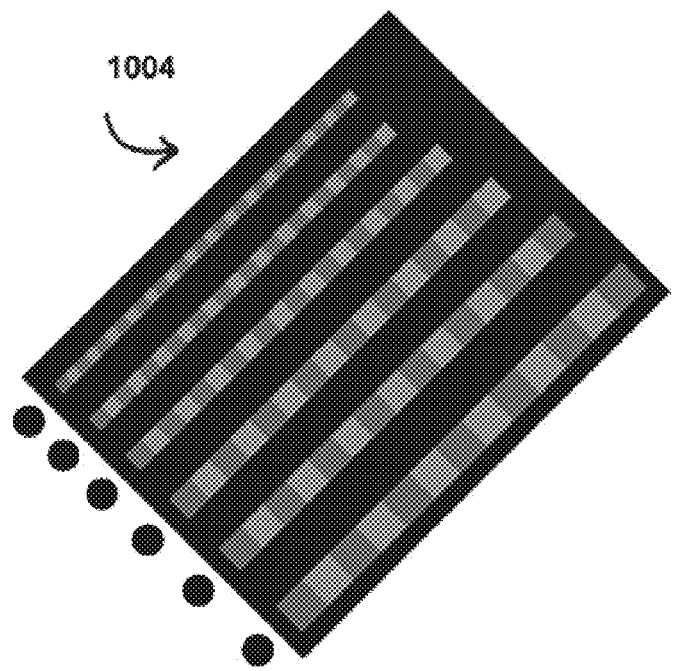
FIG. 10B illustrates a screen shot of an example of an embodiment of the system of the present disclosure, wherein the figure of 10A is rotatable to align with the determined axis of a patient's astigmatism.

Referring now to FIGS. 10A and 10B, another embodiment of the present disclosure is illustrated. FIG. 10A is a screen shot of an example of an embodiment of the system of the present disclosure, wherein the system displays a line diagram 1101 and enables a patient to make at least one input, wherein the at least one input corresponds to a cylinder measurement. FIG. 10B is a screen shot of an example of an embodiment of the system of the present disclosure wherein the figure of 10A is rotatable to align with the determined axis of a patient's astigmatism.

In the example embodiment shown in FIGS. 10A and 10B, the line diagram 1001/1004 is a series of lines, or long thin rectangles on a solid background. The series of lines includes lines of different sizes. In the example embodiment shown in FIG. 10A, the lines increase in size as they are view from the top of diagram 1001 to the bottom of diagram 1001. The rectangles/lines are made up of alternating parts 1002 and 1003. Alternating parts 1002 and 1003 are different colors, one brighter and the other duller, similar to the alternating parts 902 and 904 discussed above. In the embodiment of FIG. 10A, part 1003 has a brighter background color, while part 1002 has a duller background color.

It should be appreciated by one of skill in the art that the size of the lines or alternating parts, and the spacing between the lines or the alternating parts may be any suitable amount. For example, FIGS. 10A and 10B show the lines separated by space, but the alternating parts of each line are immediately adjacent. In another example embodiment, the alternating parts may have space between them and the lines may be immediately adjacent.

The system presents the line diagram 1001 or 1104 to one uncorrected eye of a patient at a time. The patient is enabled to make at least one input to select one or more lines that appear different in color from the remaining lines. In one example embodiment where part 1003 is green and part 1002 is red, a line of alternating parts appears yellow below the cylinder, or astigmatism severity of the patient's astigmatism. The selection may be accomplished in any suitable manner, such as by selecting and clicking a line, or a button representing a line, such as buttons 1000.

The applicant has surprisingly found that use of a line diagram, such as line diagrams 1001 and 1004, can be used to accurately determine the cylinder prescription of a patient. Because the effect of an astigmatism is to distort, or stretch, a patient's vision along an axis, when the alternating parts are stretched to correspond to the severity of the patient's astigmatism, the patient's eye will once again be able to resolve the alternating parts in their actual colors. It should be appreciated by one of skill in the art that if the patient does not have an astigmatism, the lines will only appear with the alternating parts in their actual colors.

Figure 11A:
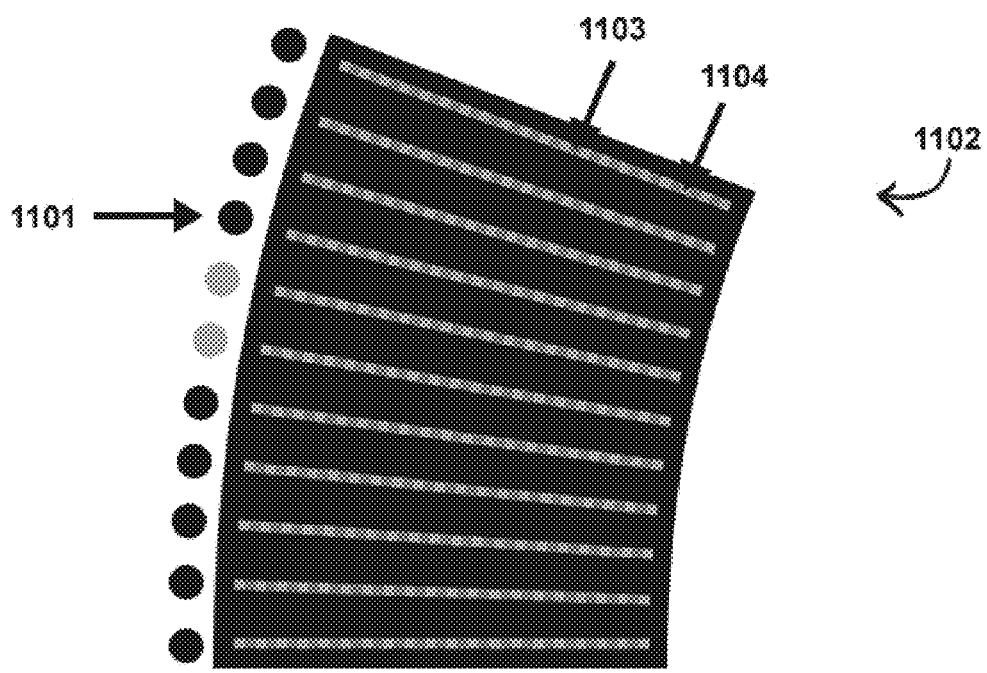
FIG. 11A illustrates a screen shot of an example of an embodiment of the system of the present disclosure, wherein the system displays fine spoke diagram, which is a smaller angular portion of spoke diagram of FIG. 12B, and enables a patient to make at least one input, wherein the at least one input corresponds to a fine axis measurement.
Figure 11B:
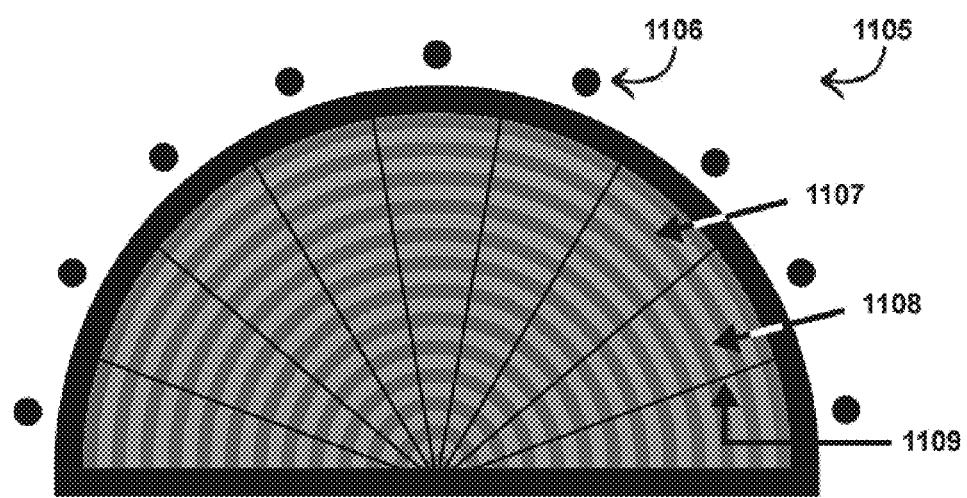
FIG. 11B illustrates a screen shot of an example of an embodiment of the system of the present disclosure, wherein the system displays a concentric semi-circle diagram 1105 and enables a patient to make at least one input, wherein the at least one input corresponds to an axis and/or a cylinder measurement.

Referring now to FIG. 11B, another embodiment of the present disclosure is illustrated. FIG. 11B is a screen shot of an example of an embodiment of the system of the present disclosure, wherein the system displays a concentric semi-circle diagram 1105 and enables a patient to make at least one input, wherein the at least one input corresponds to an axis and/or a cylinder measurement.

In the example embodiment shown in FIG. 11B, the semi-circle diagram 1105 is a half-circle on a solid background. The half-circle is made up of alternating parts 1107 and 1108, arranged into concentric half-circles. Alternating parts 1107 and 1108 are different colors, one brighter and the other duller, similar to the alternating parts 902 and 904 discussed above. In the embodiment of FIG. 11B, part 1108 has a brighter background color, while part 1107 has a duller background color.

The alternating parts 1107 and 1108 may be any suitable shape or size, with any suitable spacing between them. For example, in FIG. 11B, the alternating parts 1107 and 1108 are concentric curved rectangular slices which make up the semi-circle of diagram 1105, without any space between the parts. It should be appreciated by one of skill in the art that two or more alternating parts may be used. In the example embodiment of FIG. 11B, the semi-circle diagram 1105 is divided into wedges by radii lines 1009. It should be appreciated that radii lines can be placed at any suitable angular distance from each other, such as at 1, 2, 5, 10, or 30 degrees, or at other degree increments. It is preferable that the angular distance be evenly divisible into 180 degrees. As shown in FIG. 11B, the radii lines 1009 are placed 20 degrees apart.

The system presents the semi-circle diagram 1105 to one uncorrected eye of a patient at a time. The patient is enabled to make at least one input to select one or more wedges that looks different in color from the remaining wedges. The selection may be accomplished in any suitable manner, such as by selecting and clicking a wedge, or a button representing a wedge, such as buttons 1106.

The applicant has surprisingly found that use of a semi-circle diagram, such as semi-circle diagram 1105, can be used to determine the axis prescription of a patient. Because the effect of an astigmatism is to distort, or stretch, a patient's vision along an axis, at the portion of the semi-circle diagram nearby to the patient's axis of astigmatism, the alternating parts 1107 and 1108 will blur together and appear as a different color than either of the parts individually. In one example embodiment where part 1108 is green and part 1107 is red, a portion of a wedge appears yellow at or near the axis of the patient's astigmatism. It should be appreciated by one of skill I the art that a greater blurring of the colors away from the center of the circle diagram, indicates a more severe astigmatism cylinder measurement. It should be appreciated by one of skill in the art that if the patient does not have an astigmatism, none of the portions of the wedges will appear to change color.

Figure 12A:
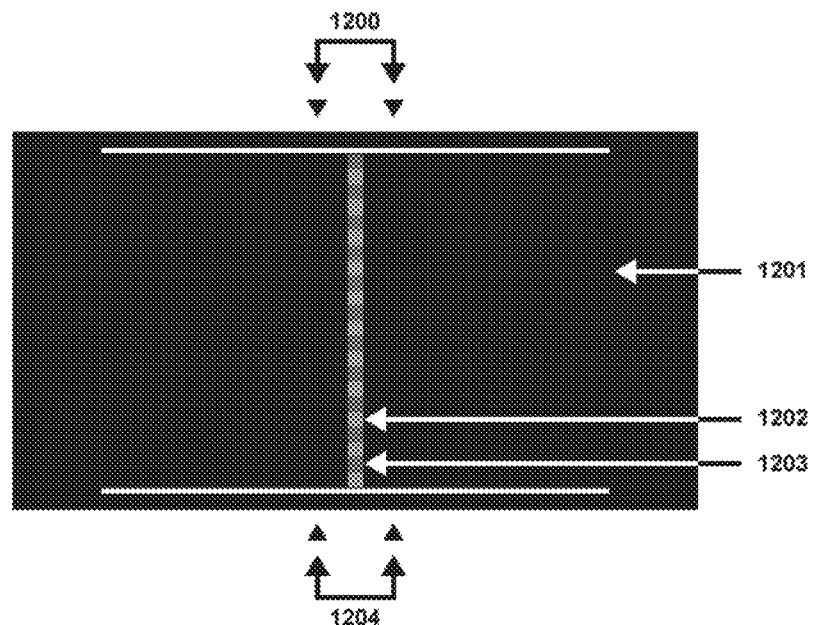
FIG. 12A illustrates a screen shot of an example of an embodiment of the system of the present disclosure, wherein the system displays line diagram, and enables a patient to make at least two inputs, wherein the at least two inputs correspond to a cylinder measurement.
Figure 12B:
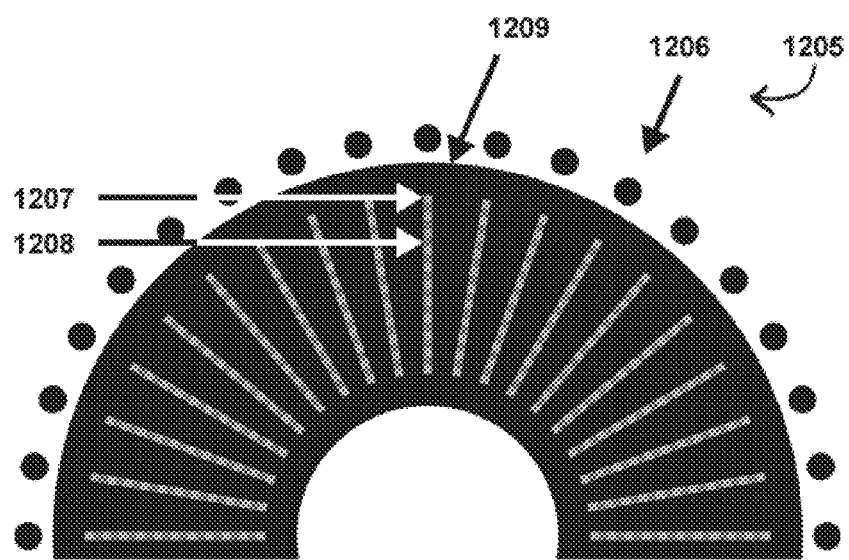
FIG. 12B illustrates a screen shot of an example of an embodiment of the system of the present disclosure, wherein the system displays a spoke diagram 1205 and enables a patient to make at least one input, wherein the at least one input corresponds to a gross axis measurement.
Figure 14A:
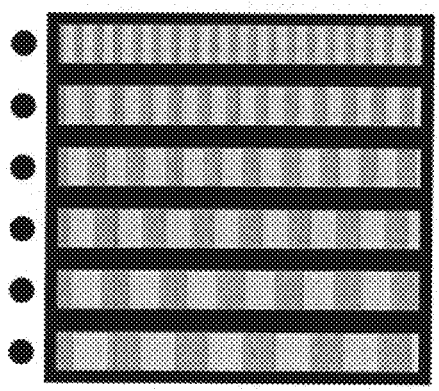
FIGS. 14A-D are screen shots of example embodiments of the system of the present disclosure which demonstrate that the alternating parts may be of different sizes or spacing, but still test for the same determination in the astigmatism severity determination.
Figure 14B:
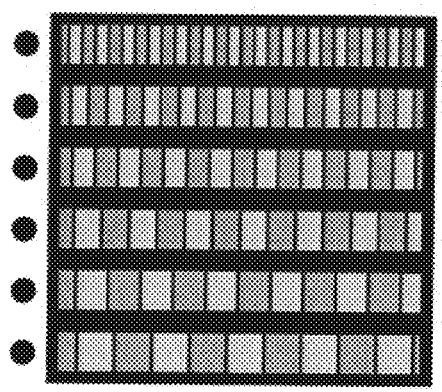
Figure 14C:
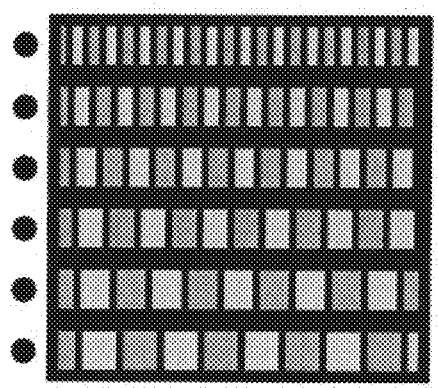
Figure 14D:
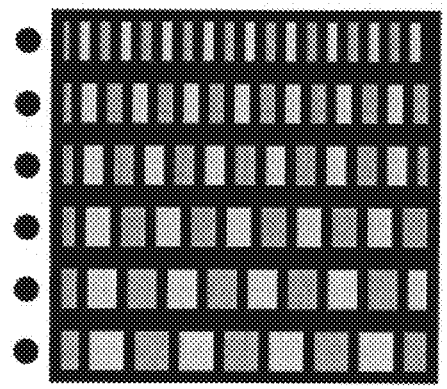

Referring now to FIG. 12B, another embodiment of the present disclosure is illustrated. FIG. 12B is a screen shot of an example of an embodiment of the system of the present disclosure, wherein the system displays a spoke diagram 1205 and enables a patient to make at least one input, wherein the at least one input corresponds to a gross axis measurement.

In the example embodiment shown in FIG. 12B, the spoke diagram 1205 is a series of lines, or long thin rectangles on a solid background, arranged as radii lines on a half-circle dark background 1209. In the example embodiment shown in FIG. 12B, the lines are approximately the same size. The rectangles/lines are made up of alternating parts 1207 and 1208. Alternating parts 1207 and 1208 are different colors, one brighter and the other duller, similar to the alternating parts 902 and 904 discussed above. In the embodiment of FIG. 12B, part 1207 has a brighter background color, while part 1208 has a duller background color.

The system presents the spoke diagram 1205 to one uncorrected eye of a patient at a time. The patient is enabled to make at least one input to select one or more lines that appear different in color from the remaining lines. In one example embodiment where part 1207 is green and part 1208 is red, a line of alternating parts appears yellow at or near the axis of the patient's astigmatism. The selection may be accomplished in any suitable manner, such as by selecting and clicking a line, or a button representing a line, such as buttons 1206.

Referring now to FIG. 11A, another embodiment of the present disclosure is illustrated. FIG. 11A is a screen shot of an example of an embodiment of the system of the present disclosure, wherein the system displays fine spoke diagram 1002, which is a smaller angular portion of spoke diagram 1205, and enables a patient to make at least one input, wherein the at least one input corresponds to a fine axis measurement.

In the example embodiment shown in FIG. 11A, the spoke diagram 1102 is a series of lines, or long thin rectangles on a solid background, arranged as radii lines on a portion of a half-circle dark background. In the example embodiment shown in FIG. 11A, the lines are approximately the same size. The rectangles/lines are made up of alternating parts 1103 and 1104. Alternating parts 1103 and 1104 are different colors, one brighter and the other duller, similar to the alternating parts 902 and 904 discussed above. In the embodiment of FIG. 11A, part 1104 has a brighter background color, while part 1103 has a duller background color.

The system presents the spoke diagram 1102 to one uncorrected eye of a patient at a time. The patient is enabled to make at least one input to select one or more lines that appear different in color from the remaining lines. In one example embodiment where part 1104 is green and part 1103 is red, a line of alternating parts appears yellow at or near the axis of the patient's astigmatism. The selection may be accomplished in any suitable manner, such as by selecting and clicking a line, or a button representing a line, such as buttons 1101. It should be appreciated by one of skill in the art that the fine spoke diagram 1102 represents the portion of the gross spoke diagram 1205 which the patient previously selected as appearing different in color from the other portions of the diagram. It should further be appreciated that fine spoke diagram 1102 uses smaller angular increments between the radii lines to provide a more accurate angular axis determination. In another example embodiment, the patient may first select a wedge from the semi-circle diagram 1105, then use the fine axis diagram 1102 to fine tune the axis determination. In such example, the angular portion used in diagram 1102 would correspond to the wedge section or sections selected by the patient as appearing different from the remainder of the wedges in 1105.

The applicant has surprisingly found that use of a spoke diagram, such as spoke diagrams 1102 and 1205, can be used to accurately determine the axis prescription of a patient. Because the effect of an astigmatism is to distort, or stretch, a patient's vision along an axis, at the portion of the spoke diagram nearby to the patient's axis of astigmatism, the alternating parts 1103 and 1104 of diagram 1102, and parts 1207 and 1208 of diagram 1205 will blur together and appear as a different color than either of the parts individually. It should be appreciated by one of skill in the art that if the patient does not have an astigmatism, none of the lines will appear to change color. It will further be appreciated that any suitable sizing, spacing or shape of alternating parts may be used so long as they are along the various axes.

Referring now to FIG. 12A, another embodiment of the present disclosure is illustrated. FIG. 12A is a screen shot of an example of an embodiment of the system of the present disclosure, wherein the system displays line diagram 1201, and enables a patient to make at least two inputs, wherein the at least two inputs correspond to a cylinder measurement.

In the example embodiment shown in FIG. 12A, the line diagram 1201 is a line, or a long thin rectangle on a solid dark background. The rectangle/line is made up of alternating parts 1202 and 1203. Alternating parts 1202 and 1203 are different colors, one brighter and the other duller, similar to the alternating parts 902 and 904 discussed above. In the embodiment of FIG. 12A, part 1202 has a brighter background color, while part 1203 has a duller background color.

The applicant has surprisingly found that when a patient with astigmatism views a diagram like 1201, they will see a doubled-line, or two lines, instead of the single line presented in the diagram. The applicant has further surprisingly found that the amount of distance between the two appearing lines corresponds to the cylinder measurement of the patient. It should be appreciated that a patient without an astigmatism will only see the single line.

The system displays the line diagram 1201 to one uncorrected eye of a patient at a time. The patient is enabled to make at least two inputs to select the edge of a first appearing line and to select the edge of the second appearing line, as shown by arrows 1200 and 1204 in FIG. 12A. In this way, the patient is identifying the distance between the two appearing lines. The patient is also enabled to select that they only see one line, indicating that they do not have an astigmatism, or that the size of the alternating parts is above their cylinder axis. In such an example, the system may re-present the diagram 1201 with smaller alternating parts. The selection of beginning and ending points of the two-appearing lines may be accomplished in any suitable manner.

Referring now to FIG. 13, another embodiment of the present disclosure is illustrated. FIG. 13 is a screen shot of an example of an embodiment of the system of the present disclosure, wherein the system displays line diagram 1304, and enables a patient to make at least one input, wherein the at least one input corresponds to a cylinder measurement.

In the example embodiment shown in FIG. 13, the line diagram 1304 is a line, or a long thin rectangle on a solid background, wherein the width and height of the line increases when viewed from left to right. The rectangle/line is made up of alternating parts 1301 and 1302. Alternating parts 1301 and 1302 are different colors, one brighter and the other duller, similar to the alternating parts 902 and 904 discussed above. In the embodiment of FIG. 13, part 1302 has a brighter background color, while part 1301 has a duller background color. It should be appreciated that any suitable arrangement of differently sized lines is appropriate. For example, the width and height of the line may decrease from left to right, or the line may be oriented vertically (or at any angle relative to horizontal) as opposed to horizontally. In another example, there may be space between the differently sized line segments. In the example embodiment shown in FIG. 13, there is no space between the differently sized line segments.

The system displays the line diagram 1304 to one uncorrected eye of a patient at a time. The patient is enabled to make at least one input to select one or more line segments that appear different in color from the remaining lines. In one example embodiment where part 1302 is green and part 1301 is red, a line segment of alternating parts appears yellow below the cylinder, or astigmatism severity of the patient's astigmatism. The selection may be accomplished in any suitable manner, such as by selecting and clicking a line segment, or a button representing a line segment, such as buttons 1303.

The applicant has surprisingly found that use of a line diagram, such as line diagram 1304, can be used to accurately determine the cylinder prescription of a patient. Because the effect of an astigmatism is to distort, or stretch, a patient's vision along an axis, when the alternating parts are stretched to correspond to the severity of the patient's astigmatism, the patient's eye will once again be able to resolve the alternating parts in their actual colors. It should be appreciated by one of skill in the art that if the patient does not have an astigmatism, the lines will only appear with the alternating parts in their actual colors.

Referring now to FIGS. 14A-D, other embodiments of the present disclosure are illustrated. FIGS. 14A-D are screen shots of example embodiments of the system of the present disclosure which demonstrate that the alternating parts may be of different sizes or spacing, but still test for the same determination in the astigmatism severity determination. From FIG. 14A to FIG. 14D, the spacing between the alternating parts increases. However, so long as the sizing and spacing is known, each of FIGS. 14A to 14D are usable by the system.

Figure 15:
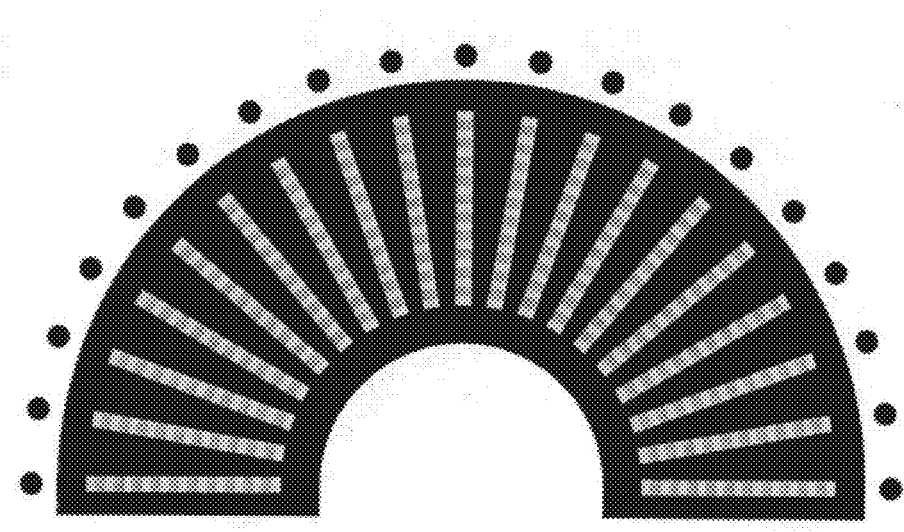
FIG. 15 is a screen shot of an example of an embodiment of the system of the present disclosure, which demonstrates that the alternating parts may be of different sizes or spacing, but still test for the same astigmatism axis determination.

Referring now to FIG. 15, another embodiment of the present disclosure is illustrated. FIG. 15 is a screen shot of an example of an embodiment of the system of the present disclosure, which demonstrates that the alternating parts may be of different sizes or spacing, but still test for the same astigmatism axis determination. Contrast, for example, FIG. 12B with FIG. 15, which has larger alternating parts. However, so long as the sizing and spacing is known, each of FIG. 12B and FIG. 15 are usable by the system.

Figure 16:
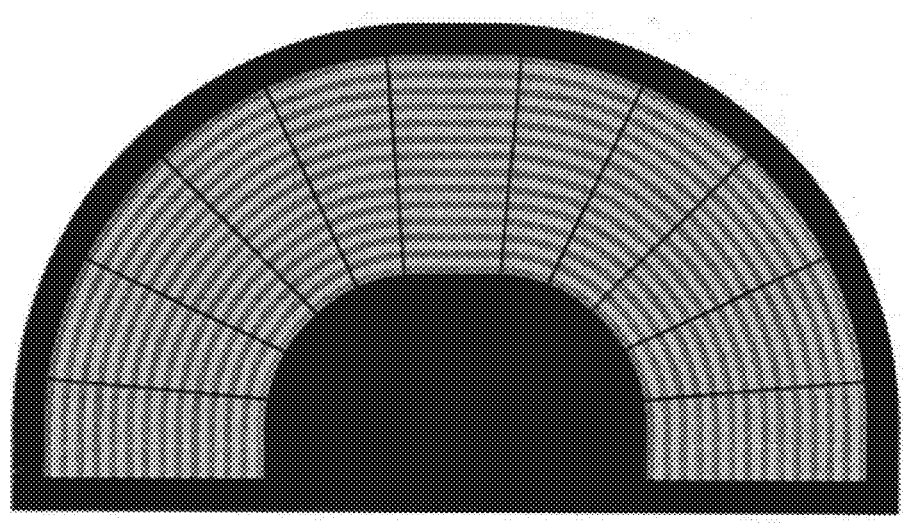
FIG. 16 is a screen shot of an example of an embodiment of the system of the present disclosure, which demonstrates that an astigmatism axis gross determination figure may be modified in size and shape, and stretched in minor fashion, and still be usable by the system for determining an axis of astigmatism for a patient.

Referring now to FIG. 16, another embodiment of the present disclosure is illustrated. FIG. 16 is a screen shot of an example of an embodiment of the system of the present disclosure, which demonstrates that an astigmatism axis gross determination figure may be modified in size and shape, and stretched in minor fashion, and still be usable by the system for determining an axis of astigmatism for a patient. For example, FIG. 16 shows a slight horizontal stretch as compared to the perfectly semicircular figure of FIG. 11B. FIG. 16 also shows, in contrast to FIG. 11B, smaller alternating parts and a greater number of wedges of the figure which do not meet at a center point of the semicircular figure.

In another example embodiment, the system may test or confirm a patient's astigmatism axis by displaying only certain axes. For example, the system may display a set of shapes (such as circles) filled with lines of alternating colors (bright and dull), as described above. In this example embodiment, all of the lines in a given circle would be of the same axis, and the lines in the remaining circles could be at other axes. The system would enable the patient to make at least one input to select a circle that appears blurry to each of their uncorrected eyes, tested individually. For instance, in the case where the bright color is selected from the green family and the dull color is selected from the red family, the patient may select the circle that appears yellow. Based on the at least one input from the patient, the system can determine or confirm the patient's axis prescription. For example, in a situation where the test is being given to confirm a prescription, the system will determine if the prescription is confirmed by comparing the axis of the patient's selected circle or circles to the axis it previously determined. If the axis measurements match or are close, then the prescription is confirmed. It should be appreciated that any suitable number of shapes, any suitable number of axes, and any suitable number of iterations of the test may be utilized by the system to initially test or to confirm an axis prescription for a patient.

In another embodiment, the system begins the axis tests by displaying an object(s), image(s), or figure(s) that appears most clearly (when viewed with each uncorrected eye of a patient at a time) for those patients with a 90 degree or 180 degree astigmatism axis. As is known in the art, the most common astigmatism orientations are at 90 degrees or 180 degrees. This is caused by the cornea of a patient's eye not being round, like a softball, but instead more flattened around the edges, like a football shape. The most common corneal surface shapes are horizontal and vertical, yielding the 90 degree or 180 degree axis of astigmatism (sometimes called "regular astigmatism"). Astigmatism errors in other axes (sometimes called "irregular astigmatism") are less common, thus, from a time management perspective, it is best to start from the most common axes, and test the less common axes only when the patient's input(s) indicate that they do not have an astigmatism axis of 90 degrees or 180 degrees. Starting from the most likely axes will speed up the testing process, which is more convenient for the patient.

In such an example embodiment, the system displays object(s), image(s), or figure(s) that will appear sharper for patient's with a 90 degree astigmatism (when viewed with each uncorrected eye of a patient at a time), contrasted with object(s), image(s), or figure(s) that do not appear as sharp for those patients. In a further example embodiment, the contrasting object(s), image(s), or figure(s) are displayed at a 180 degree axis thereby testing for the 90 degree or 180 degree astigmatism axis together, which may save time and be more convenient for the patient. In another example embodiment, multiple iterations of object(s), image(s), or figure(s) may be displayed, where the first displayed set includes, for example, a 90 degree axis portion and other axes portions, and a second set may include a 180 degree axis portion and other axes portions. In a further example embodiment, if the patient's input(s) indicate that they do not have an astigmatism axis of 90 degrees or 180 degrees, the system will test for an axis in the 45 and 135 degree angles in the manner described above, or herein. If the patient's inputs still do not indicate that they have an astigmatism axis of 45 or 135 degrees, the system may continue testing other axis options in the manner described in this paragraph or elsewhere in this disclosure. In a still further example embodiment, if the patient's inputs still do not indicate that they have an astigmatism axis of 45 or 135 degrees the system will estimate a determination that the patient does not have an astigmatism and move on to another portion of the examination.

In another example embodiment, the system may test or confirm a patient's cylinder prescription by displaying spaced-apart shapes. Applicant has surprisingly found that spaced-apart shapes located along the patient's axis of astigmatism and spaced correspondingly to the cylinder of the patient (or higher) will appear to touch when viewed with the patient's uncorrected eye (each eye individually). For example, the system may display two or more dots in a grid or any other suitable pattern, where at least two of the dots we spaced along the patient's axis of astigmatism. The system would enable the patient to make at least one input to select or otherwise identify the dots that appear to each of their uncorrected eyes, tested individually, to be touching. Based on the at least one input from the patient, the system can determine or confirm the patient's cylinder prescription, where the actual distance between the dots that appear to the uncorrected eye of the patient to be touching corresponds to a cylinder measurement. For example, in a situation where the test is being given to confirm a prescription, the system will determine if the prescription is confirmed by comparing the cylinder of the patient's selected dots to the cylinder it previously determined. If the cylinder measurements match or are close, then the prescription is confirmed. It should be appreciated that any suitable number of shapes, any suitable number of axes, any suitable colors, and any suitable number of iterations of the test may be utilized by the system to initially test or to confirm a cylinder prescription for a patient. It should further be appreciated that the spaced apart shapes may be spaced at different intervals, or that more than one display (with varying intervals between the shapes) may be used in order to fine tune the cylinder determination.

In a further example embodiment where the system tests or confirms a patient's cylinder prescription by displaying spaced-apart shapes, the system may display a single shape (i.e., a triangle) split into multiple pieces, or multiple shapes, where the pieces/shapes are displayed as separated from each other with blank space along the patient's already-determined or known axis of astigmatism. In one example, these spaced apart pieces/shapes are displayed as same color or wavelength. In another example, the spaced apart pieces/shapes are displayed as different colors. In such an embodiment, the system displays the spaced apart pieces/shapes and iterates the size of the separation until the patient's inputs indicate that the astigmatism blur of the viewed pieces/shapes are such that the pieces/shapes appear to be just touching (when viewed with each uncorrected eye of a patient at a time). As discussed previously, the system may enable the patient to make one or more inputs to increase or decrease the spacing between the pieces/shapes, the system may automatically move the pieces/shapes and enable the patient to make at least one input to stop the movement, or a combination of both. As discussed in detail above, the real difference in spacing between the displayed figures/shapes when they appear, to the uncorrected eye of a patient with astigmatism, corresponds to the severity of the astigmatism (i.e., cylinder). Thus, the system determines a cylinder measurement from the patient's inputs regarding when the displayed pieces/shapes appear to be touching.

It should be appreciated that all the astigmatism determination tests described with reference to FIGS. 9A through 16 can consist of alternating parts in any suitable shapes, including, but not limited to the squares and rectangles depicted in the Figures, and any suitable number or combination of alternating colors in any suitable color families. It should further be appreciated that whenever a patient cannot see a color change relative to the other figures displayed, it may be because of one of the following issues: (1) the patient does not have an astigmatism; (2) the size of the displayed alternating parts corresponds to a higher cylinder error than the patient has; and/or (3) the diagram is not at the patient's axis of astigmatism. To address situation (1), the system may enable a patient to make an input indicating that they do no have an astigmatism. To address situation (2), the system may decrease the size of the alternating parts, re-display the diagram, and query the patient again regarding any perceived color change. To address situation (3), the system may re-determine the axis by presenting the patient with a same or with a different axis test.

Figure 17:
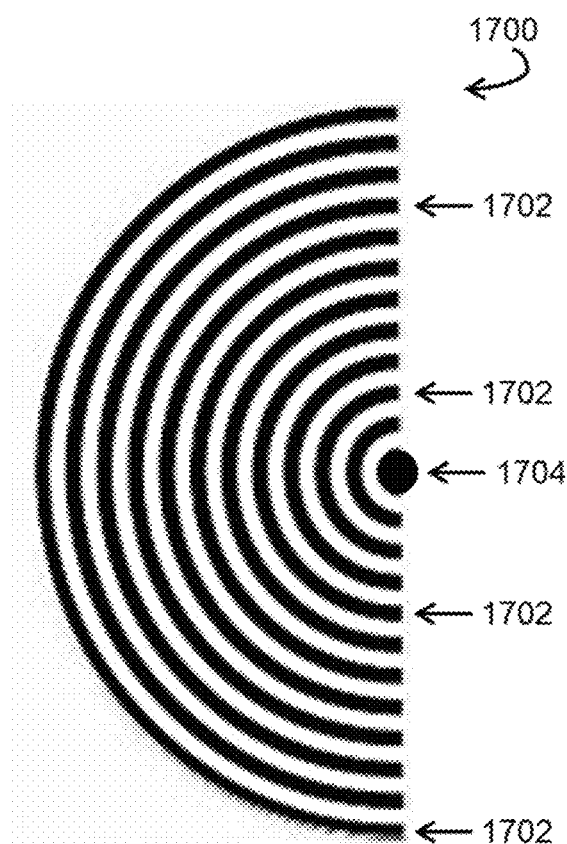
FIG. 17 is a screen shot of an example of an embodiment of the system of the present disclosure, which demonstrates a possible configuration for a macular degeneration test.

Referring now to FIG. 17, another embodiment of the present disclosure is illustrated. FIG. 17 is a screen shot of an example of an embodiment of the system of the present disclosure, which demonstrates a possible configuration for a macular degeneration test. By using such a test, the system enables a patient to conduct an examination of the locations in which they have lost a partial amount or full amount of vision. As is well-known in the art, it is standard practice for optometrists to test this using a simple grid on a sheet of paper (lines left to right and top to bottom) with a marked center. The patient is told to stare at the center with one eye at a time and draw with a pencil any area that appear distorted, missing, or otherwise different than the rest. The optometrist notes in the patient's chart which parts of their retina are damaged. Such a test is useful for macular degeneration, where patients lose their central vision, as well as other retinal issues such as diabetic retinopathy, where specific parts of ones vision become missing or blurry. In contrast to this prior art system, the system of the present disclosure is more advanced. The system displays a figure including a set of curved lines. In the embodiment shown in FIG. 17, the FIG. 1700 has generally semicircular curved lines 1702 opening to the right, and a center region 1704. The system instructs the patient to focus on the center region with a single uncorrected eye at a time, and enables the patient to select any lines which appear to have blurry or missing portions. Alternatively, the system enables the patient to select the portions of the lines which appear to be blurry or missing. The system then displays a similar set of curved lines, but this time with the opening facing some other direction, such as left. In one embodiment, the second figure is displayed as opening to the opposite side as the first figure. It should be appreciated that the orientation of the curved lines may differ in shape or actual apex angle, and may be any suitable shape or apex angle. The system increases the intensity of the user-selected lines or parts of lines and enables the patient to make at least one input regarding whether their vision is improved in those areas based on the increase in intensity. In should be appreciated by one of skill in the art that the at least one input corresponds to a magnification level for that region of a patient's vision, which corresponds to a particular location on the patient's retina which has experienced at least some vision loss. The system may then use the determined magnification level for lens creation to create a specific customized lens with precise additional magnification levels in certain locations to aid in the patient's overall ability to see throughout their full field of vision. In one embodiment, the system can be used to keep track of macular degeneration (or other degenerative vision disease) at home, and monitor changes as vision changes progress. It should be appreciated by one of skill in the art that such routine testing is important for those with or at risk for vision issues as a sudden change or threshold level of change can be detrimental, and may need physician evaluation immediately.

In another example embodiment of a vision loss test, the system uses straight lines instead of the curved lines described above with reference to FIG. 17. In one such example embodiment, the displayed first figure includes vertical lines, and the system enables the patient to make at least one input to select the line or lines, or portions of lines that appear distorted or to have parts missing. The system then displays horizontal lines and enables the patient to make at least one input to select the line or lines, or portions of lines that appear distorted or to have parts missing. It should be appreciated by one of skill in the art that the lines can be any angle or format, any thickness or color, and can also be employed with a combination of straight and curved lines, or a combination of semi-straight or modified lines in any suitable combination so long as the patient is enabled to identify, and the system is thus able to determine, the coordinates of the section(s) on the patient's retina that correlate(s) to missing or impaired vision. It should further be appreciated that if the patient-identified lines are of a type of circular distortion or circular vision loss, a system such as that described above can easily identify that type and can thus isolate any future changes in vision loss that differ from the original regions. One such example of vision loss occurs in those with diabetic changes, or those with advanced macular degeneration. Traditional vision exams typically only monitor these changes every six months to a year and do not allow for a steady progression analysis to take place. In the system described by the present disclosure, the testing and analysis can easily and conveniently be done with greater frequency such that any changes can be detected in a more accurate and time-sensitive manner. Further, it is contemplated that such testing results may be stored and accumulated in a generic database so that the system may compare vision loss data of a specific patient to that of the general population, by analyzing vision loss between right and left eye data points of an individual to that of right and left eye intervals of that of the entire population or data set of patients stored in the database of the system.

In an embodiment, the system includes determining the skew, and thus, quality, of a patient's progressive lenses. Progressive lenses, also called progressive addition lenses (PAL), progressive power lenses, graduated prescription lenses, and varifocal or multifocal lenses, are corrective lenses used in eyeglasses to correct presbyopia and other disorders. Progressive lenses include at least two different prescriptions in different parts of the lens, and a gradient between them. Generally, the progressive lenses begin with the patient's distance prescription near the top of the lens and graduate to the addition (or reading glasses) power prescription near the bottom of the lens. The gradient can be as smooth or long as is necessary for patient comfort. However, the progression of the prescriptions in these lenses create regions of aberration away from the optic axis, causing blur or skew, which varies in relation to the quality of the lens. The higher the quality of the lens, the lower the blur, while the lower the quality of the lens, the higher the blur. Thus, it is advantageous to inform patients of the blur inherent in progressive lenses, its causes, and options for decreasing blur and increasing clarity. In one example embodiment, the system displays a figure. In a further example embodiment, the displayed figure is a grid of lines, similar to that shown at reference numeral 408a in FIG. 4A, or that described above with reference to the optometrist-based prior art macular degeneration test. It should be appreciated that the system may fill an entire computerized screen with such a grid, or a portion of the computerized screen. The system instructs the patient to view the displayed figure with one corrected eye (wearing a progressive lens) at a time. The system enables the patient to make at least one input to identify areas of distortion or blurriness. It should be appreciated that any suitable method of user-input may be enabled, such as outlining or drawing with a cursor, simple point-and-click selection, via a touch screen, via a remote control, by voice control, or by other known input devices and methods. The system may then describe the amount of distortion present in the lens by a simple percentage (i.e. if the patient selects 5 percent of the blocks as distorted or blurry, they would have 5% distortion) and advise the patient what reduction in level of distortion a higher quality lens might yield.

It should further be appreciated that both the vision loss test and the progressive lens check test described in the preceding paragraphs can be employed by the system displaying a simple Amsler grid image with lines running up and down and left to right and enabling a patient to select the areas that look blurry or missing via any suitable input and selection means. It should further be appreciated at any suitable color combination may be used, such as black lines on a white background (black-on-white), blue-on-yellow, blue-on-red, white-on-red, or any other suitable combination of colors.

In another example embodiment of the present disclosure, the system includes a visual field test. Typically, a patient tests their visual field using a specific machine located in-office at a doctor visit. The conventional visual field testing machine operates as follows: a patient places their head against or into a machine and looks through a viewfinder. The machine tests each eye individually (by for example, blocking the view of the eye not being tested) and instructs the patient to focus their eye on a center dot, and click a button (or other input device) with their hand to select when they can see a dot being projected into their field of view through the viewfinder. The machine flashes dots relatively quickly, and if a patient does not make an input that they saw a dot, the machine marks the spot associated with that dot as having some vision loss. Often, the machine will re-test those areas later, lengthening the process for testing the patient. When performed at a doctor's office, the test is often difficult and uncomfortable for a patient to take. Many patients find it difficult to concentrate for such a long period of time, and elderly patients often end up falling asleep while taking the test. Nevertheless, a visual field test is an important diagnostic tool used for the determination and routine follow up patients with glaucoma, brain tumors, diabetes, and many other conditions. Thus, it would be advantageous to provide a visual field test which may be conducted at a location remote from a doctor's office and convenient for the patient, such as in the patient's home. Additionally, at a remote location, the patient may take their time with test, and pause the test if they become distracted or tired, thus yielding a more accurate result. In an example embodiment of the present disclosure, the system includes a visual field test that a patient is enabled to take at a location remote from a doctor's office. In such a system, the patient may be instructed to focus on a central dot (or other shape) as is conventional, or may be instructed to focus on a cursor present on the computerized screen. As is typical, the system tests one eye of a patient at a time while focusing on a location. A weak dot (or other suitable shape or figure) is displayed on the screen, in an area corresponding to a part of the patient's visual field, and the patient is enabled to make at least one input to connote that they saw the dot. Any suitable input method may be employed by the system, such as enabling the patient to move their mouse over to that area the dot appeared to click it, touching the area (if using a touch-screen device), selecting a button, voice control, or other suitable methods. If the patient is too slow to make the at least one input, the system will flash another dot on the computerized screen and flag that area to re-test or as having some vision loss. The time interval for displaying the dot on the computerized screen is generally fast, and may be any suitable amount of time, such as 0.2 seconds. The system enables the patient to make at least one input to cause the display of the dot to be adjusted (longer or shorter). Once the system has at least fully tested the locations in patient's visual field and received any associated inputs from the patient, it determines the patient's visual field based on those recorded inputs, and any lack of recorded inputs. The system may further adjust the light intensity of the displayed shape or figure, or display the shape or figure in any suitable color or combination of colors.

One potential issue with such a system is that a patient may move during the test (even if instructed not to) which would cause the location of the dots on the screen to become associated with a new position on the patient's eye. Thus, the system may include a method to determine if the patient has moved during the test. One possible method is to determine and periodically check the location of the patient's blind spot. As is known in the art, each person has a physiological blind spot in each eye where the optic nerve passes through the optic disc of the retina since there are no light-detecting photoreceptor cells at that location. The blind spot location may be determined via methods well-known in the art, such as by displaying two shapes or figures a known distance apart and instructing the user to cover one eye, look at the shape or figure opposite that eye, and move their eye closer to or further from the screen until the shape or figure disappears. The other side of the blind spot is determined by when the opposite effect occurs. The system may also periodically display dots in the blind spot of the patient. If the patient makes at least one input connoting that they see a dot that should have been in their blind spot, the system will determine that the test has become inaccurate and recalibrate based on the new location of the patient. It should be appreciated that any suitable method of determining whether a patient has moved may be employed by the system in addition to or in place of the above-described methods.

Another potential issue with such a system is that the patient needs to know how far away from the screen to place their eye. Thus, the system may include a method to determine how far the patient needs to be. One possible method is to use the determined location of the patient's blind spot, as is conventional and described above. Alternatively, the system may use any suitable distance calculation method, such as those known in the art or described herein.

It should be appreciated by one of skill in the art that a static question-based system, as opposed to a dynamically-changing-images-based system, may be utilized by the system. In an example embodiment of a static question-based system, the system may display four figures, three identical, and one different. The system would enable the patient to make at least one input to identify the different figure. In such a system, the figures might begin relatively large in size, and as the patient correctly selects the different figure, the system would steadily decrease the size of the displayed figures until the patient is no longer able to correctly select the different figure. It should be appreciated by one of skill in the art that if the starting size, the rate of decrease in size, and the number of correct inputs are known, the system can calculate the appropriate sphere measurement for the patient's prescription. It should further be appreciated that any kind of figure may be used, such as letters, numbers or shapes, that any suitable number of figures greater than one can be used, such as 2, 3, 4 or more, and that any suitable number of similar or different figures may be used. For example, the system may display five figures, three identical and two different. It should also be appreciated that any suitable input device may be used, such as clicking via a cursor, mouse, or trackpad, via a touch screen, via a remote control, by voice control, or by other known input devices and methods.

In another embodiment, the system includes the measurement of the corneal surface of a patient. In such a system, the patient's eye is illuminated with a series of concentric rings of any suitable number, such as two, three, four, five, six, or more, having a known distance between each ring. In one example embodiment, the rings are each the same known distance apart. In another example embodiment, at least one ring is a different known distance apart from its neighboring rings. The illumination of the patient's eye may occur in any suitable manner, such as via projection. After the patient's eye has been illuminated, the system takes a picture of the patient's eye illuminated with the concentric rings. In an alternative embodiment, the system enables the patient (or an assistant of the patient) to take the picture using the system, or using another mode of the patient terminal on which the system is being used. In another alternative embodiment, the system instructs the patient (or an assistant of a patient) to take the picture using a separate camera device, such as may found in a digital camera, a camera phone, a camera-enabled computer or tablet, or any other suitable camera device. Applicants have surprisingly found that the distortion in the spacing between the concentric rings as they appear illuminated on the eye of a patient corresponds to the topology of the patient's cornea. In particular, Applicants have surprisingly found that when the illuminated concentric rings appear closer together, the corneal structure is steeper, whereas if the illuminated concentric rings appear further apart, the corneal structure is flatter. Thus, the system is able to determine the exact corneal steepness based on the separation distance between the illuminated corneal rings compared to the original known separation between the concentric rings. The system is also able to detect if the patient's cornea has a malformed surface, such as keratoconus or an injury based on the appearance of the illuminated concentric rings on the patient's eye.

In another embodiment the system includes a pupillary distance measurement module. It should be appreciated by one of skill in the art that most inner (medial) and outer (lateral) canthal distances are routinely within a small range around approximately 3 cm in all cultures, races, and genders, as long as the individual is of adult age (generally considered to be 18 years of age or older). Applicants have surprisingly found that, from this known range, the system can determine the scale of an image, and thus calculate additional desired distances, such as a patient's pupillary distance. Once the system has determined the pupillary distance of the patient from an image of the patient based, in part upon the scale of the image and the known canthal ranges, the system may enable the patient to virtually and view various glasses frames sized to fit the image of their face, and their determined pupillary distance. In such an embodiment, the system may display an image of the patient with mock eyeglass frames displayed over the top of the patient's face, and may enable the patient to modify the appearance of the frames, for example, by changing the size, shape, color, material, texture, etc. of the mock frames. It should be appreciated by one of skill in the art that other desired facial measurements may be determined by the system based upon the known canthal distances, and that any other desired clothing or accessories may be virtually "fit" via the methods disclosed herein. One of skill in the art should further appreciate that the methods disclosed herein may be applied outside of the context of the facial structure to any part of a human or animal body known to have a standard or approximate standard size, and thus may be used to virtually browse and "fit" any suitable type of clothing or accessory, matched to the size of the underlying image.

In another example embodiment, the system includes a method of determining a pupillary distance measurement of a patient wherein the patient does not need to utilize an outside source of measurement. Known prior art systems determine distances remotely by, for example, requesting the patient to take a photograph of their face, while simultaneously hold up an object of known size (such as a credit card or other real life object) nearby to their eyes in order for the system to scale how far apart the patient's eyes are. However, in the example embodiments of the present disclosure, the system does not require the use of any real life object to scale an image of a face because it utilizes average sizes of an adult eye. In other words, the system utilizes at least the average canthal distances across all races and genders in order to determine an average fixed position in real space as described above. The system then determines the distance between the pupils of the patient based on an image of the patient (either taken directly of the individual using a web camera, phone camera, or any other suitable camera or video device, or taken from a previous photograph of the patient), scaled according to the canthal regions of the patient and the determined average canthal distance (at least in part) to determine the pupillary distance of an patient's face.

It should further be appreciated by one of skill in the art that the above-described pupillary distance module can be used to calculate other facial characteristics or biometric data which may be used to uniquely identify an individual. For example, the system may use the known canthal distance to calculate the face width and/or height of a patient positioned in any suitable manner, such as straight-on to the camera, or full or partial profile. It should be appreciated that biometric data calculated by the system (such as pupillary distance, or other facial dimensions) may be used by a camera-enabled device to lock or unlock access to various applications on the device (or the device itself) based on a comparison between the biometric data known by the device and the biometric data of the person sensed by the camera of the device. If the known biometric data and the sensed biometric data are similar to a high-enough degree (such as the same, a statistically insignificant difference apart, or close to the same within a confidence range) then the device will identify the sensed person as the known person and allow the sensed person access. It should be appreciated that such a biometric-based system works because certain facial proportions and measurements are unique to individuals. Potential problems with such a system include that a person unknown to the system may try to trick the system into authenticating a photograph or video of the known person. The system would then recognize the biometric data of the photograph or video and allow access without the known person actually being present. To avoid these problems, the system may instruct the person desiring access to blink an eye (or blink either or both eyes in a random or predetermined combination or pattern). It should be appreciated by one of skill in the art that any suitable and system-recognizable facial expression or combination of facial expressions may be used (e.g. a smile and a wink, sticking a tongue out, etc.). If the camera-enabled device is also flash enabled, the system may activate the flash to determine whether there is an actual person (as opposed to a recording or photograph) present. In activating the flash, a person would still be visible to the camera sensor, but the photograph or video would be washed out and difficult to sense. The system may also sense or detect shadows on the face (and whether they change) to confirm a real person is present.

In a further embodiment, the pupillary distance measurement system/biometric access system may enable the known person to access to lock or unlock access to various applications on the device (or the device itself). In this further embodiment, different suitable and system-recognizable facial expressions or combinations of facial expressions may be used to access or quit out of different applications (or the device itself). For example, the patient may stick their tongue out to access the device, may wink the right eye then the left eye to access one application, such as a mailbox, then may wink the left eye followed by the right eye to access a second application. It should be appreciated that these combinations of suitable and system-recognizable facial expressions may be used as shortcuts to perform actions inside an application as well as to provide access (or close out of) applications or the device itself.

In another embodiment, the system includes an air puff tonometer test. Such a test may be implemented for a mobile device, in a stand-alone location, in a kiosk-type setting, or in any suitable location, such as by utilizing a small and simple attachable reflexive device that ejects a force of air through a small tiny opening by methods known in the art. It should be appreciated by one of skill in the art that the puff of air will be forced onto the cornea of a human or non-human eye, in order to measure its intraocular pressure. Such an attachable reflexive device may include a high powered photographic lens system that will allow the camera to determine how much the cornea has flattened in response to the puff of air. In an alternate embodiment, the system includes a sensor to measure a pushback or return of air to the sensor after the air has been puffed to the patient's cornea. It should be appreciated by one of skill in the art that the sensor is capable of measuring the amount of air return in both intensity and delay. In such an embodiment, the system determines the intraocular pressure of the patient based on the sensor measurements. It should further be appreciated that the system may utilize more than form of measurement and/or more than one iteration of measurement to ensure accuracy. In using such a attachable reflexive device, the patient is enabled to measure their intraocular pressure in the manner most convenient or comfortable for the patient.

In another embodiment the system includes capability to allow the patient to query a database of eyeglass frames. In one example embodiment of such a system, the system enables a patient to photograph eyeglass frames which they like, or which they already own, and input the image into the system. In a further embodiment, the system may instruct the patient to take the photograph of the frames straight on, as well as with one or two side views of the frames, while the frames are either on or off of the patient. The system utilize the photograph or photographs to determine frame characteristics such as size, shape, size, color, texture, materials, or any other suitable characteristic to query the database of frames known to the system for matching or similar frames which the patient may prefer. The system may determine the characteristics of the photographed frames in any suitable manner, such as a quick wireframe analysis of the frames on the patient's face. As disclosed herein, the system is enabled to determine the necessary dimensions of the patient's face to accurately determine matching or similar frame selections to display to the patient. In one example embodiment of such a system, patients may browse frames at their local optical shops, and take photographs of their preferred frames, then use the disclosed online, mobile phone application, or kiosk-based system to purchase a pair of frames that are close in shape, size, color, or any other characteristic. In another example embodiment, the system may query the database based on a picture of someone other than the patient, such as a picture provided by the patient of someone unknown to the system, or a picture from a publication, such as a magazine.

In one example embodiment, the system determines near and/or far sightedness by observing behavior and using the properties of nearsighted and farsighted patients. Nearsighted people can see near things more clearly than they can see things that are farther away, while farsighted people can see far things more clearly than they can see nearer things. In an embodiment to test for nearsightedness and farsightedness, the system can determine which condition the patient is experiencing by instructing the patient to view a near image and a far image simultaneously (or near simultaneously), then enabling the patient to make an input reflecting which image appears more clearly. In one embodiment, the near image would be about a foot away from a computerized screen, such as a computer monitor and the far image would be more distant than about a foot away, such as an a computerized screen held at arm's length (such as a smartphone in an extended arm of the patient). In another embodiment, the near image would be a computerized screen held at arm's length (such as a smartphone in an extended arm of the patient) and the far distance can be more distance that arm's length, such as 6-10 feet away from a computerized screen, such as a computer monitor, kiosk, or tablet. Once the patient can view the two images at the different distances, the system instructs them to make an input regarding whether they can see some detail of the image. For instance, in an embodiment where the image is a series of characters, the system may ask the patient to make an input when they can identify which character is different from the others, using one uncorrected eye at a time. The system enables the patient to make at least one input to reflect the smallest sized image of which they can make out the system-identified detail by adjusting the sizes of the images using methods described in detail elsewhere in this disclosure. The image may be kept the same on both screens (increased and decreased together) or may be different sizes on each screen. Based on the patient's inputs regarding the smallest size image they can see a detail of close and far away, the system can determine whether the patient is nearsighted or farsighted. In a further embodiment, the system additionally uses red and green overlays on the images in order to either increase or decrease chromatic aberration.

The near and far distances the system instructs the patient to use may be based on age. This would be advantageous since younger people tend to have better near vision than older people, because as one ages, one loses some of their ability to accommodate for close reading. Thus, the system takes age into account to yield a more accurate determination. In one embodiment, the system determines the positioning of different-aged individuals by using a visual field. For instance, the system may display a figure with a portion on the right side of the screen (an "X" for example, when the patient is testing their uncorrected right eye) and a portion on the left side of the screen (such as a vertical line). The patient is instructed to move their eye towards the X, until they cannot see the vertical line in their peripheral vision. Someone who is 40 years old will have a vertical line further away from the X, than say someone who is 20 years old, because the 20 year old individual must move their head closer to the computer screen before they can no longer see the X in their peripheral vision.

In another embodiment, the system includes a sound vibration ocular pressure sensor to determine the ocular pressure of a patient. It should be appreciated by one of skill in the art that such as system is based on the known fact that objects will vibrate in response to sound waves. Applicants have surprisingly found that the various types and frequencies of sound waves correlate directly to the associated vibration that occurs in the cornea based upon the ocular pressure, and that these vibrations are measurable by a camera sensor capturing changes in light reflections from a camera or by a microphone or other suitable sensor that captures the frequency of the sound reflected back from the pulsated eye. The system pulsates sound waves in any suitable standard or variable frequency against the corneal structure of the patient, then measures the vibration of the cornea to determine the pressure inside the cornea. Applicants have surprisingly found that changes in the light reflections from a camera or measured frequency of reflected sound from a pulsated eye correlate with the vibration in the cornea based upon the ocular pressure. Applicants have further surprisingly found that such systems are functional using ultrasonic sound waves, infrasonic sound waves and/or acoustic sound waves. In one example embodiment, a combination of infrasonic and acoustic sound waves are pulsated in various time intervals and intensities and sound/decibel levels, and the patient's cornea vibrates in accordance to the various levels and in accordance with its internal pressure. It should be appreciated by one of skill in the art that any suitable speaker or device may generate the sound waves, such as the standard speaker on a cell phone, tablet, or personal computer.

In another embodiment, the system includes a high powered plus lens to isolate hyperopia and hyperopic prescriptions. This lens may be included or simulated in any suitable application, such as in a personal computer application, a mobile phone application, or in a kiosk-based application. It should be appreciated by one of skill in the art that a high powered plus lens enables the system to correct for latent hyperopia, as well as isolate the patient from using their eye muscles' natural accommodative ability to focus through a slightly incorrect prescription, thus enabling the system to provide a more accurate prescription.

In another embodiment, the system includes an additional method to determine the distance between the patient and the computerized screen of the patient terminal, or other desired distances, such as pupillary distance. The system relies upon the known canthal distance of the adult patient and an additional data point to calculate the distance between the terminal or camera and the patient. The additional data point can be any suitable data point, such as the height of the patient (if the terminal or camera can see the entire height of the patient), or known camera specifications of particular device or patient terminal. The system uses this known information to determine the distance between the terminal or camera from the patient. In one example embodiment, the system may know the canthal distance of the patient is approximately 3 cm, and may determine that on the image of the patient from a known camera device (such as from a camera of known manufacture) that canthal distance is represented by a certain number of pixels, then the system may, from these known points, identify the scale of the image of the patient, and thus the distance between terminal or patient. In an alternative embodiment, the system uses (or instructs the patient to use one or more of) two camera devices separated vertically or horizontally by a known distance to measure the desired distance (distance between the patient and the camera devices, or some other desired distance). It should be appreciated by one of skill in the art that such a system may also be used to determine pupillary distance.

It should be appreciated that each of the disclosures above may be implemented in a kiosk-type system, either singly, individually, or in combination with several kiosks, to provide a complete eye examination to evaluate various parts of the eye and refractive system. Examples of various types of known systems which may be incorporated into such a system include: an eye pressure measurement system, a photographing system for the photographing the front and/or back of the eye, a refraction system, and a system to measure all ancillary tests of an eye exam. In one example embodiment, the system includes a distance range finder to determine the distance a patient moves their eye away from a screen, and enables the patient to make a input at the distance they first notice an image being sharp with each individual eye. It should be appreciated that in such an embodiment, the test will be done with each eye independently, and any suitable number of times, such as one time, two times, three times, or more. The systems determines a portion of a prescription for the patient based on these one or more tests, and based in part on the principle that the focal point of an eye corresponds to the dioptric power error of an eye, in that the measurement of initial close focus is 1/distance, where distance is in meters. It should be appreciated that such a system operates without the need to for the patient to move their footing position away from their current position.

In another example embodiment, the system is embedded into a kiosk-based structure, enabling the patient to undergo any of the testing/diagnostics described herein in any location that the kiosk is located in, which may be any suitable location including locations in or nearby to an eyeglasses and/or contacts retail location, an generic retail location, such as a shopping mall or store front, an optometrist or ophthalmologist's office, another type of doctor's office, nearby to Department of Motor Vehicles or Secretary of State facilities, or any other location. It should be appreciated by one of skill in the art that an advantage to a kiosk-based system in accordance with the present disclosure would be that such as system would not need to utilize any lens assemblies in order to refract the patient. The kiosk could therefore be completely lens free in order to determine a refractive prescription for a patient. This would save the kiosk manufacturer or operator both money and effort in development, as well as bulkiness and complexity in the overall structure. The kiosk-based system may include any of the features described herein, in any suitable combination or number including a lensless refraction system, eye health testing, biometric testing, a system to grind lenses, a system to print of frames, etc. One of skill in the art should appreciate that a greater number of features may provide increased convenience to the patient, for example, if the system could refract a patient, generate a corrective lenses prescription, and provide the patient with the prescribed corrective lenses in a one-stop location and time period. It should further be appreciated by one of skill in the art that a kiosk-based system would be unique from an in-home lensless experience (as also described herein), for several reasons, including because of functionality described above which would not be practicable in an -in-home setting (such as lens grinding or frame printing) or because it could require smaller distances (and space requirements) by use of a conventional mirror arrangement as is well-known in the art. Mirror arrangements of this sort are routinely used in doctors' offices to simulate 20 feet when, in fact, most offices only have less than 12 feet of total distance available due to the high cost of rent or to maximize exam rooms.

In another further embodiment, the system is an all-in-one corrective lenses production device that will determine the patient's prescription in the manners described herein, and enables a patient to select a glasses frame and a type, color and coating for a lens, as is known in the art. The system will then create the frame while the patient waits via a 3D printer or other known methods, and create the lens with a gel-type system that creates the lens and hardens the lens while the patient waits, or by any other method which is known in the art for the creation of lenses. An entire system in accordance with this embodiment advantageously provides convenience for the patient, as it contains the three necessary components to finalize a pair of spectacles: a prescription, a frame, and lenses.

It should be appreciated by one of skill in the art that for various modules or portions of the present disclosure which do not require input from a patient, or which are not subjective in nature, the patient may be any suitable patient. For example, the patient may be non-human, such as a pet or a wild animal. In another example, the patient may be of an age or ability level which makes communication difficult, such as a child or a developmentally delayed person. It should further be appreciated that for such patients, the system may instruct an assistant to the patient on proper positioning and any necessary inputs.

In another embodiment, the system determines the former spectacle eyeglasses prescription (myopic, hyperopic, astigmatic, or any combination thereof) of a patient without requiring a written prescription copied into a fillable form by the patient. The system requires only a camera, a computerized screen, and a pair of spectacle lenses. The patient places the camera lens a known distance from a computer monitor. In one example embodiment, an easy way to set or determine the known distance is to use a standard piece of paper (8.5×11 inches) to select the placement of the camera device and/or the computerized screen. In one embodiment, the system instructs the patient to place the camera device 11 inches (or some other distance) from the computerized screen. In another example embodiment, the patient selects the distance between the camera device and the computerized screen and the system enables the patient to input the selected distance. Once the camera device has been placed a known distance from the computerized screen, the patient takes a control picture of the computerized screen, then places one of the spectacle lenses against the camera lens and takes a second picture of the computerized screen. The patient then places the other of the spectacle lenses against the camera lens and takes a third picture of the computerized screen. The computerized screen may display any suitable high-contrast figure, such as a grid or spaced dots. The system receives the control picture, first lens picture, and second lens picture from the camera device via methods for data transfer that are well known in the art, such as though a wired connection (usb, firewire, thunderbolt, etc.), wireless connection (bluetooth, etc.), or via cellular data or internet connections. It would be appreciated by one of skill in the art that placing the spectacle lens over the camera lens will distort, or change, the visual appearance of figure displayed by the system on the computerized screen. Applicants have surprisingly found that by measuring the amount and direction of distortion of the first and second pictures from the control picture over a known distance, the system is able to determine the prescription of the first and second spectacle lenses without a written prescription document.

In another example embodiment the system utilizes a screen that is able to focus its light rays in more than one direction, and at various points in space, such that it is able to specifically focus light rays within a designated small space to make for a more optimal viewing location. This display unit will therefore allow a patient to see an image in focus, regardless of their vision correction, because the display will aim the rays towards the patient and can adjust in real time the rays of light and their position for the user.

In a further embodiment, the system determines both cylinder and axis measurements of a patients' refractive error for each eye at a time by using a single figure on a screen. The patient is enabled to view the figure (using one uncorrected eye at a time) and is enabled to input to the system the extent and reach of the patients' perception of any doubling or overlap effect. It should be appreciated by one of skill in the art that any suitable way of measuring or inputting the doubling or overlap effect can be utilized, such as by expanded or concentric additional figures, or by enabling the patient to place markers where at the outer bounds of the perceived doubling or overlap effect. It should further be appreciated that any suitable figure may be used by the system such as a simple shape, symbol, icon. Applicants have surprisingly found that the perceived doubling or overlap effect corresponds to the axis (by demonstrating the angle the astigmatism causes distortion along) and cylinder (by demonstrating the extent of the astigmatism distortion) measurements of the patient.

In another embodiment, the system can determine either an astigmatism cylinder or axis by displaying a spinning symbol and enabling a patient to view the spinning figure with one uncorrected eye at a time and make an input when the figure appears as a single figure without any residual doubling or overlap effect. It should be appreciated that any suitable figure may be used by the system such as a simple shape, symbol, icon. Applicants have surprisingly found that the disappearance of the doubling or overlap effect caused by an astigmatism corresponds to the axis (by demonstrating the angle the astigmatism causes distortion along) and cylinder (by demonstrating the extent of the astigmatism distortion) measurements of the patient.

In another further embodiment, a system may enable a patient to undergo an additional number of examinations after their initial examination. In one example embodiment, at least one of the additional examinations is performed by the patient using their corrected eyes based on the prescription determined by the system in their initial examination. The system may use the additional number of examinations to refine the correlation of tests performed by the system to the most accurate measurement of the patient's prescription.

In an embodiment, the system includes determining any particular areas of a patient's vision loss or reduction throughout their full field of vision. In one example embodiment, the system displays a figure. In a further example embodiment, the displayed figure is a grid of lines, similar to that shown at reference numeral 408a in FIG. 4A. The system instructs the patient to view the displayed figure with one uncorrected eye at a time, and look to or at a center point of the figure. The center point of the figure may be marked or otherwise identified. The system then enables the patient make at least one input to select areas in the figure which appear distorted, missing, or otherwise different than the rest. The system can use this at least one input to further test the areas of vision loss by either magnifying those certain spots of vision loss, or altering their shapes or intensities to determine if the patient can notice vision improvement. The patient continues to look to or at the center of the figure while the system adjusts at least one of the shape, intensity, color, or other suitable characteristic of each identified area of vision loss. The system enables the patient to make at least one input per previously-identified area of vision loss to connote one or more of the following: (i) the adjustment helped to make the area more clear/less distorted, (ii) the adjustment did not help to make the area more clear/less distorted, (iii) the adjustment made the area clear and not distorted, and (iv) the area is still missing, blurry, or distorted despite the adjustment. The system may then iteratively adjust at least one of the shape, intensity, color, or other suitable characteristic of each identified area of vision loss and again enable the patient to make one or more of the four above-identified inputs. This iterative process may continue until each identified area has been adjusted to appear clear and not distorted to the uncorrected eye of the patient, wherein the adjustment to size, intensity, or other characteristic of each area corresponds to a magnification of a particular location of a spectacle lens. In one example embodiment, the adjustment correlates to the base curve of the lens at that particular location. As an example, if the patient was found to have no distance prescription, but the system identified two areas of vision loss that needed increased magnification with 2 levels of increase (diopters), an example base curve modification would be −4 diopters on the back curve of the lens, and +4 diopters on the front, but +6 curve on the areas that need 2 levels of magnification. This is because a lens has two curved surfaces affecting the vision of the wearer: the front surface and the back surface. The corrective power of a lens is determined by adding the front curve to the back curve. This is expressed by the equation: $F1+F2=FTotal$. Applicants have surprisingly found that adjusting a figure to correct for vision loss in particular areas correlates to base curve measurements for the corresponding locations of a spectacle lens. Possible applications of the above-described system include aiding those patients with macular degeneration, glaucoma, diabetic retinopathy, or other retinal diseases which cause loss of some or all vision in certain locations.

In a further embodiment, the system includes grinding or laser-cutting custom lenses based on the results and prescriptions of the tests described herein. As is well-known in the art, spectacle lenses may be made of glass or plastic, such as lightweight polycarbonate plastic, CR-39 plastic, or high index plastic lenses. Lenses are generally started as "blanks," which are already cut to an approximate base curve/power and need only to be fine tuned to the prescription of each patient. These "blank" lenses are then conventionally processed by grinding and polishing, or laser cutting, edging, and coating. In one embodiment, the system grinds lenses for a patient who has an especially narrow or wide astigmatism angles. In another embodiment, the system grinds lenses with different base curve (diopter) values in different locations to correct for vision loss in those particular areas from diseases such as macular degeneration, glaucoma, diabetic retinopathy, or other retinal diseases. It should be appreciated that such a lens would magnify or minify some parts of patient's sight to adjust for the patient's weakness in parts of their eyesight. In a further embodiment, the transitions between the base curve changes are smooth (as they are in no-line bifocal lenses).

The present disclosure contemplates a variety of different systems each having one or more of a plurality of different features, attributes, or characteristics. It should be appreciated that a "system" as used herein refers to various configurations of: (a) one or more central servers, central controllers, or remote hosts; and/or (b) one or more patient terminals, such as desktop computers, laptop computers, tablet computers or computing devices, personal digital assistants (PDAs), mobile telephones such as smart phones, kiosk devices, and other mobile or stationary computing devices.

For brevity and clarity, unless specifically stated otherwise, "patient terminal" as used herein represents one patient terminal or a plurality of patient terminals, and "central server, central controller, or remote host" as used herein represents one central server, central controller, or remote host or a plurality of central servers, central controllers, or remote hosts.

As noted above, in various embodiments, the system includes a patient terminal in combination with a central server, central controller, or remote host. In such embodiments, the patient terminal is configured to communicate with the central server, central controller, or remote host through a data network or remote communication link.

In certain embodiments in which the system includes a patient terminal in combination with a central server, central controller, or remote host, the central server, central controller, or remote host is any suitable computing device (such as a server) that includes at least one processor and at least one memory device or storage device. As further described below, the patient terminal includes at least one processor configured to transmit and receive data or signals representing events, messages, commands, or any other suitable information between the patient terminal and the central server, central controller, or remote host. The at least one processor of that patient terminal is configured to execute the events, messages, or commands represented by such data or signals in conjunction with the operation of the patient terminal. Moreover, the at least one processor of the central server, central controller, or remote host is configured to transmit and receive data or signals representing events, messages, commands, or any other suitable information between the central server, central controller, or remote host and the patient terminal. The at least one processor of the central server, central controller, or remote host is configured to execute the events, messages, or commands represented by such data or signals in conjunction with the operation of the central server, central controller, or remote host. It should be appreciated that one, more, or each of the functions of the central server, central controller, or remote host may be performed by the at least one processor of the patient terminal. It should be further appreciated that one, more, or each of the functions of the at least one processor of the patient terminal may be performed by the at least one processor of the central server, central controller, or remote host.

In certain such embodiments, computerized instructions for controlling any screens, displays, or interfaces displayed by the patient terminal are executed by the central server, central controller, or remote host. In such "thin client" embodiments, the central server, central controller, or remote host remotely controls screens, displays, or interfaces displayed by the patient terminal, and the patient terminal is utilized to display such screens, displays, or interfaces and to receive one or more inputs or commands. In other such embodiments, computerized instructions for controlling screens, displays, or interfaces displayed by the patient terminal are communicated from the central server, central controller, or remote host to the patient terminal and are stored in at least one memory device of the patient terminal. In such "thick client" embodiments, the at least one processor of the patient terminal executes the computerized instructions to control screens, displays, or interfaces displayed by the patient terminal.

In certain embodiments in which the system includes a patient terminal configured to communicate with a central server, central controller, or remote host through a data network, the data network is a local area network (LAN) in which the patient terminal is located substantially proximate to the central server, central controller, or remote host. In one example, the patient terminal and the central server, central controller, or remote host are located in an eyeglasses and/or contacts retail location. In another example, the patient terminal and the central server, central controller, or remote host are located in an optometrist's or ophthalmologist's office.

In other embodiments in which the system includes a patient terminal configured to communicate with a central server, central controller, or remote host through a data network, the data network is a wide area network (WAN) in which the patient terminal is not necessarily located substantially proximate to the central server, central controller, or remote host. For example, the customer terminal is located: (a) in an area of an eyeglasses and/or contacts retail location different from an area of the eyeglasses and/or contacts retail location in which the central server, central controller, or remote host is located; or (b) in a eyeglasses and/or contacts retail location different from the eyeglasses and/or contacts retail location in which the central server, central controller, or remote host is located. In another example, the central server, central controller, or remote host is not located within a eyeglasses and/or contacts retail location in which the patient terminal is located. In still another example, the customer terminal is located: (a) in an area of an optometrist's or ophthalmologist's office different from an area of the optometrist's or ophthalmologist's office in which the central server, central controller, or remote host is located; or (b) in an optometrist's or ophthalmologist's office different from the optometrist's or ophthalmologist's office in which the central server, central controller, or remote host is located. In another example, the central server, central controller, or remote host is not located within an optometrist's or ophthalmologist's office in which the patient terminal is located. It should be appreciated that in certain embodiments in which the data network is a WAN, the system includes a central server, central controller, or remote host and a customer terminal each located in a different eyeglasses and/or contacts retail location in a same geographic area, such as a same city or a same state. It should be appreciated that systems in which the data network is a WAN are substantially identical to systems in which the data network is a LAN, though the quantity of patient terminals in such systems may vary relative to one another.

In further embodiments in which the system includes a patient terminal configured to communicate with a central server, central controller, or remote host through a data network, the data network is an internet or an intranet. In certain such embodiments, an internet browser of the computer terminal is usable to access an internet page from any location where an internet connection is available. In one such embodiment, after the internet page is accessed, the central server, central controller, or remote host identifies a patient prior to enabling that player to enter any data or participate in any tests. In one example, the central server, central controller, or remote host identifies the patient by requiring a patient account of the patient to be logged into via an input of a unique username and password combination assigned to the patient. It should be appreciated, however, that the central server, central controller, or remote host may identify the patient in any other suitable manner, such as by validating a patient tracking identification number associated with the patient; by validating a unique patient identification number associated with the patient by the central server, central controller, or remote host; or by identifying the patient terminal, such as by identifying the MAC address or the IP address of the internet facilitator. In various embodiments, once the central server, central controller, or remote host identifies the patient, the central server, central controller, or remote host enables the entry of any patient data and the participation in any tests, and displays those tests and screens, displays and interfaces via the internet browser of the patient terminal.

It should be appreciated the system of the present invention may be implemented via any suitable method, such as any computer readable medium. In one embodiment, the computer readable medium is software embedded in a website. In another embodiment, the computer readable medium is software on a non-transitory medium, such as a CD-ROM, storage in local memory at the patient terminal, or the like. In another embodiment, the system is provided in an application programming interface ("API") which may be individually licensed to third parties to include in their websites or other media.

It should be appreciated that the central server, central server, or remote host and the patient terminal are configured to connect to the data network or remote communications link in any suitable manner. In various embodiments, such a connection is accomplished via: a conventional phone line or other data transmission line, a digital subscriber line (DSL), a T-1 line, a coaxial cable, a fiber optic cable, a wireless or wired routing device, a mobile communications network connection (such as a cellular network or mobile internet network), or any other suitable medium. It should be appreciated that the expansion in the quantity of computing devices and the quantity and speed of internet connections in recent years increases opportunities for patients to use a variety of patient terminals to participate in eye tests from an ever-increasing quantity of remote sites. It should also be appreciated that the enhanced bandwidth of digital wireless communications may render such technology suitable for some or all communications, particularly if such communications are encrypted. Higher data transmission speeds may be useful for enhancing the sophistication and response of the display and interaction with players.

It should be appreciated that any suitable patient terminal would be acceptable, so long as the features of the terminal are known by the system. Preferably, the system includes a terminal with a resolution of 800×600 DPI, a second terminal (such as a smart phone-type device) with an input device (such as touch sensing capabilities), and with the ability to run a web browser. Moreover, any suitable space may be used to conduct the testing. Preferably the testing space would be a room with at least 15 feet of linear walking space and the ability to darken the room by dimming lights or closing blinds/curtains. It should be appreciated that these system recommendations are merely recommendations to make the system easier to use and more convenient for the patient, but that any suitable space or device may be used.

It should be appreciated by one of skill in the art that the static (i.e. non-dynamic) figures and diagrams described above with reference to the figures are also capable of being used in the form of physical media, such as paper, poster, plastic, or other printed forms. In such embodiments, the physical media may be displayed to the patient at any suitable location, such as at their home, at an office, or at a corrective lenses retail establishment. The physical media may be view by the patient alone, or may be viewed with the assistance of one or more other persons, such as an assistant or doctor. Further, in such embodiments, the results may be entered into a terminal as described above for the determination of the appropriate prescription measurements.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for determining a corrective lenses prescription for a patient comprising, separately, for each eye of the patient:
   determining an astigmatism prescription for the patient via a computerized screen and without the use of a refractor lens assembly, wherein determining the astigmatism prescription for the patient comprises testing for a cylinder component and an axis component at the same time by presenting at least one diagram to the patient via the computerized screen and enabling the patient to select at least one input per diagram, wherein the at least one input per diagram corresponds to a cylinder measurement and an axis measurement used to determine the cylinder component and the axis component of the corrective lenses prescription for the patient.

2. The method according to claim 1, wherein the method is provided via an internet.

3. The method according to claim 1, wherein presenting the at least one diagram comprises sequentially presenting at least two diagrams comprising at least two portions, and the at least two diagrams differ from each other by at least the spacing between the at least two portions.

4. The method according to claim 3, wherein the at least two diagrams are a same diagram.

5. The method according to claim 1, further comprising:
   acquiring an image of the patient; and
   determining a pupillary distance measurement for the patient based on a known canthal distance based on an age and a gender of the patient and at least one calibration data point that is related to the acquired image of the patient.

6. The method according to claim 1, wherein the method further comprises sending the determined cylinder component and the determined axis component to at least one doctor for review and approval.

7. The method according to claim 1, wherein the cylinder component is based, at least in part, on the cylinder measurements from the at least one input per diagram.

8. The method according to claim 1, wherein the axis component is based, at least in part, on the axis measurements from the at least one input per diagram.

9. The method according to claim 1, further comprising determining a sphere component of the corrective lenses prescription for the patient via the computerized screen by:
   (i) presenting a first figure to a patient via the computerized screen, wherein the first figure is too small to be clearly seen by the patient, and
   (ii) enabling the patient to make at least one input to increase the size of the first figure until it can be just barely be made out by the patient, wherein the at least one input corresponds to a first sphere measurement.

10. The method according to claim 9, wherein determining the sphere component of the corrective lenses prescription for the patient via the computerized screen comprises:
    (iii) presenting a second figure to a patient via the computerized screen, wherein the second figure is large enough to be clearly seen by the patient, and
    (iv) enabling the patient to make at least one input to decrease the size of the second figure just until it can no longer be made out by the patient, wherein the at least one input corresponds to a second sphere measurement.

11. The method according to claim 10, wherein the sphere component is based, at least in part, on the first sphere measurement and the second sphere measurement.

12. The method according to claim 11, wherein at least one of steps (i) and (ii), or steps (iii) and (iv) are repeated at least once.

13. The method according to claim 1, wherein the computerized screen is located a distance from the patient, in a kiosk.

14. The method according to claim 13, wherein the method further comprising instructing the patient to take a determined number of heel-to-toe steps from the computerized screen to reach the distance.

15. The method according to claim 14, wherein the determination of the number of heel-to-toe steps is based on at least a shoe size of the patient.

16. The method according to claim 1, wherein determining the corrective lenses prescription for the patient is based, in part, on a previous corrective lenses prescription for the patient.

17. A non-transitory computer readable medium including a plurality of instructions, which when executed by at least one processor, cause the at least one processor to operate with at least one display device and at least one input device to determine a corrective lenses prescription for a patient comprising, for each eye of a patient:
  (a) determining, without the use of a refractor lens assembly, an astigmatism prescription for the patient by,
    (i) presenting at least one diagram to the patient via the computerized screen, and
    (ii) enabling the patient to select at least one input per diagram, wherein the at least one input per diagram corresponds to a cylinder measurement and an axis measurement used to determine the corrective lenses prescription for the patient;
  (b) determining, without the use of a refractor lens assembly, a power prescription for the patient by,
    (i) presenting a first figure to a patient via the computerized screen, wherein the first figure is too small to be clearly seen by the patient,
    (ii) enabling the patient to make at least one input to increase the size of the first figure until it can just barely be made out by the patient, wherein the at least one input corresponds to a first sphere measurement,
    (iii) presenting a second figure to a patient via the computerized screen, wherein the second figure is large enough to be clearly seen by the patient, and
    (iv) enabling the patient to make at least one input to decrease the size of the second figure just until it can no longer be made out by the patient, wherein the at least one input corresponds to a second sphere measurement;
  wherein a final sphere measurement is based, at least in part, on the first sphere measurement and the second sphere measurement.

18. The non-transitory computer readable medium of claim 17, wherein presenting the at least one diagram comprises sequentially presenting at least two diagrams wherein the at least two diagrams each comprise at least two portions, and the at least two diagrams differ from each other by at least the spacing between the at least two portions.

19. The non-transitory computer readable medium of claim 17, wherein determining the corrective lenses prescription for the patient further comprises:
  acquiring an image of the patient; and
  determining a pupillary distance measurement for the patient based on a known canthal distance based on an age and a gender of the patient and at least one calibration data point that is related to the acquired image of the patient.

20. The non-transitory computer readable medium of claim 17, further comprising sending the determined corrective lenses prescription to at least one doctor for review and approval.

* * * * *